(12) United States Patent
Firmin et al.

(10) Patent No.: US 7,625,705 B2
(45) Date of Patent: Dec. 1, 2009

(54) METHODS AND COMPOSITIONS FOR DETECTION OF A TARGET NUCLEIC ACID SEQUENCE UTILIZING A PROBE WITH A 3' FLAP

(75) Inventors: Andrew Firmin, Jackson, WY (US); Joseph A. Sorge, Wilson, WY (US)

(73) Assignee: Hologic, Inc., Marlborough, MA (US)

( * ) Notice: Subject to any disclaimer, the term of this patent is extended or adjusted under 35 U.S.C. 154(b) by 0 days.

(21) Appl. No.: 11/701,605

(22) Filed: Feb. 1, 2007

(65) Prior Publication Data
US 2008/0026387 A1 Jan. 31, 2008

Related U.S. Application Data

(63) Continuation-in-part of application No. 11/473,678, filed on Jun. 22, 2006, which is a continuation-in-part of application No. 09/728,574, filed on Nov. 30, 2000, now Pat. No. 7,118,860, which is a continuation-in-part of application No. 09/650,888, filed on Aug. 30, 2000, now Pat. No. 6,548,250, which is a continuation-in-part of application No. 09/430,692, filed on Oct. 29, 1999, now Pat. No. 6,528,254.

(51) Int. Cl.
*C12Q 1/68* (2006.01)
*C12P 19/34* (2006.01)
*C07H 21/00* (2006.01)
*C07H 21/02* (2006.01)
*C07H 21/04* (2006.01)

(52) U.S. Cl. .................. 435/6; 435/91.2; 536/22.1; 536/23.1; 536/24.3

(58) Field of Classification Search .............. 435/6; 536/23.1, 24.3
See application file for complete search history.

(56) References Cited

U.S. PATENT DOCUMENTS

| 6,080,868 A * | 6/2000 | Lee et al. ............ 548/100 |
| 6,312,906 B1 * | 11/2001 | Cass et al. ............ 435/6 |
| 2007/0134686 A1 * | 6/2007 | Sorge et al. ............ 435/6 |
| 2007/0161011 A1 * | 7/2007 | Sorge ............ 435/6 |

OTHER PUBLICATIONS

Tyagi et al., Molecular Beacons: Probes that fluoresce upon Hybridization. Nature Biotechnology 14 :303-308 (Mar. 1996).*
Lundberg et al. High fidelity amplification using a thermostable DNA polymerase from Pyrococccus furiosus. Gene 108(1) : 1-6 (1991).*
Cardullo et al. Detection of nucleic acid hybridization by nonradiative fluorescence resonance energy transfer. PNAS 85 : 8790-8794 (1988).*
Beattie et al., Hybridization of DNA targets to glass-tethered oligonucleotide probes. Molecular Biotechnology 4 : 213-225 (1995).*
Ugozzoli et al. Detection of specific alleles by using allele-specific primer extension followed by capture on solid support. GATA 9(4) :107-112 (1992).*

* cited by examiner

*Primary Examiner*—Ethan Whisenant
(74) *Attorney, Agent, or Firm*—Theodore Allen; Paul Muzzi

(57) ABSTRACT

The invention provides compositions, kits and methods of generating a signal indicative of the presence of a target nucleic acid sequence in a sample by forming a cleavage structure. The cleavage structure is formed by incubating a sample containing a target nucleic acid with a downstream probe that forms a 3' flap when hybridized to the target. The cleavage structure is cleaved with a 3' nuclease and a detectable signal is produced.

69 Claims, 13 Drawing Sheets

```
                                                              (SEQ ID NO: 4)
                                                           5' (SEQ ID NO: 41)
                                                           5' (SEQ ID NO: 6)
                                                           5' (SEQ ID NO: 7)
                                                           5' (SEQ ID NO: 8)
                                                           5' (SEQ ID NO: 9)
                                                           5' (SEQ ID NO: 10)
                                                           5' (SEQ ID NO: 11)
                                                           5' (SEQ ID NO: 12)

1A Probe          FAM
                              ↓
                    ACCGGTGACATTTACCTGCTCAACCTGGCC  - 3'
                  TGGCCACTGTAAATGGACGAGTTGGACCGGGACGT  -
                  TGGCCACTGTAAATGGACGAGTTGGACCGCGACGT  -
                  TGGCCACTGTAAATGGACGAGTTGGACACCCGACGT -
                  TGGCCACTGTAAATGGACGAGTTGGACGCCGACGT  -
                  TGGCCACTGTAAATGGACGAGTTGGAGGCCGACGT  -
                  TGGCCACTGTAAATGGACGAGTTGGTGGCCGACGT  -
                  TGGCCACTGTAAATGGACGAGTTGCTGGCCGACGT  -
                  TGGCCACTGTAAATGGACGAGTTCCTGGCCGACGT  -
                                                    ↑
                                          Mismatched bases to
                                       generate 3' flap in probe 1A
           BHQ2
CCR2 Pfu Exo Target 1:   3' - P03 -
CCR2 Pfu Exo Target 2:   3' - P03 -
CCR2 Pfu Exo Target 3:   3' - P03 -
CCR2 Pfu Exo Target 4:   3' - P03 -
CCR2 Pfu Exo Target 5:   3' - P03 -
CCR2 Pfu Exo Target 6:   3' - P03 -
CCR2 Pfu Exo Target 7:   3' - P03 -
CCR2 Pfu Exo Target 8:   3' - P03 -
```

*FIG. 2A*

| Oligo Name | Modifications | Sequence 5' - 3' |
|---|---|---|
| CCR2_ExoV1_3'Fam7-0 | Fam 3'OH | ATGACTGACATTTACCTGCTCAACCTGG (SEQ ID NO:13) |
| CCR2_ExoV1_3'Fam7-1 | Fam 3'OH | ATGACTGACATTTACCTGCTCAACCTGA (SEQ ID NO:14) |
| CCR2_1A_Exo V1_3'Fam7 | Fam 3'OH | ATGACTGACATTTACCTGCTCAACCTGGAG (SEQ ID NO:15) |
| CCR2_ExoV1_3'Fam7-3 | Fam 3'OH | ATGACTGACATTTACCTGCTCAACCTGGAGG (SEQ ID NO:16) |
| CCR2_ExoV1_3'Fam7-4 | Fam 3'OH | ATGACTGACATTTACCTGCTCAACCTGGAGGA (SEQ ID NO:17) |
| CCR2_ExoV1_3'Fam7-5 | Fam 3'OH | ATGACTGACATTTACCTGCTCAACCTGGAGGAG (SEQ ID NO:18) |
| CCR2_Exo V1_QC_3'flap1 | 5'BHQ2; C3 | GGTTGAGCAGGTAAATGTCAGTCATCTGTA (SEQ ID NO:19) |
| CCR2 3Nuc Target 4Q | internal BHQ, PO3 on 3' end | CAG(T-BHQ)GGAGGGCCAGGTTGAGCAGGTAAATGTCACCGGT (SEQ ID NO:20) |

FIG. 2B

```
                                    CCR2_1A_Exo V1_3'Fam8
                                    CCR2 Target Amplicon
            A
5' -  /TGACTGACATTTACCTGCTCAACCTGG    GA - FAM - 3'
    T/                                          (SEQ ID NO:29)
3' -- AACTGACTGTAAATGGACGAGTTGGACCGGTAGAGA - 5' (SEQ ID NO:21)
```

| Oligos | Modification(s) | Sequence 5' – 3' |
|---|---|---|
| CCR2_1A_Exo V1_3'Fam | Fam 3'OH | ATGACTGACATTTACCTGCTCAACCTGGGG (SEQ ID NO:22) |
| CCR2_1A_Exo V1_3'Fam2 | Fam 3'OH | ATGACTGACATTTACCTGCTCAACCTGGTG (SEQ ID NO:23) |
| CCR2_1A_Exo V1_3'Fam3 | Fam 3'OH | ATGACTGACATTTACCTGCTCAACCTGGAA (SEQ ID NO:24) |
| CCR2_1A_Exo V1_3'Fam4 | Fam 3'OH | ATGACTGACATTTACCTGCTCAACCTGGTT (SEQ ID NO:25) |
| CCR2_1A_Exo V1_3'Fam5 | Fam 3'OH | ATGACTGACATTTACCTGCTCAACCTGGTA (SEQ ID NO:26) |
| CCR2_1A_Exo V1_3'Fam6 | Fam 3'OH | ATGACTGACATTTACCTGCTCAACCTGGAT (SEQ ID NO:27) |
| CCR2_1A_Exo V1_3'Fam7 | Fam 3'OH | ATGACTGACATTTACCTGCTCAACCTGGAG (SEQ ID NO:28) |
| CCR2_1A_Exo V1_3'Fam8 | Fam 3'OH | ATGACTGACATTTACCTGCTCAACCTGGGA (SEQ ID NO:29) |
| CCR2_1A_Exo V1_3'Fam9 | Fam 3'OH | ATGACTGACATTTACCTGCTCAACCTGGGT (SEQ ID NO:30) |
| CCR2_1A_Exo V1_3'Fam10 | Fam 3'OH | ATGACTGACATTTACCTGCTCAACCTGGCC (SEQ ID NO:31) |
| CCR2_1A_Exo V1_3'Fam11 | Fam 3'OH | ATGACTGACATTTACCTGCTCAACCTGGGC (SEQ ID NO:32) |
| CCR2_1A_Exo V1_3'Fam12 | Fam 3'OH | ATGACTGACATTTACCTGCTCAACCTGGTC (SEQ ID NO:33) |
| CCR2_1A_Exo V1_3'Fam13 | Fam 3'OH | ATGACTGACATTTACCTGCTCAACCTGGAC (SEQ ID NO:34) |
| CCR2_1A_Exo V1_3'Fam14 | Fam 3'OH | ATGACTGACATTTACCTGCTCAACCTGGCG (SEQ ID NO:35) |
| CCR2_1A_Exo V1_3'Fam15 | Fam 3'OH | ATGACTGACATTTACCTGCTCAACCTGGCT (SEQ ID NO:36) |
| CCR2_1A_Exo V1_3'Fam16 | Fam 3'OH | ATGACTGACATTTACCTGCTCAACCTGGCA (SEQ ID NO:37) |
| CCR2 3'Nuc Target 1Q | 3' phosphate, internal BHQ2 | CAG(T-BHQ)GCAGAACCAGGTTGAGCAGGTAAATGTCACCGGT (SEQ ID NO:38) |
| CCR2 3'Nuc Target 2Q | 3' phosphate, internal BHQ2 | CAG(T-BHQ)GCAGCACCAGGTTGAGCAGGTAAATGTCACCGGT (SEQ ID NO:5) |
| CCR2 3'Nuc Target 3Q | 3' phosphate, internal BHQ2 | CAG(T-BHQ)GCAGATCCAGGTTGAGCAGGTAAATGTCACCGGT (SEQ ID NO:39) |
| CCR2 3'Nuc Target 4Q | 3' phosphate, internal BHQ2 | CAG(T-BHQ)GCAGGGCCAGGTTGAGCAGGTAAATGTCACCGGT (SEQ ID NO:40) |
| CCR2 Pfu Exo Target 1 | 3' PO3 | TGCAGGGCCAGGTTGAGCAGGTAAATGTCACCGGT (SEQ ID NO:41) |

FIG. 5

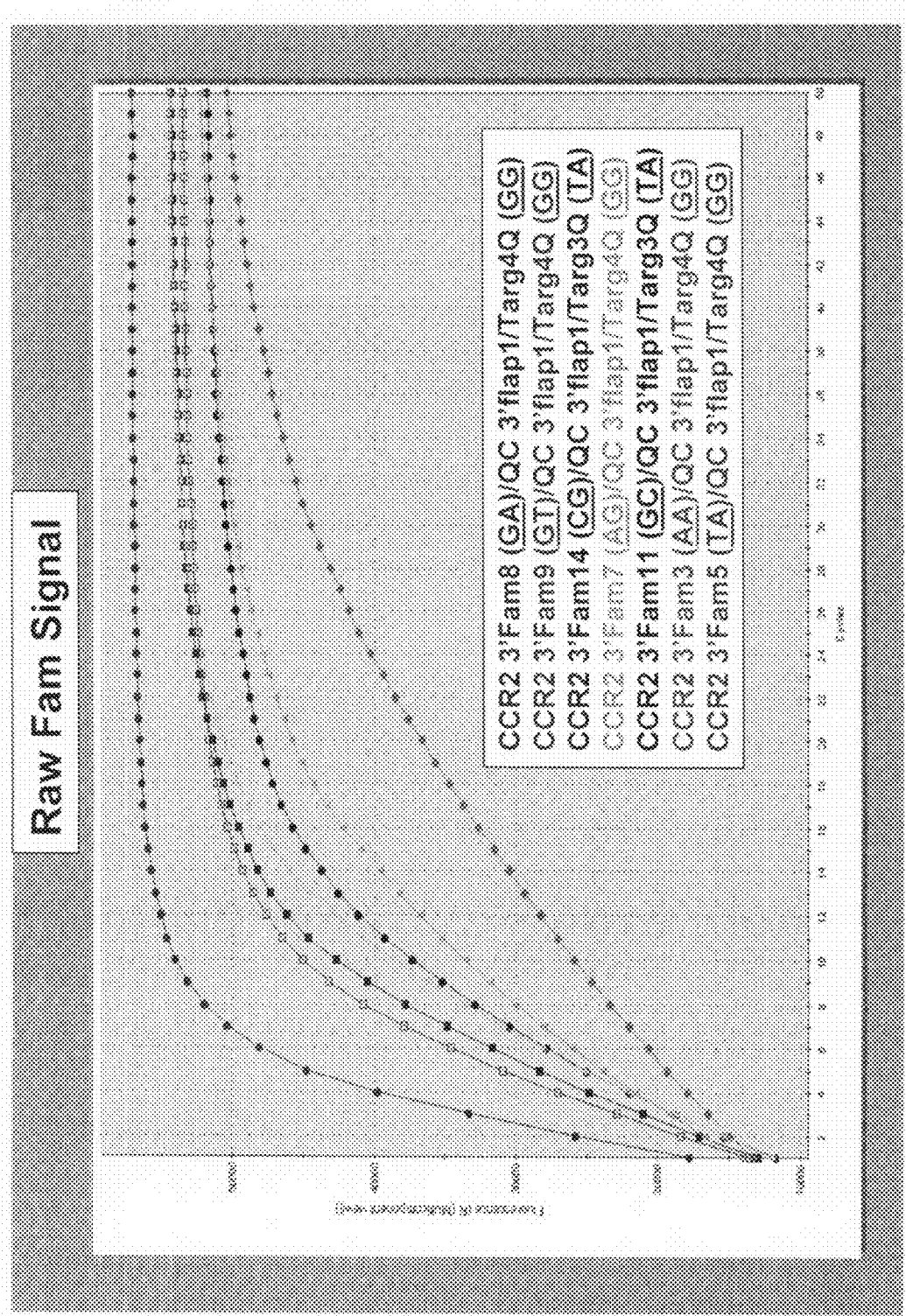
Figure 6. Comparing Most Efficiently Cleaved CCR2 3'Fam Oligos

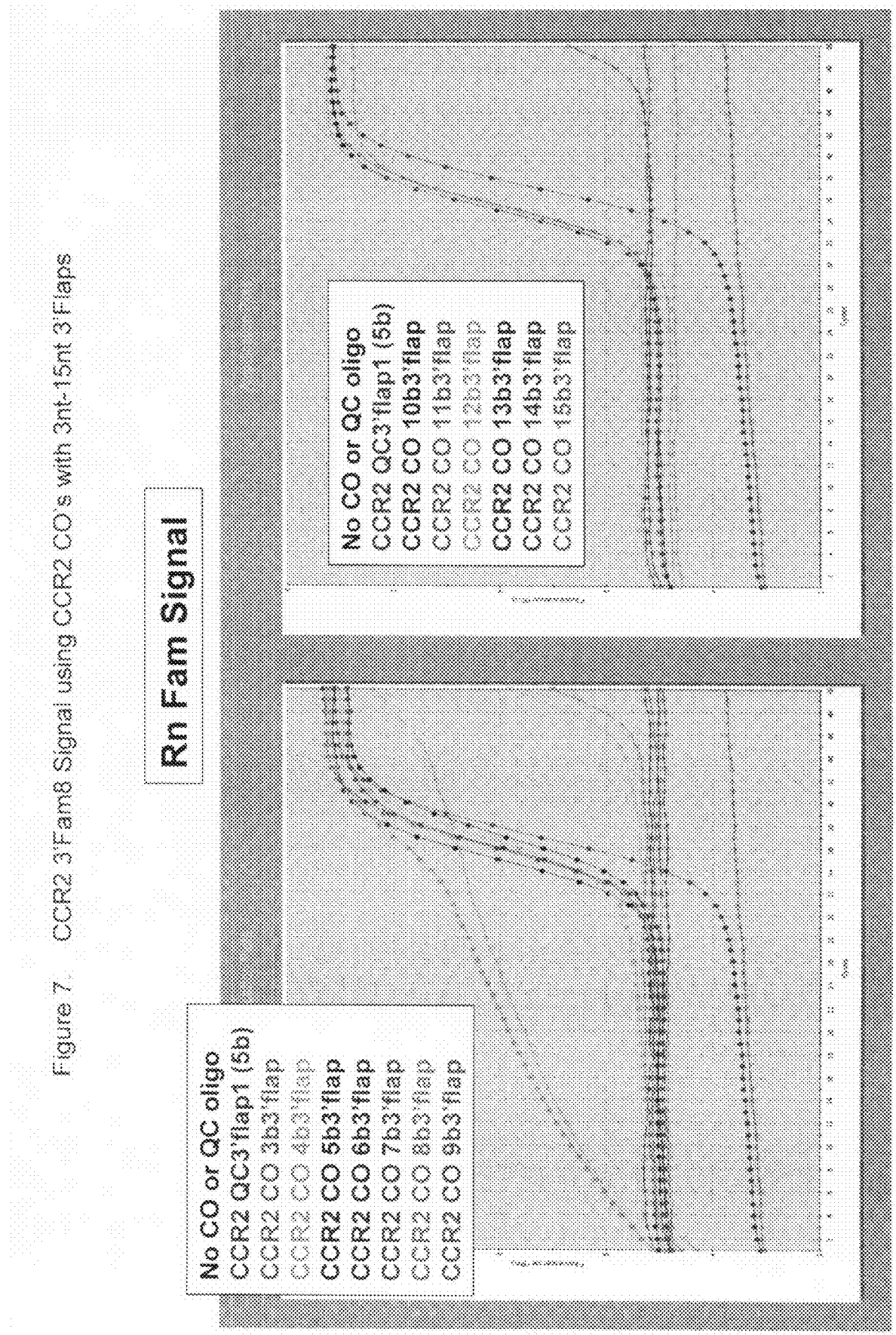
Figure 7. CCR2 3'Fam8 Signal using CCR2 CO's with 3nt-15nt 3'Flaps

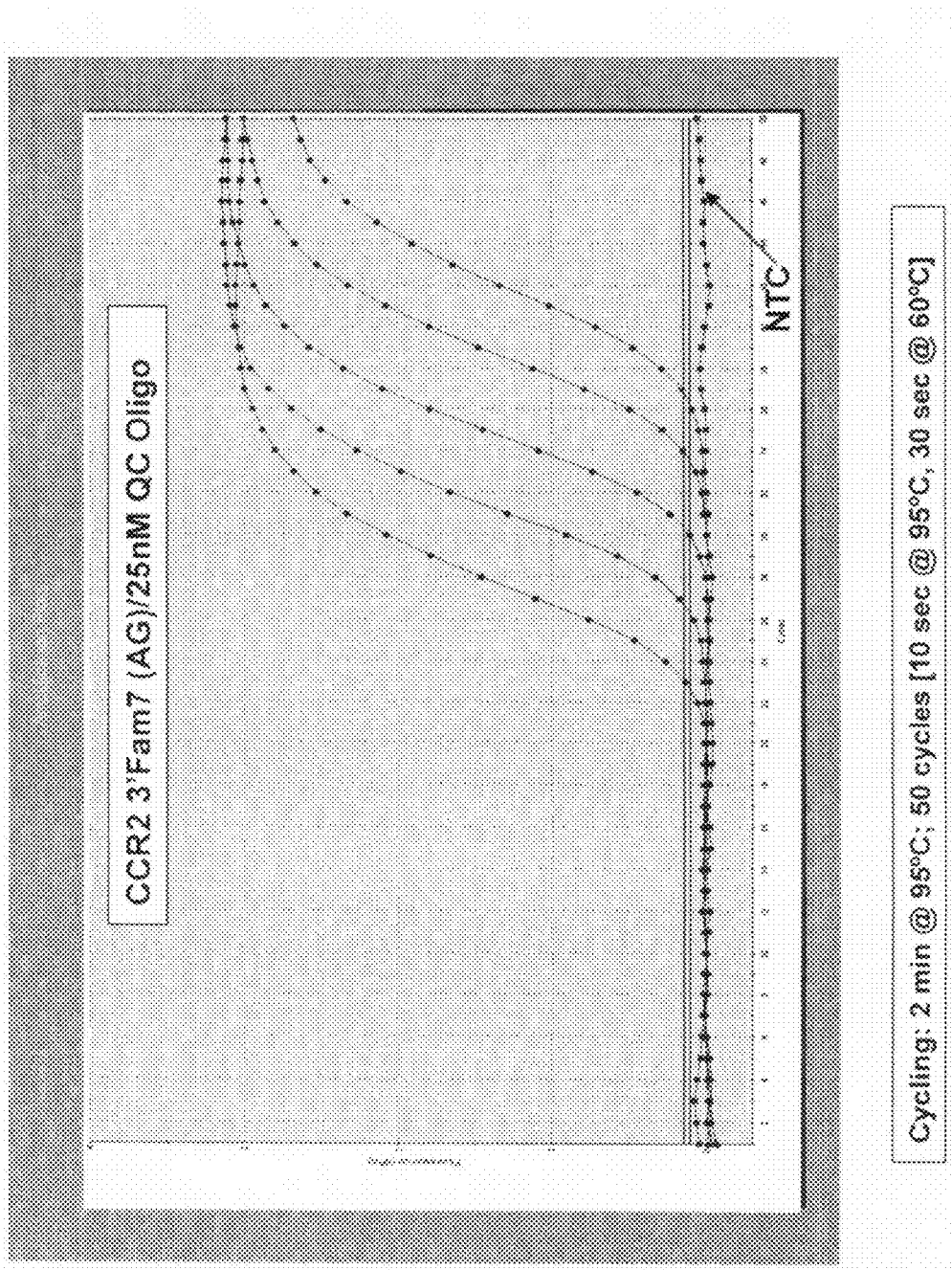
Figure 8. CCR2 3'Fam7 Standard Curves

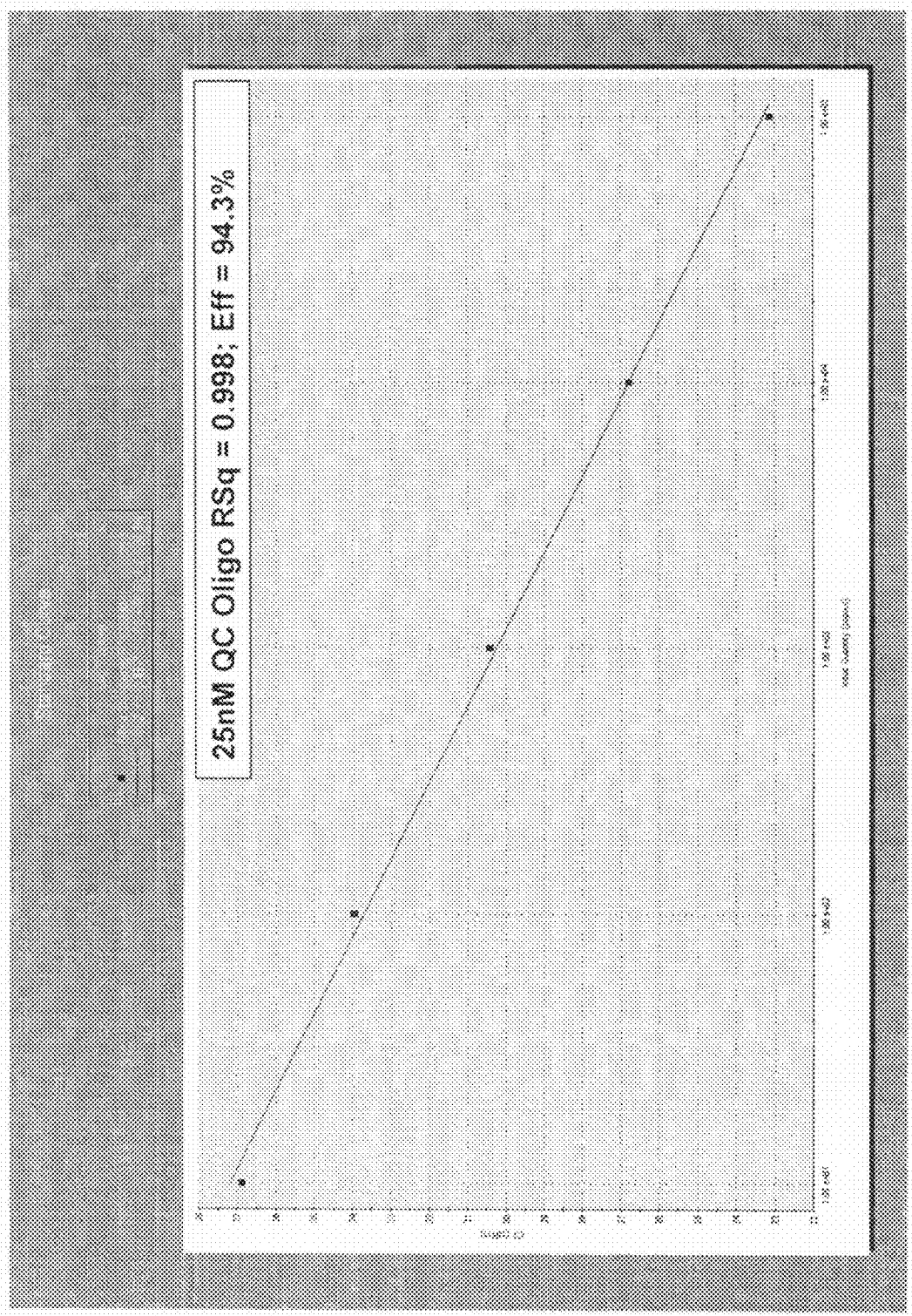
Figure 9. CCR2 3'Fam7 Standard Curve

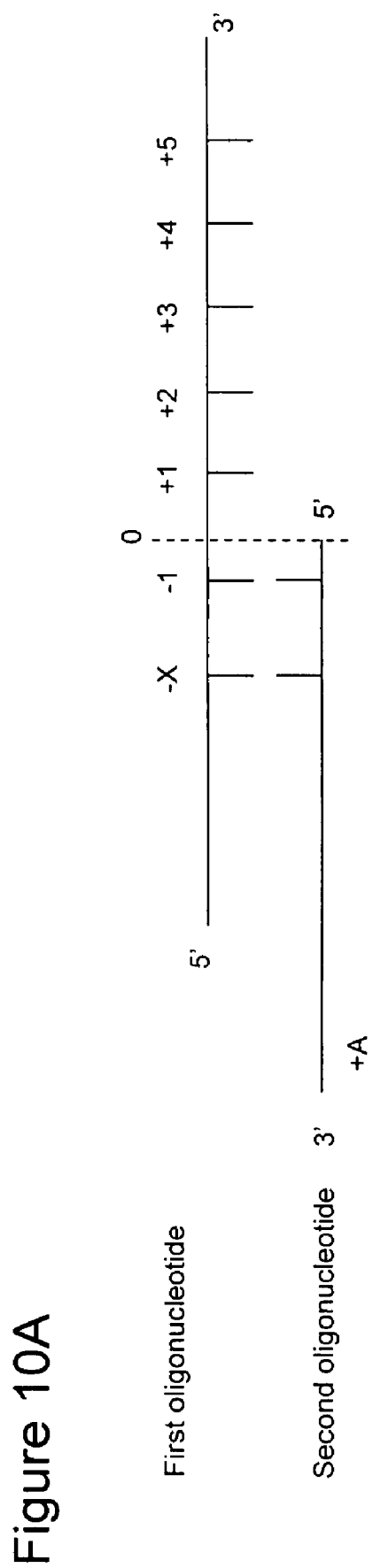

| Oligo Name | Modifications | Sequence 5' – 3' |
|---|---|---|
| CCR2_ExoV1_QC_3'flap 1 | 5'BHQ; C3 | GGTTGAGCAGGTAAATGTCAGTCATCTCTGTA (SEQ ID NO:42) |
| CCR2_CO_3b3'_noQ | 3'PO3 | CAGGTTGAGCAGGTAAATGTCAGTCATCTG (SEQ ID NO:43) |
| CCR2_CO_4b3'_noQ | 3'PO3 | AGGTTGAGCAGGTAAATGTCAGTCATCTGT (SEQ ID NO:44) |
| CCR2_CO_5b3'_noQ | 3'PO3 | GGTTGAGCAGGTAAATGTCAGTCATCTGTA (SEQ ID NO:45) |
| CCR2_CO_6b3'_noQ | 3'PO3 | GTTGAGCAGGTAAATGTCAGTCATCTGTAA (SEQ ID NO:46) |
| CCR2_CO_7b3'_noQ | 3'PO3 | TTGAGCAGGTAAATGTCAGTCATCTGTAAG (SEQ ID NO:47) |
| CCR2_CO_8b3'_noQ | 3'PO3 | TGAGCAGGTAAATGTCAGTCATCTGTAAGT (SEQ ID NO:48) |
| CCR2_CO_9b3'_noQ | 3'PO3 | GAGCAGGTAAATGTCAGTCATCTGTAAGTC (SEQ ID NO:49) |
| CCR2_CO_10b3'_noQ | 3'PO3 | AGCAGGTAAATGTCAGTCATCTGTAAGTCG (SEQ ID NO:50) |
| CCR2_CO_11b3'_noQ | 3'PO3 | GCAGGTAAATGTCAGTCATCTGTAAGTCGC (SEQ ID NO:51) |
| CCR2_CO_12b3'_noQ | 3'PO3 | CAGGTAAATGTCAGTCATCTGTAAGTCGCA (SEQ ID NO:52) |
| CCR2_CO_13b3'_noQ | 3'PO3 | AGGTAAATGTCAGTCATCTGTAAGTCGCAA (SEQ ID NO:53) |
| CCR2_CO_14b3'_noQ | 3'PO3 | GGTAAATGTCAGTCATCTGTAAGTCGCAAA (SEQ ID NO:54) |
| CCR2_CO_15b3'_noQ | 3'PO3 | GTAAATGTCAGTCATCTGTAAGTCGCAAAC (SEQ ID NO:55) |
| CCR2_1A_ExoV1_3'Fam8 | Fam 3'OH | ATGACTGACATTTACCTGCTCAACCTGGGA (SEQ ID NO:56) |
| CCR2_R_199 | none | TCATTTGCAGCAGAGTGAGC (SEQ ID NO:57) |

*FIG. 11*

SEQUENCE LISTING

```
<160> NUMBER OF SEQ ID NOS: 57

<210> SEQ ID NO 1
<211> LENGTH: 30
<212> TYPE: DNA
<213> ORGANISM: Artificial
<220> FEATURE:
<223> OTHER INFORMATION: Synthetic quenching probe

<400> SEQUENCE: 1
ggttgagcag gtaaatgtca gtcatctgta                                       30

<210> SEQ ID NO 2
<211> LENGTH: 20
<212> TYPE: DNA
<213> ORGANISM: Artificial
<220> FEATURE:
<223> OTHER INFORMATION: synthetic primer

<400> SEQUENCE: 2
tcatttgcag cagagtgagc                                                  20

<210> SEQ ID NO 3
<211> LENGTH: 20
<212> TYPE: DNA
<213> ORGANISM: Artificial
<220> FEATURE:
<223> OTHER INFORMATION: Synthetic primer

<400> SEQUENCE: 3
```
tcatttgcag cagagtgagc                                               20

<210> SEQ ID NO 4
<211> LENGTH: 30
<212> TYPE: DNA
<213> ORGANISM: Artificial
<220> FEATURE:
<223> OTHER INFORMATION: Synthetic probe

<400> SEQUENCE: 4
accggtgaca tttacctgct caacctggcc                                    30

<210> SEQ ID NO 5
<211> LENGTH: 35
<212> TYPE: DNA
<213> ORGANISM: Artificial
<220> FEATURE:
<223> OTHER INFORMATION: Synthetic target

<400> SEQUENCE: 5
tggccactgt aaatggacga gttggaccgg gacgt                              35

<210> SEQ ID NO 6
<211> LENGTH: 35
<212> TYPE: DNA
<213> ORGANISM: Artificial
<220> FEATURE:
<223> OTHER INFORMATION: Synthetic target

<400> SEQUENCE: 6
tggccactgt aaatggacga gttggaccgc gacgt                              35

<210> SEQ ID NO 7
<211> LENGTH: 35
<212> TYPE: DNA
<213> ORGANISM: Artificial
<220> FEATURE:
<223> OTHER INFORMATION: Synthetic target

<400> SEQUENCE: 7
tggccactgt aaatggacga gttggacccc gacgt                              35

<210> SEQ ID NO 8
<211> LENGTH: 35
<212> TYPE: DNA
<213> ORGANISM: Artificial
<220> FEATURE:
<223> OTHER INFORMATION: Synthetic target

<400> SEQUENCE: 8
tggccactgt aaatggacga gttggacgcc gacgt                              35

<210> SEQ ID NO 9
<211> LENGTH: 35
<212> TYPE: DNA
<213> ORGANISM: Artificial
<220> FEATURE:
<223> OTHER INFORMATION: Synthetic target

<400> SEQUENCE: 9
tggccactgt aaatggacga gttggaggcc gacgt                              35

<210> SEQ ID NO 10
<211> LENGTH: 35
<212> TYPE: DNA

```
<213> ORGANISM: Artificial
<220> FEATURE:
<223> OTHER INFORMATION: Synthetic target

<400> SEQUENCE: 10
tggccactgt aaatggacga gttggtggcc gacgt                                35

<210> SEQ ID NO 11
<211> LENGTH: 35
<212> TYPE: DNA
<213> ORGANISM: Artificial
<220> FEATURE:
<223> OTHER INFORMATION: Synthetic target

<400> SEQUENCE: 11
tggccactgt aaatggacga gttgctggcc gacgt                                35

<210> SEQ ID NO 12
<211> LENGTH: 35
<212> TYPE: DNA
<213> ORGANISM: Artificial
<220> FEATURE:
<223> OTHER INFORMATION: Synthetic target

<400> SEQUENCE: 12
tggccactgt aaatggacga gttcctggcc gacgt                                35

<210> SEQ ID NO 13
<211> LENGTH: 28
<212> TYPE: DNA
<213> ORGANISM: Artificial
<220> FEATURE:
<223> OTHER INFORMATION: Synthetic probe

<400> SEQUENCE: 13
atgactgaca tttacctgct caacctgg                                        28

<210> SEQ ID NO 14
<211> LENGTH: 29
<212> TYPE: DNA
<213> ORGANISM: Artificial
<220> FEATURE:
<223> OTHER INFORMATION: Synthetic probe

<400> SEQUENCE: 14
atgactgaca tttacctgct caacctgga                                       29

<210> SEQ ID NO 15
<211> LENGTH: 30
<212> TYPE: DNA
<213> ORGANISM: Artificial
<220> FEATURE:
<223> OTHER INFORMATION: Synthetic probe

<400> SEQUENCE: 15
atgactgaca tttacctgct caacctggag                                      30

<210> SEQ ID NO 16
<211> LENGTH: 31
<212> TYPE: DNA
<213> ORGANISM: Artificial
<220> FEATURE:
<223> OTHER INFORMATION: Synthetic probe

<400> SEQUENCE: 16
atgactgaca tttacctgct caacctggag g                                    31
```

<210> SEQ ID NO 17
<211> LENGTH: 32
<212> TYPE: DNA
<213> ORGANISM: Artificial
<220> FEATURE:
<223> OTHER INFORMATION: Synthetic probe

<400> SEQUENCE: 17
atgactgaca tttacctgct caacctggag ga                                    32

<210> SEQ ID NO 18
<211> LENGTH: 33
<212> TYPE: DNA
<213> ORGANISM: Artificial
<220> FEATURE:
<223> OTHER INFORMATION: Synthetic probe

<400> SEQUENCE: 18
atgactgaca tttacctgct caacctggag gag                                   33

<210> SEQ ID NO 19
<211> LENGTH: 30
<212> TYPE: DNA
<213> ORGANISM: Artificial
<220> FEATURE:
<223> OTHER INFORMATION: Synthetic probe

<400> SEQUENCE: 19
ggttgagcag gtaaatgtca gtcatctgta                                       30

<210> SEQ ID NO 20
<211> LENGTH: 38
<212> TYPE: DNA
<213> ORGANISM: Artificial
<220> FEATURE:
<223> OTHER INFORMATION: Synthetic target

<400> SEQUENCE: 20
cagtggaggg ccaggttgag caggtaaatg tcaccggt                              38

<210> SEQ ID NO 21
<211> LENGTH: 36
<212> TYPE: DNA
<213> ORGANISM: Artificial
<220> FEATURE:
<223> OTHER INFORMATION: Synthetic target

<400> SEQUENCE: 21
aactgactgt aaatggacga gttggaccgg tagaga                                36

<210> SEQ ID NO 22
<211> LENGTH: 30
<212> TYPE: DNA
<213> ORGANISM: Artificial
<220> FEATURE:
<223> OTHER INFORMATION: syntehtic probe

<400> SEQUENCE: 22
atgactgaca tttacctgct caacctgggg                                       30

<210> SEQ ID NO 23
<211> LENGTH: 30
<212> TYPE: DNA
<213> ORGANISM: Artificial
<220> FEATURE:

```
<223> OTHER INFORMATION: synthetic probe

<400> SEQUENCE: 23
atgactgaca tttacctgct caacctggtg                                    30

<210> SEQ ID NO 24
<211> LENGTH: 30
<212> TYPE: DNA
<213> ORGANISM: Artificial
<220> FEATURE:
<223> OTHER INFORMATION: synthetic probe

<400> SEQUENCE: 24
atgactgaca tttacctgct caacctggaa                                    30

<210> SEQ ID NO 25
<211> LENGTH: 30
<212> TYPE: DNA
<213> ORGANISM: Artificial
<220> FEATURE:
<223> OTHER INFORMATION: synthetic probe

<400> SEQUENCE: 25
atgactgaca tttacctgct caacctggtt                                    30

<210> SEQ ID NO 26
<211> LENGTH: 30
<212> TYPE: DNA
<213> ORGANISM: Artificial
<220> FEATURE:
<223> OTHER INFORMATION: synthetic probe

<400> SEQUENCE: 26
atgactgaca tttacctgct caacctggta                                    30

<210> SEQ ID NO 27
<211> LENGTH: 30
<212> TYPE: DNA
<213> ORGANISM: Artificial
<220> FEATURE:
<223> OTHER INFORMATION: synthetic probe

<400> SEQUENCE: 27
atgactgaca tttacctgct caacctggat                                    30

<210> SEQ ID NO 28
<211> LENGTH: 30
<212> TYPE: DNA
<213> ORGANISM: Artificial
<220> FEATURE:
<223> OTHER INFORMATION: synthetic probe

<400> SEQUENCE: 28
atgactgaca tttacctgct caacctggag                                    30

<210> SEQ ID NO 29
<211> LENGTH: 30
<212> TYPE: DNA
<213> ORGANISM: Artificial
<220> FEATURE:
<223> OTHER INFORMATION: synthetic target

<400> SEQUENCE: 29
atgactgaca tttacctgct caacctggga                                    30
```

```
<210> SEQ ID NO 30
<211> LENGTH: 30
<212> TYPE: DNA
<213> ORGANISM: Artificial
<220> FEATURE:
<223> OTHER INFORMATION: synthetic target

<400> SEQUENCE: 30
atgactgaca tttacctgct caacctgggt                                    30

<210> SEQ ID NO 31
<211> LENGTH: 30
<212> TYPE: DNA
<213> ORGANISM: Artificial
<220> FEATURE:
<223> OTHER INFORMATION: synthetic target

<400> SEQUENCE: 31
atgactgaca tttacctgct caacctggcc                                    30

<210> SEQ ID NO 32
<211> LENGTH: 30
<212> TYPE: DNA
<213> ORGANISM: Artificial
<220> FEATURE:
<223> OTHER INFORMATION: synthetic target

<400> SEQUENCE: 32
atgactgaca tttacctgct caacctgggc                                    30

<210> SEQ ID NO 33
<211> LENGTH: 30
<212> TYPE: DNA
<213> ORGANISM: Artificial
<220> FEATURE:
<223> OTHER INFORMATION: synthetic target

<400> SEQUENCE: 33
atgactgaca tttacctgct caacctggtc                                    30

<210> SEQ ID NO 34
<211> LENGTH: 30
<212> TYPE: DNA
<213> ORGANISM: Artificial
<220> FEATURE:
<223> OTHER INFORMATION: synthetic target

<400> SEQUENCE: 34
atgactgaca tttacctgct caacctggac                                    30

<210> SEQ ID NO 35
<211> LENGTH: 30
<212> TYPE: DNA
<213> ORGANISM: Artificial
<220> FEATURE:
<223> OTHER INFORMATION: synthetic target

<400> SEQUENCE: 35
atgactgaca tttacctgct caacctggcg                                    30

<210> SEQ ID NO 36
<211> LENGTH: 30
<212> TYPE: DNA
<213> ORGANISM: Artificial
<220> FEATURE:
<223> OTHER INFORMATION: synthetic probe
```

```
<400> SEQUENCE: 36
atgactgaca tttacctgct caacctggct                                    30

<210> SEQ ID NO 37
<211> LENGTH: 30
<212> TYPE: DNA
<213> ORGANISM: Artificial
<220> FEATURE:
<223> OTHER INFORMATION: syntehtic probe

<400> SEQUENCE: 37
atgactgaca tttacctgct caacctggca                                    30

<210> SEQ ID NO 38
<211> LENGTH: 38
<212> TYPE: DNA
<213> ORGANISM: Artificial
<220> FEATURE:
<223> OTHER INFORMATION: synthetic target

<400> SEQUENCE: 38
cagtgcagaa ccaggttgag caggtaaatg tcaccggt                           38

<210> SEQ ID NO 39
<211> LENGTH: 38
<212> TYPE: DNA
<213> ORGANISM: Artificial
<220> FEATURE:
<223> OTHER INFORMATION: synthetic target

<400> SEQUENCE: 39
cagtgcagat ccaggttgag caggtaaatg tcaccggt                           38

<210> SEQ ID NO 40
<211> LENGTH: 38
<212> TYPE: DNA
<213> ORGANISM: Artificial
<220> FEATURE:
<223> OTHER INFORMATION: synthetic target

<400> SEQUENCE: 40
cagtgcaggg ccaggttgag caggtaaatg tcaccggt                           38

<210> SEQ ID NO 41
<211> LENGTH: 35
<212> TYPE: DNA
<213> ORGANISM: Artificial
<220> FEATURE:
<223> OTHER INFORMATION: synthetic target

<400> SEQUENCE: 41
tgcagggcca ggttgagcag gtaaatgtca ccggt                              35

<210> SEQ ID NO 42
<211> LENGTH: 30
<212> TYPE: DNA
<213> ORGANISM: Artificial
<220> FEATURE:
<223> OTHER INFORMATION: sythetic probe

<400> SEQUENCE: 42
ggttgagcag gtaaatgtca gtcatctgta                                    30

<210> SEQ ID NO 43
<211> LENGTH: 30
```

```
<212> TYPE: DNA
<213> ORGANISM: Artificial
<220> FEATURE:
<223> OTHER INFORMATION: synthetic probe

<400> SEQUENCE: 43
caggttgagc aggtaaatgt cagtcatctg                                          30

<210> SEQ ID NO 44
<211> LENGTH: 30
<212> TYPE: DNA
<213> ORGANISM: Artificial
<220> FEATURE:
<223> OTHER INFORMATION: synthetic probe

<400> SEQUENCE: 44
aggttgagca ggtaaatgtc agtcatctgt                                          30

<210> SEQ ID NO 45
<211> LENGTH: 30
<212> TYPE: DNA
<213> ORGANISM: Artificial
<220> FEATURE:
<223> OTHER INFORMATION: synthetic probe

<400> SEQUENCE: 45
ggttgagcag gtaaatgtca gtcatctgta                                          30

<210> SEQ ID NO 46
<211> LENGTH: 30
<212> TYPE: DNA
<213> ORGANISM: Artificial
<220> FEATURE:
<223> OTHER INFORMATION: synthetic probe

<400> SEQUENCE: 46
gttgagcagg taaatgtcag tcatctgtaa                                          30

<210> SEQ ID NO 47
<211> LENGTH: 30
<212> TYPE: DNA
<213> ORGANISM: Artificial
<220> FEATURE:
<223> OTHER INFORMATION: synthetic probe

<400> SEQUENCE: 47
ttgagcaggt aaatgtcagt catctgtaag                                          30

<210> SEQ ID NO 48
<211> LENGTH: 30
<212> TYPE: DNA
<213> ORGANISM: Artificial
<220> FEATURE:
<223> OTHER INFORMATION: synthetic probe

<400> SEQUENCE: 48
tgagcaggta aatgtcagtc atctgtaagt                                          30

<210> SEQ ID NO 49
<211> LENGTH: 30
<212> TYPE: DNA
<213> ORGANISM: Artificial
<220> FEATURE:
<223> OTHER INFORMATION: synthetic probe

<400> SEQUENCE: 49
```
gagcaggtaa atgtcagtca tctgtaagtc                                    30

<210> SEQ ID NO 50
<211> LENGTH: 30
<212> TYPE: DNA
<213> ORGANISM: Artificial
<220> FEATURE:
<223> OTHER INFORMATION: synthetic probe

<400> SEQUENCE: 50
agcaggtaaa tgtcagtcat ctgtaagtcg                                    30

<210> SEQ ID NO 51
<211> LENGTH: 30
<212> TYPE: DNA
<213> ORGANISM: Artificial
<220> FEATURE:
<223> OTHER INFORMATION: synthetic probe

<400> SEQUENCE: 51
gcaggtaaat gtcagtcatc tgtaagtcgc                                    30

<210> SEQ ID NO 52
<211> LENGTH: 30
<212> TYPE: DNA
<213> ORGANISM: Artificial
<220> FEATURE:
<223> OTHER INFORMATION: synthetic probe

<400> SEQUENCE: 52
caggtaaatg tcagtcatct gtaagtcgca                                    30

<210> SEQ ID NO 53
<211> LENGTH: 30
<212> TYPE: DNA
<213> ORGANISM: Artificial
<220> FEATURE:
<223> OTHER INFORMATION: synthetic probe

<400> SEQUENCE: 53
aggtaaatgt cagtcatctg taagtcgcaa                                    30

<210> SEQ ID NO 54
<211> LENGTH: 30
<212> TYPE: DNA
<213> ORGANISM: Artificial
<220> FEATURE:
<223> OTHER INFORMATION: synthetic probe

<400> SEQUENCE: 54
ggtaaatgtc agtcatctgt aagtcgcaaa                                    30

<210> SEQ ID NO 55
<211> LENGTH: 30
<212> TYPE: DNA
<213> ORGANISM: Artificial
<220> FEATURE:
<223> OTHER INFORMATION: synthetic probe

<400> SEQUENCE: 55
gtaaatgtca gtcatctgta agtcgcaaac                                    30

<210> SEQ ID NO 56
<211> LENGTH: 30
<212> TYPE: DNA
<213> ORGANISM: Artificial

```
-continued

<220> FEATURE:
<223> OTHER INFORMATION: synthetic probe

<400> SEQUENCE: 56
atgactgaca tttacctgct caacctggga                                    30

<210> SEQ ID NO 57
<211> LENGTH: 20
<212> TYPE: DNA
<213> ORGANISM: Artificial
<220> FEATURE:
<223> OTHER INFORMATION: synthetic probe

<400> SEQUENCE: 57
tcatttgcag cagagtgagc                                               20
```

METHODS AND COMPOSITIONS FOR DETECTION OF A TARGET NUCLEIC ACID SEQUENCE UTILIZING A PROBE WITH A 3' FLAP

RELATED APPLICATIONS

This application is a continuation-in-part of U.S. patent application Ser. No. 11/473,678, filed Jun. 22, 2006, which is a continuation in part of U.S. patent application Ser. No. 09/728,574 filed Nov. 30, 2000, which is a continuation-in-part of U.S. patent application Ser. No. 09/650,888 filed Aug. 30, 2000 (now U.S. Pat. No. 6,548,250), which is a continuation-in-part of U.S. patent application Ser. No. 09/430,692 filed Oct. 29, 1999 (now U.S. Pat. No. 6,528,254), the entireties of which are incorporated herein by reference.

BACKGROUND

Techniques for polynucleotide detection have found widespread use in basic research, diagnostics, and forensics. Polynucleotide detection can be accomplished by a number of methods. Most methods rely on the use of the polymerase chain reaction (PCR) to amplify the amount of target DNA.

U.S. Pat. Nos. 5,843,669, 5,719,028, 5,837,450, 5,846,717 and 5,888,780 disclose a method of cleaving a target DNA molecule by incubating a 5' labeled target DNA with a DNA polymerase isolated from *Thermus aquaticus* (Taq polymerase) and a partially complementary oligonucleotide capable of hybridizing to sequences at the desired point of cleavage. The partially complementary oligonucleotide directs the Taq polymerase to the target DNA through formation of a substrate structure containing a duplex with a 3' extension opposite the desired site of cleavage wherein the non-complementary region of the oligonucleotide provides a 3' arm and the unannealed 5' region of the substrate molecule provides a 5' arm. The partially complementary oligonucleotide includes a 3' nucleotide extension capable of forming a short hairpin. The release of labeled fragment is detected following cleavage by Taq polymerase.

U.S. Pat. Nos. 5,843,669, 5,719,028, 5,837,450, 5,846,717 and 5,888,780 disclose the generation of mutant, thermostable DNA polymerases that have very little or no detectable synthetic activity, and wild type thermostable nuclease activity. The mutant polymerases are said to be useful because they lack 5' to 3' synthetic activity; thus synthetic activity is an undesirable side reaction in combination with a DNA cleavage step in a detection assay.

U.S. Pat. Nos. 5,843,669, 5,719,028, 5,837,450, 5,846,717 and 5,888,780 disclose that wild type Taq polymerase or mutant Taq polymerases that lack synthetic activity can release a labeled fragment by cleaving a 5' end labeled hairpin structure formed by heat denaturation followed by cooling, in the presence of a primer that binds to the 3' arm of the hairpin structure. Further, U.S. Pat. Nos. 5,843,669, 5,719,028, 5,837,450, 5,846,717 and 5,888,780 teach that the mutant Taq polymerases lacking synthetic activity can also cleave this hairpin structure in the absence of a primer that binds to the 3' arm of the hairpin structure.

U.S. Pat. Nos. 5,843,669, 5,719,028, 5,837,450, 5,846,717 and 5,888,780 also disclose that cleavage of this hairpin structure in the presence of a primer that binds to the 3' arm of the hairpin structure by mutant Taq polymerases lacking synthetic activity yields a single species of labeled cleaved product, while wild type Taq polymerase produces multiple cleavage products and converts the hairpin structure to a double stranded form in the presence of dNTPs, due to the high level of synthetic activity of the wild type Taq enzyme.

U.S. Pat. Nos. 5,843,669, 5,719,028, 5,837,450, 5,846,717 and 5,888,780 also disclose that mutant Taq polymerases exhibiting reduced synthetic activity, but not wild type Taq polymerase, can release a single labeled fragment by cleaving a linear nucleic acid substrate comprising a 5' end labeled target nucleic acid and a complementary oligonucleotide wherein the complementary oligonucleotide hybridizes to a portion of the target nucleic acid such that 5' and 3' regions of the target nucleic acid are not annealed to the oligonucleotide and remain single stranded.

U.S. Pat. Nos. 5,843,669, 5,719,028, 5,837,450, 5,846,717 and 5,888,780 also disclose a method of cleaving a labeled nucleic acid substrate at naturally occurring areas of secondary structure. According to this method, biotin labeled DNA substrates are prepared by PCR, mixed with wild type Taq polymerase or CleavaseBN (a mutant Taq polymerase with reduced synthetic activity and wild type 5' to 3' nuclease activity), incubated at 95° C. for 5 seconds to denature the substrate and then quickly cooled to 65° C. to allow the DNA to assume its unique secondary structure by allowing the formation of intra-strand hydrogen bonds between the complementary bases. The reaction mixture is incubated at 65° C. to allow cleavage to occur and biotinylated cleavage products are detected.

Lyamichev et al. disclose a method for detecting DNAs wherein overlapping pairs of oligonucleotide probes that are partially complementary to a region of target DNA are mixed with the target DNA to form a 5' flap region, and wherein cleavage of the labeled downstream probe by a thermostable FEN-1 nuclease produces a labeled cleavage product. Lyamichev et al. also disclose reaction conditions wherein multiple copies of the downstream oligonucleotide probe can be cleaved for a single target sequence in the absence of temperature cycling, so as to amplify the cleavage signal and allow quantitative detection of target DNA at sub-attomole levels (Lyamichev et al., 1999, *Nat. Biotechnol.*, 17:292).

The polymerase chain reaction (PCR) technique, is disclosed in U.S. Pat. Nos. 4,683,202, 4,683,195 and 4,800,159. In its simplest form, PCR is an in vitro method for the enzymatic synthesis of specific DNA sequences, using two oligonucleotide primers that hybridize to opposite strands and flank the region of interest in the target DNA. A repetitive series of reaction steps involving template denaturation, primer annealing and the extension of the annealed primers by DNA polymerase results in the exponential accumulation of a specific fragment whose termini are defined by the 5' ends of the primers. PCR is reported to be capable of producing a selective enrichment of a specific DNA sequence by a factor of $10^9$. The PCR method is also described in Saiki et al., 1985, *Science,* 230:1350.

U.S. Pat. Nos. 5,210,015 and 5,487,972 disclose a PCR based assay for releasing labeled probe comprising generating a signal during the amplification step of a PCR reaction in the presence of a nucleic acid to be amplified, Taq polymerase that has 5' to 3' exonuclease activity and a 5', 3' or 5' and 3' end-labeled probe comprising a region complementary to the amplified region and an additional non-complementary 5' tail region. U.S. Pat. Nos. 5,210,015 and 5,487,972 disclose further that this PCR based assay can liberate the 5' labeled end of a hybridized probe when the Taq polymerase is positioned near the labeled probe by an upstream probe in a polymerization independent manner, e.g. in the absence of dNTPs.

U.S. Pat. No. 5,391,480 teaches a method of detecting polymorphisms or mutations between different nucleic acid sequences. The method involves labeling the 3' nucleotide in a primer with a fluorescent marker. The primer is hybridized to a DNA sample. If the 3' nucleotide (the query position) of the oligonucleotide is complementary to the corresponding nucleotide in the hybridized DNA, it will be insensitive to nuclease; if there is a mismatch it will be sensitive to nuclease and will be cleaved. The cleaved nucleotides are then detected, e.g., by a decrease in fluorescence polarization (FP).

U.S. Pub. No. 2006/0024695 teaches a method of quantifying an amplification reaction. The method employs a labeled probe, unlabeled primers, a polymerase and an enzyme that has 3' to 5' exonuclease activity.

SUMMARY OF THE INVENTION

The invention provides compositions, kits and methods of generating a signal indicative of the presence of a target nucleic acid sequence in a sample by forming a cleavage structure. The cleavage structure is formed by incubating a sample containing a target nucleic acid with a downstream probe that forms a 3' flap when hybridized to the target. The cleavage structure is cleaved with a 3' nuclease and a detectable signal is produced. The signal is indicative of the presence and/or amount of a target nucleic acid sequence in the sample.

In a first aspect, the invention is directed to compositions for generating a signal that is indicative of the presence of a target nucleic acid in a sample. The composition includes an upstream primer, a 3' nuclease and a downstream probe having a 3' flap.

In another aspect, the invention is directed to an oligonucleotide pair for use in detecting the presence of a target nucleic acid. The oligonucleotide pair includes a first oligonucleotide and a second oligonucleotide (analogous to oligonucleotides AB, and A'*, respectively of FIG. 3). The first oligonucleotide has a 5' region and a 3' region. The 5' region is complementary to the target nucleic acid. The 3' region is non-complementary to the target. A label can be operatively coupled to the 3' region of the first oligonucleotide, preferably the label is a first member of an interactive pair of labels. The label is preferably operatively coupled to the 3' terminal nucleotide of the first oligonucleotide. The second oligonucleotide forms a duplex with said 5' region of said first oligonucleotide under non-denaturing conditions. The second oligonucleotide can also be operatively coupled to a second member of an interactive pair of labels. The first and said second members of the pair of interactive labels interact when the first oligonucleotide and the second oligonucleotide hybridize, and do not interact when said first oligonucleotide and second oligonucleotide dissociate. In addition, it is preferred that when the first and second oligonucleotides are hybridized, at least a 3' nucleotide base of the first oligonucleotide is non-complementary to the second oligonucleotide. It is preferred that one to ten, preferably one to four 3' terminal nucleotides of the first oligonucleotide are non-complementary to the second oligonucleotide and more preferably one to five or more 3' terminal nucleotides are non-complementary to the second oligonucleotide. The oligonucleotide pair may be supplied in a kit.

In another aspect, the invention is directed to a kit for generating a signal that is indicative of the presence of a target nucleic acid in a sample. The kit includes an upstream primer, a 3' nuclease, a probe having a 3' flap and a suitable buffer.

In another aspect, the invention is directed to a method for detecting a target nucleic acid in a sample. The method includes the step of contacting a sample containing the target with a first oligonucleotide, optionally a second oligonucleotide, and 3' nuclease. The first oligonucleotide has a 5' region and a 3' region. The 5' region is complementary to the target nucleic acid and the 3' region is non-complementary to the target. A label can be operatively coupled to the 3' region, and is preferably operatively coupled to the 3' terminal nucleotide of the first oligonucleotide. Preferably the label is a first member of an interactive pair of labels. The second oligonucleotide forms a duplex with said 5' region of said first oligonucleotide under non-denaturing conditions. The second oligonucleotide can also be operatively coupled to a second member of an interactive pair of labels. The first and second members of the interactive pair of labels interact when the first oligonucleotide and the second oligonucleotide form a duplex and do not interact when the first and second oligonucleotides dissociate. When the second oligonucleotide contains a second member of an interactive pair of labels, it is contemplated that a detectable signal is generated upon dissociation of the first oligonucleotide/second oligonucleotide hybrid and competitive duplex formation of the probe with the target. The signal is detected and/or measured and is indicative of the presence and/or amount of the target in the sample. In another aspect, following dissociation of the first and second oligonucleotides, the first oligonucleotide is able to hybridize to the target to form a hybrid, thereby generating a 3' cleavage structure. Cleavage of the 3' cleavage structure generates a detectable signal that is indicative of the presence and/or amount of the target in a sample. In addition, when the first and second oligonucleotides are hybridized, at least a 3' nucleotide base of the first oligonucleotide can be non-complementary to the second oligonucleotide. It is preferred that one to ten, preferably one to four 3' terminal nucleotides of the first oligonucleotide are non-complementary to the second oligonucleotide and more preferably one to five or more 3' terminal nucleotides are non-complementary to the second oligonucleotide.

In yet another aspect, the invention provides a method for detecting a target nucleic acid in a sample. A reaction mixture is formed by contacting a sample having the target nucleic acid with a first oligonucleotide, second oligonucleotide, 3' nuclease and polymerase. The first oligonucleotide has a 5' region and a 3' region. The 5' region is complementary to the target nucleic acid and the 3' region is non-complementary to the target nucleic acid. The 3' region is preferably operatively coupled to a label, preferably a first member of an interactive pair of labels. The label is preferably operatively coupled to the 3' terminal nucleotide of the first oligonucleotide. The second oligonucleotide forms a duplex with said 5' region of said first oligonucleotide under non-denaturing conditions. The second oligonucleotide can also be operatively coupled to a second member of an interactive pair of labels. The first and second members of the interactive pair of labels interact when the first oligonucleotide and the second oligonucleotide form a duplex and do not interact when the first and second oligonucleotides dissociate. The reaction mixture is subjected to conditions which permit annealing of the first oligonucleotide to the target nucleic acid to form a cleavage structure. The cleavage structure is cleaved by the 3' nuclease. Cleavage of the 3' cleavage structure generates a detectable signal that is indicative of the presence and/or amount of the target in a sample. Optionally, the cleaved first oligonucleotide of the cleavage structure is then extended by the polymerase, thereby generating a nucleic acid that is complementary to the target. It is contemplated that a detectable signal is generated upon dissociation of the first oligonucleotide/second oligonucleotide hybrid and competitive duplex formation of the probe with the target. The signal is detected and/or measured and is indicative of the presence and/or amount of the target in the sample. In addition, it is preferred that when the first and second oligonucleotides form a duplex, at least a 3' nucleotide base of the first oligonucleotide is non-complementary to the second oligonucleotide. It is preferred that one to ten, preferably one to four 3' terminal nucleotides of the first oligonucleotide are non-complementary to the second oligonucleotide and more preferably one to five or more 3' terminal nucleotides are non-complementary to the second oligonucleotide.

In yet another aspect, the invention provides a method for detecting a target nucleic acid. The method entails forming a reaction mixture by contacting a sample with a first oligonucleotide, second oligonucleotide and 3' nuclease. The second oligonucletoide forms a duplex with a region of the first oligonucleotide under non-denaturing conditions. The first oligonucleotide includes a label, preferably the label is one member of an interactive pair of labels. The label is preferably operatively coupled to the 3' terminal nucleotide of the first oligonucleotide. The second oligonucleotide can include a second member of an interactive pair of labels. The labels interact when the first and second oligonucleotides form a duplex, but do not interact when the first and second oligonucleotides dissociate. The reaction mixture is subjected to conditions which permit disassociation of the first and second oligonucleotides, annealing of the first oligonucleotide to the target and cleavage of the first oligonucleotide. The first oligonucleotide forms a 3' flap when annealed to the target nucleic acid. This 3' flap is cleaved by the 3' nuclease. When the second oligonucleotide contains a second member of an interactive pair of labels, it is contemplated that a detectable signal is generated upon dissociation of the first oligonucleotide/second oligonucleotide hybrid and competitive duplex formation of the probe with the target. The signal is detecting and/or measured and is indicative of the presence and/or amount of the target in the sample. In addition, when the first and second oligonucleotides form a duplex, at least a 3' nucleotide bases of the first oligonucleotide is be non-complementary to the second oligonucleotide. It is preferred that one to ten, preferably one to four 3' terminal nucleotides of the first oligonucleotide are non-complementary to the second oligonucleotide and more preferably one to five or more 3' terminal nucleotides are non-complementary to the second oligonucleotide.

In still another aspect, the invention provides a method for detecting a target nucleic acid. The method includes forming a reaction mixture by contacting a sample containing a target nucleic acid with a first oligonucleotide, second oligonucleotide, 3' nuclease and polymerase. The first oligonucleotide forms a duplex with said second oligonucleotide under non-denaturing conditions. Each oligonucleotide has one member of an interactive pair of labels which interact when the first and second oligonucleotides form a duplex, but do not interact when the first and second oligonucleotides are dissociated. Alternatively, the first oligonucleotide includes a member of an interactive pair of labels, preferably at the 3' end, and no label is included in the second oligonucleotide. The reaction is subjected to reaction conditions which permit annealing of the first oligonucleotide to the target so that the first oligonucleotide forms a 3' flap. The reaction conditions also permit cleavage of the 3' flap and extension of the cleaved first oligonucleotide. When the second oligonucleotide contains a second member of an interactive pair of labels, it is contemplated that a detectable signal is generated upon dissociation of the first oligonucleotide/second oligonucleotide hybrid and competitive duplex formation of the probe with the target. The signal is detecting and/or measured and is indicative of the presence and/or amount of the target in the sample. Where the second oligonucleotide does not include a member of the interactive pair of labels, a second member of the interactive pair of labels can be included in the target molecule, or operatively coupled to the first oligonucleotide at a position 5' to the 3' flap, such that upon cleavage of the 3' flap, a detectable signal is produced. In addition, it is preferred that when the first and second oligonucleotides form a duplex, at least a 3' nucleotide bases of the first oligonucleotide are non-complementary to the second oligonucleotide. It is preferred that one to ten, preferably one to four 3' terminal nucleotides of the first oligonucleotide are non-complementary to the second oligonucleotide and more preferably one to five or more 3' terminal nucleotides are non-complementary to the second oligonucleotide.

In any of the foregoing aspects of the invention, where the first and second oligonucleotides each include a member of an interactive pair of labels, it is contemplated that a detectable signal is generated upon dissociation of the first oligonucleotide/second oligonucleotide hybrid and competitive duplex formation of the probe with the target. In addition, upon hybridization of the first oligonucleotide to a target sequence, the 3' region forms a 3' flap that is cleaved by the 3' nuclease, resulting in liberation of the label that is operatively coupled to the 3' region of the first oligonucleotide, thus producing a detectable signal. For example, if the first oligonucleotide includes a fluorophore operatively coupled to the 3' terminal nucleotide, and a quencher operatively coupled to a nucleotide that is 5' of the 3' region/flap, then cleavage of the 3' flap would result in the separation of the fluorophore and quencher, thus, permitting detectable fluorescence emission from the fluorophore.

In any of the foregoing aspects of the invention, the amount of cleaved 3' nucleotide, i.e., cleavage product generated during the reaction, can be detected using a number of assays, particularly those that detect a change in fluorescence when the nucleotide is cleaved, e.g., fluorescence intensity, fluorescence polarization, fluorescence energy transfer, etc.

In any of the foregoing aspects of the invention, it is preferred that the 3' region of the first oligonucleotide contain a G base. The 3' region of the first oligonucleotide can also include a C base.

In any of the foregoing aspects of the invention the second oligonucleotide can include a 3' terminal nucleotide that is non-complementary to the first oligonucleotide. It is preferred that one to ten, preferably one to four 3' terminal nucleotides of the second oligonucleotide are non-complementary to the first oligonucleotide and more preferably one to five 3' or more terminal nucleotides are non-complementary to the first oligonucleotide. In addition, the 3' terminal nucleotide of the second oligonucleotide can further include a blocking group to inhibit extension of the second oligonucleotide.

In any of the foregoing aspects of the invention, it is also contemplated that, when the second oligonucleotide does not include a second member of an interactive pair of labels, the first oligonucleotide, in addition to a first member of an interactive pair of labels, can include a second member of the interactive pair of labels. The first member is operatively coupled to the 3' region of the first oligonucleotide, and the second member is operatively coupled to the first oligonucleotide at a position that is 5' from the 3' region. The second member of the interactive binding pair can be operatively coupled to the first oligonucleotide so as to be interactively operative. For example, the second member of the interactive pair of labels can be operatively coupled immediately 5' of the 3' region, or can be spaced 1 to 20 or more bases 5' of the 3' region, and can be up to 30 or more bases 5' of the 3' region, up to and including being operatively coupled to the 5' terminal nucleotide of the first oligonucleotide.

BRIEF DESCRIPTION OF THE DRAWINGS

FIGS. 2A and 2B illustrate the probes and targets used in determining the optimal length of the 3' flap. In FIG. 2B, the underlined letters indicate mismatches in the fluor oligos to the target amplicon or mismatches in the quencher complements to the fluro oligo.

FIG. 5 illustrates the probe and target sequences used in Examples 5 and 6. The letters underlined with a dotted line indicate mismatches in the fluor oligos to the target amplicon. Also, the flaps of the CCR2__1A_ExoV1__3'Fam10, CCR2__1A_ExoV1__3'Fam11, CCR2__1A_ExoV1__3'Fam12, CCR2__1A_ExoV1__3'Fam13, CCR2__1A_ExoV1__3'Fam14, CCR2__1A_ExoV1__3'Fam15, and CCR2__1A_ExoV1__3'Fam16 oligos in FIG. 5 have homology with the CCR2 gene target.

FIG. 6 is a graphical representation of the fluorescence generated upon the cleavage of a probe with a label coupled to the 3' terminal OH, and in the presence of a QC oligonucleotide.

FIG. 7 is a graphical representation of the fluorescence generated upon the cleavage of a probe with a label coupled to the 3' terminal OH, and in the presence or absence of a CO or QC oligonucleotide.

FIG. 8 is a graphical representation of a standard curve using the CCR2 3'FAM7 probe and QC oligonucleotide.

FIG. 9 shows a plot of Ct values vs. template amount for the standard curve shown in FIG. 8.

FIG. 11 shows the sequences of the QC 3' flap 1 oligonucleotide, CO oligonucletoides, CCR2 3' Fam8 and CCR2 Rev 199. The underlined letters indicate mismatches in the fluor oligos to the target amplicon or mismatches in the quencher complements to the fluro oligo.

DETAILED DESCRIPTION

The invention provides for compositions, kits and methods of generating a signal to detect the presence of a target nucleic acid in a sample wherein a nucleic acid is treated with the combination of a 3' nuclease and a probe having a 3' flap. The invention also provides for a process for detecting or measuring a nucleic acid that allows for concurrent amplification, cleavage and detection of a target nucleic acid sequence in a sample.

The practice of the present invention will employ, unless otherwise indicated, conventional techniques of molecular biology, microbiology and recombinant DNA techniques, which are within the skill of the art. Such techniques are explained fully in the literature. See, e.g., Sambrook, Fritsch & Maniatis, 1989, *Molecular Cloning: A Laboratory Manual*, Second Edition; *Oligonucleotide Synthesis* (M. J. Gait, ed., 1984); *Nucleic Acid Hybridization* (B. D. Harnes & S. J. Higgins, eds., 1984); *A Practical Guide to Molecular Cloning* (B. Perbal, 1984); and a series, *Methods in Enzymology* (Academic Press, Inc.). All patents, patent applications, and publications mentioned herein, both supra and infra, are hereby incorporated by reference.

Definitions

As used herein a "3'nuclease" refers to an enzyme that cleaves a cleavage structure according to the invention. The term "3'nuclease" encompasses an enzyme that comprises a 3' exonuclease and/or an endonuclease activity. In one embodiment, the "3'nuclease" encompasses an enzyme that consists essentially of a 3' exonuclease and/or an endonuclease activity. As used herein, "consists essentially of" refers to an enzyme wherein the predominant activity of the enzyme is a 3' exonucleolytic and/or endonucleolytic activity, such that one or both of 5' to 3' synthetic activity and 5' single-stranded flap cleavage activity (i.e., 5' endonucleolytic and/or 5'exonucleolytic activity) are substantially lacking. "Substantially lacks" means that the 3' nuclease possesses no more than 5% or 10% and preferably less than 0.1%, 0.5%, or 1% of the activity of a wild type enzyme (e.g. for 5' to 3' synthetic activity and the 5' endonucleolytic and/or '5 exonucleolytic activities, the enzyme may be a wild type DNA polymerase having these activities). 5' to 3' synthetic activity can be measured, for example, in a nick translation assay or an enzymatic sequencing reaction which involve the formation of a phosphodiester bridge between the 3'-hydroxyl group at the growing end of an oligonucleotide primer and the 5'-phosphate group of an incoming deoxynucleotide, such that the overall direction of synthesis is in the 5' to 3' direction. 5' flap cleavage may be measured in a cleavage reaction as described in U.S. Pat. Nos. 6,528,254 and 6,548,250.

Figure 1:
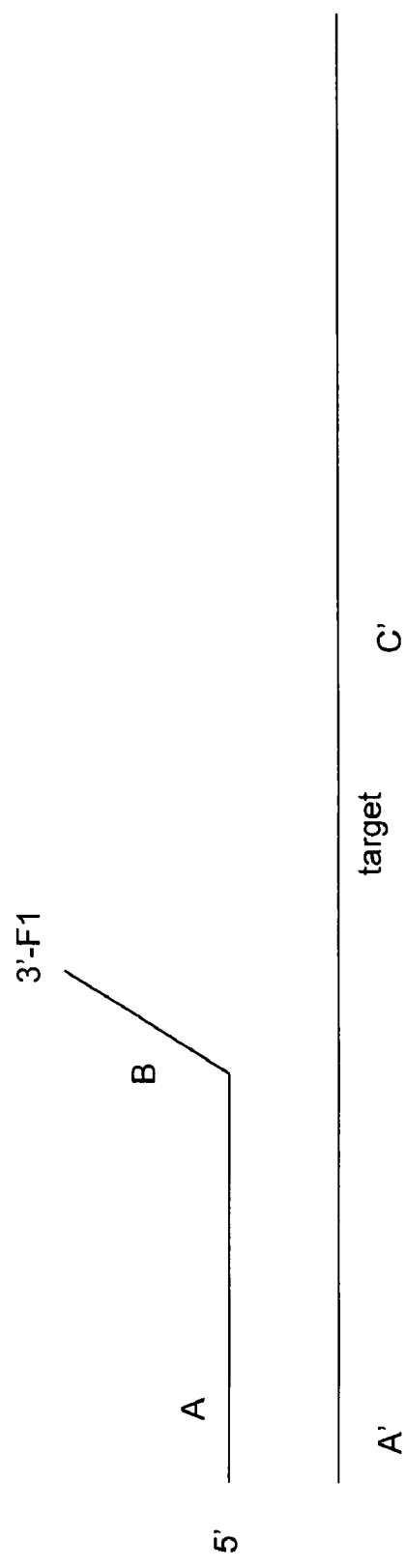
FIG. 1 illustrates one embodiment of a cleavage structure of the invention.

As used herein, a "cleavage structure" refers to a polynucleotide structure (for example as illustrated in FIG. 1) comprising at least a duplex nucleic acid having a single stranded region comprising a 3' flap. A 3' flap of a cleavage structure according to the invention is preferably about 1-500 nucleotides, more preferably about 1-25 nucleotides and most preferably about 2-5 nucleotides.

As used herein a "flap" refers to a region of single stranded nucleic acid that extends from a double stranded nucleic acid molecule. A flap according to the invention is preferably between about 1-500 nucleotides, more preferably about 1-25 nucleotides and most preferably about 2-5 nucleotides.

A cleavage structure according to the invention preferably comprises a target nucleic acid sequence and an oligonucleotide that specifically hybridizes with the target nucleic acid sequence (e.g., probe) and has a 3' flap that is does not hybridize to the target. For example, a cleavage structure according to the invention may comprise a target nucleic acid sequence, and a downstream oligonucleotide that has a 5' portion that is complementary to the target and a 3' region which is non-complementary to and doesn't anneal with the target. (See FIG. 1)

A "cleavage structure", as used herein, does not include a double stranded nucleic acid structure with only a 5' single-stranded flap. As used herein, a "cleavage structure" comprises ribonucleotides or deoxyribonucleotides and thus can be RNA or DNA.

A cleavage structure according to the invention is formed by the steps of 1. incubating a) an oligonucleotide probe and b) an appropriate target nucleic acid sequence wherein the target sequence is complementary to a 5' region of the probe and c) a suitable buffer, under conditions that allow the nucleic acid sequence to hybridize to the 5' region of the oligonucleotide probe and wherein a 3' region of the probe forms a flap.

As used herein, "cleaving" refers to enzymatically separating a cleavage structure into distinct (i.e. not physically linked to other fragments or nucleic acids by phosphodiester bonds) fragments or nucleotides and fragments that are released from the cleavage structure. For example, cleaving a labeled cleavage structure refers to separating a labeled cleavage structure according to the invention and defined herein, into distinct fragments including fragments derived from an oligonucleotide that specifically hybridizes with a target nucleic acid sequence or wherein one of the distinct fragments is a labeled nucleic acid fragment derived from a target nucleic acid sequence and/or derived from an oligonucleotide that specifically hybridizes with a target nucleic acid sequence that can be detected and/or measured by methods well known in the art and described herein that are suitable for detecting the labeled moiety that is present on a labeled fragment.

As used herein, "label" or "labeled moiety capable of providing a signal" refers to an atom or molecule which can be used to provide a detectable (preferably quantifiable) signal, and which can be operatively coupled to a nucleic acid. Labels may provide signals detectable by fluorescence, radioactivity, colorimetry, gravimetry, X-ray diffraction or absorption, magnetism, enzymatic activity, mass spectrometry, binding affinity, hybridization radiofrequency and the like. A label, as used herein, can also refer to a quencher moiety that provides a detectable signal in that it quenches the signal of an interacting fluorophore when in proximity to the fluororophore, but permits a signal to be emitted by the fluorophore when separated from the fluorophore.

As used herein, the phrase "an interactive pair of labels" or "a pair of interactive labels", refers to a pair of molecules which interact physically, optically or otherwise in such a manner as to permit detection of their proximity by means of a detectable signal. Examples of a "pair of interactive labels" include, but are not limited to, labels suitable for use in fluorescence resonance energy transfer (FRET) (Stryer, L. Ann. Rev. Biochem. 47, 819-846, 1978), scintillation proximity assays (SPA) (Hart and Greenwald, Molecular Immunology 16:265-267, 1979; U.S. Pat. No. 4,658,649), luminescence resonance energy transfer (LRET) (Mathis, G. Clin. Chem. 41, 1391-1397, 1995), direct quenching (Tyagi et al., Nature Biotechnology 16, 49-53, 1998), chemiluminescence energy transfer (CRET) (Campbell, A. K., and Patel, A. Biochem. J. 216, 185-194, 1983), bioluminescence resonance energy transfer (BRET) (Xu, Y., Piston D. W., Johnson, Proc. Natl. Acad. Sc., 96, 151-156, 1999), or excimer formation (Lakowicz, J. R. Principles of Fluorescence Spectroscopy, Kluwer Academic/Plenum Press, New York, 1999). A pair of interactive labels (e.g., a fluorophore and a quencher) are effectively positioned so that they interact (e.g., quench a detectable signal) when they are not separated (e.g., the probe is not cleaved), but produce a detectable signal (e.g., fluoresce) when they do not interact (e.g., cleavage of the probe between the labels). Generally, in order for a pair of interactive labels to interact they should be placed no more than twenty nucleotides from each other.

As used herein, "generating a signal" refers to producing a optical, chemical, etc. signal which is indicative of the presence of a target nucleic acid. For example, according to the invention a pair of interactive labels operatively coupled to a probe (e.g., fluorescer and quencher) may generate a signal (e.g., fluoresce) when a 3' nuclease cleaves the oligonucleotide between the labels, and the labels separate (e.g., labels no longer interact).

As used herein, "detecting a signal" or "measuring a signal" refers to determining the presence of a particular target nucleic acid sequence in a sample or determining the amount of a particular target nucleic acid sequence in a sample. In some embodiments of the invention, the detected signal is derived from the labeled 3' flap of a downstream probe of a cleavage structure according to the invention (FIG. 1). In one embodiment, the signal is detected upon the separation of a pair of interactive labels upon the cleavage of a cleavage structure. In another embodiment, a first member of an interactive pair of labels attached to the 5' end of a probe and a second member of the pair of interactive labels is attached to the 3' flap of the probe. In still another embodiment, a first member of an interactive pair of labels attached to a first oligonucleotide of an oligonucleotide pair and a second member of the pair of interactive labels is attached to a second oligonucleotide of the oligonucleotide pair.

According to the invention, the probe may also be labeled internally.

In one embodiment, a cleavage structure according to the invention can be prepared by incubating a target nucleic acid sequence with a probe comprising a non-complementary, labeled, 3' region that does not anneal to the target nucleic acid sequence and forms a 3' flap, and a complementary 5' region that anneals to the target nucleic acid sequence. According to this embodiment of the invention, the detected nucleic acid may be derived from the labeled 3' flap region of the probe.

As used herein, "detecting release of labeled fragments" or "measuring release of labeled fragments" refers to determining the presence of a labeled fragment in a sample or determining the amount of a labeled fragment in a sample. Methods well known in the art and described herein can be used to detect or measure release of labeled fragments. A method of detecting or measuring release of labeled fragments will be appropriate for measuring or detecting the labeled moiety that is present on the labeled fragments. The amount of a released labeled fragment that can be measured or detected is preferably about 25%, more preferably about 50% and most preferably about 95% of the total starting amount of labeled probe.

As used herein, "labeled fragments" refer to cleaved mononucleotides or small oligonucleotides or oligonucleotides derived from the labeled cleavage structure according to the invention.

As used herein, "sample" refers to any substance containing or presumed to contain a nucleic acid of interest (a target nucleic acid sequence) or which is itself a nucleic acid containing or presumed to contain a target nucleic acid sequence of interest. The term "sample" thus includes a sample of nucleic acid (genomic DNA, cDNA, RNA), cell, organism, tissue, fluid, or substance including but not limited to, for example, plasma, serum, spinal fluid, lymph fluid, synovial fluid, urine, tears, stool, external secretions of the skin, respiratory, intestinal and genitourinary tracts, saliva, blood cells, tumors, organs, tissue, samples of in vitro cell culture constituents, natural isolates (such as drinking water, seawater, solid materials), microbial specimens, and objects or specimens that have been "marked" with nucleic acid tracer molecules.

As used herein, "target nucleic acid sequence" refers to a region of a nucleic acid that is to be either replicated, amplified, and/or detected.

As used herein, "nucleic acid polymerase" refers to an enzyme that catalyzes the polymerization of nucleoside triphosphates. Generally, the enzyme will initiate synthesis at the 3'-end of the primer annealed to the target sequence, and will proceed in the 5'-direction along the template, and if possessing a 3' nuclease activity, hydrolyzing a 3' flap from a probe. Known DNA polymerases include, for example, *E. coli* DNA polymerase I, T7 DNA polymerase, *Thermus thermophilus* (Tth) DNA polymerase, *Bacillus stearothermophilus* DNA polymerase, *Thermococcus litoralis* DNA polymerase, *Thermus aquaticus* (Taq) DNA polymerase and *Pyrococcus furiosus* (Pfu) DNA polymerase.

In one embodiment, the nucleic acid polymerase has polymerase activity but is deficient in 3'-5' nuclease activity and/or deficient in 5'-3' nuclease activity (e.g., Pfu +pol/−exo). In another embodiment, the nucleic acid polymerase has 3'-5' nuclease activity but is different in polymerase activity (e.g., Pfu −pol/+exo).

As used herein, "thermostable" refers to an enzyme which is stable and active at temperatures as great as between about 90-100° C. and more preferably between about 70-98° C. to heat as compared, for example, to a non-thermostable form of an enzyme with a similar activity. For example, a thermostable nucleic acid polymerase or 3' nuclease derived from thermophilic organisms such as *P. furiosus, M. jannaschii, A. fulgidus* or *P. horikoshii* are more stable and active at elevated temperatures as compared to a nucleic acid polymerase from *E. coli* or a mammalian enzymes. A representative thermostable nucleic acid polymerase isolated from *Thermus aquaticus* (Taq) is described in U.S. Pat. No. 4,889,818 and a method for using it in conventional PCR is described in Saiki et al., 1988, *Science* 239:487. Another representative thermostable nucleic acid polymerase isolated from *P. furiosus* (Pfu) is described in Lundberg et al., 1991, *Gene*, 108:1-6. Additional representative temperature stable polymerases include, e.g., polymerases extracted from the thermophilic bacteria *Thermus flavus, Thermus ruber, Thermus thermophilus, Bacillus stearothermophilus* (which has a somewhat lower temperature optimum than the others listed), *Thermus lacteus, Thermus rubens, Thermotoga maritima*, or from thermophilic archaea *Thermococcus litoralis*, and *Methanothermus fervidus*.

Temperature stable polymerases and 3' nucleases are preferred in a thermocycling process wherein double stranded nucleic acids are denatured by exposure to a high temperature (about 95° C.) during the PCR cycle.

As used herein, "endonuclease" refers to an enzyme that cleaves bonds, preferably phosphodiester bonds, within a nucleic acid molecule. An endonuclease according to the invention can be specific for single-stranded or double-stranded DNA or RNA.

As used herein, "exonuclease" refers to an enzyme that cleaves bonds, preferably phosphodiester bonds, between nucleotides one at a time from the end of a polynucleotide. An exonuclease according to the invention can be specific for the 5' or 3' end of a DNA or RNA molecule, and is referred to herein as a 5' exonuclease or a 3' exonuclease.

As used herein, a "primer" according to the invention is preferably 5 to 100 and more preferably 5 to 40 in length. An "primer" is at least partially complementary to the target nucleic acid at a length of its 3' terminus sufficient to permit its use as a primer for nucleic acid synthesis using the target nucleic acid as a template. A "primer" according to the invention includes a probe which has a cleaved 3' flap, as defined herein.

As used herein, a "probe" according to the invention is preferably 5-120, and more preferably 16-45 nucleotides in length. A "probe" comprises a 3' and a 5' region. The 5' region of a probe is at least partially complementary to a target nucleic acid. A 3' region of a "probe" is preferably 1 to 80 nucleotides in length and more preferably 1 to 10 nucleotides in length. In some embodiments, the "probe" is a "first oligonucleotide."

A "first oligonucleotide" according to the invention is preferably 5-1000, more preferably 8 to 100 and most preferably 10-20 nucleotides in length. A "first" oligonucleotide is at least partially complementary to, and able to form a hybrid with the target nucleic acid, and forms a 3' flap when annealed to the target nucleic acid. The first oligonucleotide is also at least partially complementary to a second oligonucleotide and forms an oligonucleotide duplex with a "second oligonucleotide" when not hybridized with the target under non-denaturing conditions. In some embodiment, after the 3' flap of the first oligonucleotide is cleaved by a 3' nuclease the cleaved first oligonucleotide is extended by a polymerase.

A "second oligonucleotide" according to the invention is preferably 5-1000, more preferably 8 to 100 and most preferably 10-20 nucleotides in length. A "second oligonucleotide" is at least partially complementary to the first oligonucleotide so as to form an oligonucleotide duplex (e.g., pair) with the first oligonucleotide when the first oligonucleotide is not hybridized with the target under non-denaturing conditions.

As used herein, "fully complementary" means that 100% of the nucleotides of an oligonucleotide can hydrogen bond to the corresponding complementary nucleotides of the target nucleic acid or other oligonucleotide.

As used herein, "at least partially complementary" as it refers to an oligonucleotide, means that less than 100%, (e.g., 99%, 90%, 75%, 50%, 25% etc . . . . ) of the nucleotides of the oligonucleotide can hybridize (that is form hydrogen bonds) with nucleotides of the target nucleic acid or other oligonucleotide under standard stringent conditions. Where an oligonucleotide is "partially complementary", the region of complementary nucleotides may or may not be contiguous nucleotides.

As used herein, "conditions which permit formation of a duplex" refer to a buffer (i.e., of a specified salt and organic solvent concentration), a temperature, an incubation time, and the concentrations of the components of the duplex (for example a target nucleic acid and a downstream probe) that are possible and preferably optimal for the formation of a duplex of the invention. For example, in one embodiment of the invention, under "conditions which permit formation of a duplex", a target nucleic acid and a probe will hybridize such that the 3' region of the probe forms a flap.

As used herein, "duplex" and "hybrid" refer to a complex comprising two nucleic acids associated with each other by stable base pairing of at least eight bases up to the full length of the nucleic acid sequence under non-denaturing conditions. The terms "duplex" and "hybrid" are equivalent terms, but are used differently herein to differentiate between an association of a probe to target vs. a first oligonucleotide to a second oligonucltoide. As used herein, the term "hybrid" refers to a complex comprising a target nucleic acid and at least a 5' region of a probe (i.e., the first oligonucleotide), wherein the complementary nucleotide bases of the target nucleic acid and at least a 5' region of a probe are hybridized due to the formation of hydrogen bonds. "Duplex" refers to a complex comprising a first oligonucleotide and a second oligonucleotide of the invention having complementary base paring of at least eight bases. The complementary base paring of at least eight bases in a duplex can be discontinuous, or can be contiguous.

As used herein, "non-denaturing conditions" refer to hybridization or wash conditions that permit the formation of a duplex or hybrid between two nucleic acids that share at least 8 complementary residues. For example, non-denaturing conditions include temperatures that are at least 3, 5, or 10 degrees below the melting temperature of the duplex or hybrid. Exemplary non-denaturing hybridization and wash conditions have a physiological ionic strength, an ionic strength of between 0.1, 0.5, 0.8, 0.9, 1.1, 1.5, or 2 fold that of phosphate buffered saline (PBS), or an ion strength less than 2×, 1×, or 0.75×SSC sodium chloride/sodium citrate as described in *Current Protocols in Molecular Biology*, John Wiley & Sons, N.Y. (1989), 6.3.1-6.3.6. Exemplary non-denaturing hybridization and wash conditions have a pH between 5-10.5, 6-9, 6-8.5, 6-8, or 6.5-7.5

As used herein a "FEN nuclease" refers to an enzyme that cleaves a 5' flap. The term "FEN nuclease" encompasses an enzyme that consists essentially of a 5' exonuclease and/or an endonuclease activity. As used herein, "consists essentially of" refers to an enzyme wherein the predominant activity of the enzyme is a 5' exonucleolytic and/or endonucleolytic activity, such that one or both of 5' to 3' synthetic activity and 3' single-stranded flap cleavage activity (i.e., 3' endonucleolytic and/or 3' exonucleolytic activity) are substantially lacking. FEN nucleases and methods of their use are described in U.S. Pat. Nos. 6,528,254; 6,548,250 and U.S. Patent Application No. 60/794,628, filed Apr. 24, 2006, each of which is herein incorporated by reference in their entirety.

In one aspect, the invention is directed to a composition for generating a signal that is indicative of the presence of a target nucleic acid in a sample. The composition includes an upstream primer, 3' nuclease and downstream probe having a 3' flap. The 3' nuclease may be any 3'-5' exonuclease or 3'-5' endonuclease. 3' nucleases include suitable DNA polymerases known in the art and described herein. For example, suitable DNA polymerases include, *Pyrococcus furiosus* (Pfu) DNA polymerase, *Thermococcus litoralis* DNA polymerase, *Thermococcus barossii* DNA polymerase, *Thermococcus gorgonarius* DNA polymerase and *E. coli* DNA polymerase I. The 3' nuclease can be thermostable. The downstream probe includes a 5' region and a 3' region, wherein the 5' region is complementary to the target and the 3' region is non-complementary to the target and forms a 3' flap when the probe is annealed to the target. In some embodiments, the downstream probe includes at least one labeled moiety capable of providing a signal. In further embodiments, the downstream probe includes a pair of interactive signal generating labeled moieties. Suitable interactive labels include quencher and fluorescer moieties. Generally, one member of the pair of interactive signal generating labeled moieties is coupled to the 3' flap of the downstream probe, so that upon cleavage by the 3' nuclease the 3' flap is cleaved and the interactive signal generating labeled moieties are separated. In further, embodiments the second member of the interactive signal generating labeled moieties is operatively coupled to the 5' region of the downstream probe. The second member of the interactive signal generating labeled moieties can be located at any position on the oligonucleotide 5' to the 3' flap. The second member can be operatively coupled to the 3' oligonucleotide so as to be interactively operative (e.g., between 2 to 20 bases 5' of the 3' region).

In another aspect, the invention is directed to a composition for generating a signal indicative of the presence of a target nucleic acid. The composition includes a probe having a 5' region that hybridizes with the target and a 3' region that is non-complementary to the target and that forms a 3' flap. The composition also includes a *P. furiosus* polymerase having 3' nuclease activity. The composition may further include the target nucleic acid. In yet a further embodiment, the composition may further include an upstream primer that hybridizes upstream of the probe.

In another aspect, the invention is directed to an oligonucleotide pair for use in detecting the presence of a target nucleic acid. The oligonucleotide pair includes a first oligonucleotide and a second oligonucleotide. The first oligonucleotide has a 5' region and a 3' region. The 5' region is complementary to the target nucleic acid. The 3' region is non-complementary to the target and is operatively coupled to a label, preferably a first member of an interactive pair of labels. The label is preferably operatively coupled to the 3' terminal nucleotide of the first oligonucleotide. The second oligonucleotide forms a duplex with said 5' region of said first oligonucleotide under non-denaturing conditions and can be operatively coupled to a second member of an interactive pair of labels. The first and the second members of the pair of interactive labels interact, when present, upon formation of a duplex of the first oligonucleotide and the second oligonucleotide, and do not interact when said first oligonucleotide and second oligonucleotide dissociate. The oligonucleotide pair may be supplied in a kit. The second oligonucleotide of the oligonucleotide pair may be complementary to the full length or just a portion of the first oligonucleotide. For example, the second oligonucleotide may be complementary to both the 5' and 3' regions of the first oligonucleotide or it may be complementary to the 5' region but not the 3' region. Preferably the first and second oligonucleotides form a stable duplex (e.g., comprise at least 8 nucleotides that are complementary). The oligonucleotide pair may be included in a composition that may further include a 3' nuclease and/or polymerase. The oligonucleotide pair may also be included in a kit which further includes packaging materials.

In another aspect, the invention is directed to a kit for generating a signal that is indicative of the presence of a target nucleic acid in a sample. The kit includes an upstream primer, 3' nuclease, probe having a 3' flap and suitable buffer. The 3' nuclease may be a polymerase with 3'-5' nuclease activity such as *Pyrococcus furiosus* (Pfu) DNA polymerase, *Thermococcus litoralis* DNA polymerase, *Thermococcus barossii* DNA polymerase, *Thermococcus gorgonarius* DNA polymerase and *E. coli* DNA polymerase I. In some embodiments, the 3' nuclease is thermostable. The probe includes at least a 5' region and a 3' region. The 5' region is complementary to the target, while the 3' region is sufficiently non-complementary to the target so as to form a 3' flap. In some embodiments, the probe includes a label, and preferably includes at least one member of an interactive pair of labels capable of providing a signal. It is preferred that the label is operatively coupled to the 3' terminal nucleotide of the probe (e.g., first oligonucleotide). In further embodiments, the probe includes a pair of interactive signal generating labeled moieties. Suitable interactive labels include quencher and fluorescer moieties. Generally, one member of the pair of interactive signal generating labeled moieties is coupled to the 3' flap of the probe, so that upon cleavage by the 3' nuclease the 3' flap is cleaved and the interactive signal generating labeled moieties are separated. In further, embodiments the second member of the interactive signal generating labeled moieties is operatively coupled to the 5' region of the probe (e.g., in the range of 2 and 20 or more bases 5' of the 3' flap, up to being coupled to the 5' terminal nucleotide of the probe).

In any of the foregoing embodiments, the second oligonucleotide may not be coupled to a member of an interactive pair of labels. Where a member of an interactive pair of labels is not operatively coupled to the second oligonucleotide, two members of a pair of interactive labels can be operatively coupled to the first oligonucleotide. Alternatively, a first and second member of an interactive pair of labels can be operatively coupled to the first oligonucleotide, and either the first or second member of the interactive pair of labels can also be operatively coupled to the second oligonucleotide. For example, the first oligonucleotide may include a fluorophore and quencher, and the second oligonucleotide may also include a quencher. In addition, when the first and second oligonucleotides are hybridized to form a duplex, at least a 3' nucleotide of the first oligonucleotide is non-complementary to the second oligonucleotide. It is preferred that four 3' terminal nucleotides of the first oligonucleotide are non-complementary to the second oligonucleotide and more preferably five 3' terminal nucleotides are non-complementary to the second oligonucleotide. More preferably, the five, six, seven, eight, nine, and up to ten or more 3' terminal nucleotides of the first oligonucleotide are non-complementary to the 5' end of the second oligonucleotide. In addition, it is possible that at least a 3' nucleotide of the second oligonucleotide is non-complementary to the first oligonucleotide. It is preferred that four 3' terminal nucleotides of the second oligonucleotide are non-complementary to the first oligonucleotide and more preferably five 3' terminal nucleotides are non-complementary to the first oligonucleotide. More preferably, the five, six, seven, eight, nine, and up to ten or more 3' terminal nucleotides of the second oligonucleotide are non-complementary to the 5' end of the first oligonucleotide. In any of the foregoing embodiments, in addition to a first member of an interactive pair of labels (e.g., a fluorophore) operatively coupled to the 3' region or flap of the first oligonucleotide, the first oligonucleotide can include a second member of an interactive pair of labels (e.g., a quencher) operatively coupled 5' to the 3' region or flap. The second member can be operatively coupled to the oligonucleotide so as to be interactively operative (e.g., in the range of 2 to 20 or more bases 5' of the 3' region, including being operatively coupled to the 5' terminal nucleotide of the first oligonucleotide).

I. Methods of Use

The invention provides for a method of generating a signal indicative of the presence of a target nucleic acid sequence in a sample comprising the steps of forming a labeled cleavage structure by incubating a target nucleic acid sequence with a probe having a 3' flap, and cleaving the cleavage structure with a 3' nuclease. The method of the invention can be used in a PCR based assay as described below and in the Examples.

In one aspect, the invention is directed to a method for detecting a target nucleic acid in a sample. The method includes the step of contacting a sample containing the target with a first oligonucleotide, second oligonucleotide and 3' nuclease. The first oligonucleotide has a 5' region and a 3' region. The 5' region is complementary to the target nucleic acid and the 3' region is non-complementary. The 3' region is operatively coupled to a label. Preferably the label is a first member of an interactive pair of labels, and preferably the label is operatively coupled to the 3' terminal nucleotide of the first oligonucleotide. The second oligonucleotide forms a duplex with said 5' region of said first oligonucleotide under non-denaturing conditions and may be operatively coupled to a second member of an interactive pair of labels. The first and second members of the interactive pair of labels interact, when present, upon formation of a duplex of the first oligonucleotide and the second oligonucleotide, and do not interact when the first and second oligonucleotides dissociate. When the second oligonucleotide contains a second member of an interactive pair of labels, it is contemplated that a detectable signal is generated upon dissociation of the first oligonucleotide/second oligonucleotide hybrid and competitive duplex formation of the probe with the target. In addition, upon hybridization with the target, a cleavage structure is formed by the 3' region of the first oligonucleotide that is then cleaved by the 3' nuclease. Because the first oligonucleotide has a label at the 3' terminus, a detectable signal is produced on cleavage of the 3' cleavage structure (i.e., cleavage of the 3' flap). The signal is detecting and/or measured and is indicative of the presence and/or amount of the target in the sample.

In yet another aspect, the invention provides another method for detecting a target nucleic acid in a sample. A reaction mixture is formed by contacting a sample having the target nucleic acid with a first oligonucleotide, second oligonucleotide, 3' nuclease and polymerase. The first oligonucleotide has a 5' region and a 3' region. The 5' region is complementary to the target nucleic acid and the 3' region is non-complementary to the target nucleic acid. The 3' region is operatively coupled to a label such as a first member of an interactive pair of labels. The second oligonucleotide forms a duplex with said 5' region of said first oligonucleotide under non-denaturing conditions and may be operatively coupled to a second member of an interactive pair of labels. The first and second members of the interactive pair of labels interact, when present, upon formation of a duplex of the first oligonucleotide and the second oligonucleotide, and do not interact when the first and second oligonucleotides dissociate. The reaction mixture is subjected to conditions which permit annealing of the first oligonucleotide to the target nucleic acid to form a cleavage structure. The cleavage structure is cleaved by the 3' nuclease. The cleaved first oligonucleotide of the cleavage structure is then extended by the polymerase, thereby generating a nucleic acid that is complementary to the target. Thus, the first oligonucleotide may function as both a probe (hybridizing to the target and producing a detectable signal upon cleavage of the 3' cleavage structure (i.e., the 3' flap)) and primer (priming the synthesis of a nucleotide strand complementary to the target strand). When the second oligonucleotide contains a second member of an interactive pair of labels, it is contemplated that a detectable signal is generated upon dissociation of the first oligonucleotide/second oligonucleotide hybrid and competitive duplex formation of the probe with the target. In addition, upon hybridization with the target, a cleavage structure is formed by the 3' region of the first oligonucleotide that is then cleaved by the 3' nuclease. Because the first oligonucleotide has a label at the 3' terminus, a detectable signal is produced on cleavage of the 3' cleavage structure (i.e., cleavage of the 3' flap). The signal is detecting and/or measured and is indicative of the presence and/or amount of the target in the sample.

In yet another aspect, the invention provides a method for detecting a target nucleic acid. The method entails forming a reaction mixture by contacting a sample with a first oligonucleotide, second oligonucleotide and 3' nuclease. The first oligonucleotide is at least partially complementary to the second oligonucleotide. Both the first and the second oligonucleotides each have one member of an interactive pair of labels. The labels interact when the first and second oligonucleotides form a duplex, but do not interact when the first and second oligonucleotides dissociate. The reaction mixture is subjected to conditions which permit disassociation of the first and second oligonucleotides, annealing of the first oligonucleotide to the target and cleavage of the first oligonucleotide. The first oligonucleotide forms a 3' flap when annealed to the target nucleic acid. This 3' flap is cleaved by the 3' nuclease. When the second oligonucleotide contains a second member of an interactive pair of labels, it is contemplated that a detectable signal is generated upon dissociation of the first oligonucleotide/second oligonucleotide hybrid and competitive duplex formation of the probe with the target. In addition, when the 3' flap is cleaved a further detectable signal is produced. The signal is detecting and/or measured and is indicative of the presence and/or amount of the target in the sample.

In still another aspect, the invention provides a method for detecting a target nucleic acid. The method includes forming a reaction mixture by contacting a sample containing a target nucleic acid with a first oligonucleotide, second oligonucleotide, 3' nuclease and polymerase. The first oligonucleotide forms a duplex with said second oligonucleotide under non-denaturing conditions. Each oligonucleotide has one member of an interactive pair of labels which interact when the first and second oligonucleotides form a duplex, but do not interact when the first and second oligonucleotides are dissociated. The reaction is subjected to reaction conditions which permit annealing of the first oligonucleotide to the target so that the first oligonucleotide forma a 3' flap. The reaction conditions also permit cleavage of the 3' flap and extension of the cleaved first oligonucleotide. When the second oligonucleotide contains a second member of an interactive pair of labels, it is contemplated that a detectable signal is generated upon dissociation of the first oligonucleotide/second oligonucleotide hybrid and competitive duplex formation of the probe with the target. In addition, when the 3' flap is cleaved a further detectable signal is produced. The signal is detecting and/or measured and is indicative of the presence and/or amount of the target in the sample.

In any of the foregoing embodiments, it is possible to omit the member of the interactive pair of labels operatively coupled to the second oligonucleotide. A second member of the interactive pair of labels can be operatively coupled to the target nucleic acid, or may be operatively coupled to the first oligonucleotide at a position that is 5' to the 3' flap. When operatively coupled to the first oligonucleotide, the second member of the interactive pair can be operatively coupled to the oligonucleotide so as to be interactively operative (e.g., in the range of 2 to 20 or more bases 5' of the 3' region, including being connected to the 5' terminal nucleotide of the first oligonucleotide).

In embodiments of the invention that include a 3' nuclease and a polymerase the nuclease and polymerase activities may be supplied by a single peptide or two distinct peptides. For example, both the 3' nuclease and polymerase activity may be supplied by a DNA polymerase. Suitable DNA polymerase would include polymerases with 3'-5' nuclease activity such as *Pyrococcus fitriosus* (Pfu) DNA polymerase, *Thermococcus litoralis* DNA polymerase, *Thermococcus barossii* DNA polymerase, *Thermococcus gorgonarius* DNA polymerase and *E. coli* DNA polymerase I. In some embodiments, the polymerase and nuclease are thermostable.

The 3' region or 3' flap may consist of one, two, three, four, five, six, seven, eight, nine, ten or more nucleotides that do not hybridize to the target. Preferably, the 3' region or flap consists of one to four nucleotides that do not hybridize to the target, and more preferably, consists of two or three nucleotides that do not hybridize to the target. The signal detected includes, detecting a change in fluorescence intensity. Suitable labels in practicing the methods include quenchers and fluorophores.

II. Cleavage Structure

The invention provides for a cleavage structure that can be cleaved by a 3' nuclease, and therefore teaches methods of preparing a cleavage structure. The invention also provides a labeled cleavage structure and methods of preparing a labeled cleavage structure.

A. Preparation of a Cleavage Structure

A cleavage structure according to the invention is formed by incubating a) an oligonucleotide probe having a 3' flap and b) an appropriate target nucleic acid sequence wherein the target sequence is complementary to at least a portion of the probe c) a suitable buffer (for example 1× Probe buffer (15 mM of Tris-HCL (pH8), 50 mM KCL, 5.5 mM $MgCl_2$, 8% glycerol, 1% DMSO) (+dNTP) or 1× Cloned Pfu buffer (Stratagene; Catalog #: 600153) or Herculase II buffer (150 mM Tris base sulfate (pH 10), 10 mM $MgSO_4$, 0.50% Triton X-100, 200 mM $K_2SO_4$, 7.5 mM $(NH_4)_2SO_4$), under conditions that allow the target nucleic acid sequence to hybridize to the oligonucleotide probe (for example 95° C. for 2-5 minutes followed by cooling to between approximately 50-60° C.). The optimal temperature will vary depending on the specific probe(s), primers, polymerases and 3' nucleases. In a preferred embodiment the cleavage structure is prepared in Herculase II buffer, and more preferably in Herculase II buffer combined with 1.25 U Pfu fusion exo+ and 0.125 U fPEF. In preferred embodiments of the invention a cleavage structure comprises an one, two, three, four, five, six or seven 3' end non-complementary nucleotides. Preferably, the 3' region or flap consists of one to four nucleotides that do not hybridize to the target, and more preferably, consists of two or three nucleotides that do not hybridize to the target. The target nucleic acid can be detected by cleavage of the 3' flap, resulting in detection of the 3' label (e.g., 3' FAM).

B. How to Prepare a Labeled Cleavage Structure

In the present invention, a label is attached to an oligonucleotide probe comprising the cleavage structure. Thus, the cleaved mononucleotides or small oligonucleotides which are cleaved by the 3' nuclease can be detected.

A labeled cleavage structure according to the invention is formed by incubating a) an oligonucleotide probe having a 3' flap and b) an appropriate target nucleic acid sequence wherein the target sequence is complementary to at least a portion of the probe c) a suitable buffer (for example 1× Probe buffer (15 mM of Tris-HCL (pH8), 50 mM KCL, 5.5 mM $MgCl_2$, 8% glycerol, 1% DMSO) (+dNTP) or 1× Cloned Pfu buffer (Stratagene; Catalog #: 600153) or Herculase II buffer (150 mM Tris base sulfate (pH 10), 10 mM $MgSO_4$, 0.50% Triton X-100, 200 mM $K_2SO_4$, 7.5 mM $(NH_4)_2SO_4$), under conditions that allow the target nucleic acid sequence to hybridize to the oligonucleotide probe (for example 95° C. for 2-5 minutes followed by cooling to between approximately 50-60° C.). The optimal temperature will vary depending on the specific probe(s), primers, polymerases and 3' nucleases. In preferred embodiments of the invention a cleavage structure comprises an one, two, three or four 3' end non-complementary nucleotides. In a preferred embodiment the cleavage structure is prepared in Herculase II buffer, and more preferably in Herculase II buffer combined with 1.25 U Pfu fusion exo+ and 0.125 U fPEF.

A cleavage structure according to the invention can be prepared by incubating a target nucleic acid sequence with a probe comprising a non-complementary, labeled, 3' region that does not anneal to the target nucleic acid sequence and forms a 3' flap, and a complementary 5' region that anneals to the target nucleic acid sequence. Annealing is preferably carried out under conditions that allow the nucleic acid sequence to hybridize to the oligonucleotide probe (for example 95° C. for 2-5 minutes followed by cooling to between approximately 50-60° C.) in the presence a suitable buffer (for example 1× Probe buffer (15 mM of Tris-HCL (pH8), 50 mM KCL, 5.5 mM $MgCl_2$, 8% glycerol, 1% DMSO) (+dNTP) or 1× Cloned Pfu buffer (Stratagene; Catalog #: 600153) or Herculase II buffer (150 mM Tris base sulfate (pH 10), 10 mM $MgSO_4$, 0.50% Triton X-100, 200 mM $K_2SO_4$, 7.5 mM $(NH_4)_2SO_4$).

Subsequently, any of several strategies may be employed to distinguish the uncleaved labeled nucleic acid from the cleaved fragments thereof. In this manner, the present invention permits identification of those samples that contain a target nucleic acid sequence.

The oligonucleotide probe is labeled, as described herein, by incorporating moieties detectable by spectroscopic, photochemical, biochemical, immunochemical, enzymatic or chemical means. Methods of preparing labeled probes of the invention are provided in the section entitled "Probes" herein.

C. Cleaving a Cleavage Structure and Generating a Signal

A cleavage structure according to the invention can be cleaved by the methods described herein.

D. Detection of Released Labeled Fragments

Detection or verification of the labeled fragments may be accomplished by a variety of methods well known in the art and may be dependent on the characteristics of the labeled moiety or moieties comprising a labeled cleavage structure.

In one embodiment of the invention, a signal generating by the labels is detected by a fluorescent reader, e.g., Mx3005P real-time PCR instrument (Stratagene).

III. 3' Nucleases

The invention employs an enzyme having 3' nuclease activity. The 3' nuclease activity can be provided by polymerases, e.g., a Pfu polymerase, or other exonuclease molecules. Suitable enzymes include proofreading DNA polymerases, described herein and similar enzymes isolated from other organisms.

In some embodiments, the 3' nuclease is thermostable. For example, U.S. Pat. No. 7,030,220 (herein incorporated by reference) discloses a thermostable enzyme from Archaeolgobus fulgidus that catalyzes the degradation of mismatched ends of primers or polynucleotide in the 3' to 5' direction in double stranded DNA. Related enzymes can also be obtained from other Archaea species as well as thermophilic eubacteria.

In some embodiments, the exonuclease activity can be supplied by a DNA polymerase molecule that has an inactive polymerase domain or a polymerase domain that has one or more mutations resulting in substantially less activity of the polymerase domain in comparison to the activity of the starting polymerase domain. In this circumstance, the polymerase activity in an amplification reaction mixture is provided by a different polymerase molecule that has an active polymerase domain. Examples of polymerase polypeptides that have deficient polymerase activity, but retain exonuclease activity, and methods of generating additional such molecules are provided, e.g., in U.S. Publication No. 20040214194, field Jul. 25, 2003 and U.S. Publication No. 20040219558 filed Jul. 25, 2003, both herein incorporated by reference in their entireties.

A polymerase having substantially reduced or substantially lacking polymerase activity (5' to 3' synthetic activity) refers to a polymerase that generally has no more than 5% or 10% and preferably less than 0.1%, 0.5%, or 1% of the activity of a wild type enzyme.

In one embodiment, the 3' nuclease is Pfu DNA polymerase (–pol/+exo).

IV. Nucleic Acid Polymerases

The invention provides for nucleic acid polymerases. In one embodiment, the nucleic acid polymerase substantially lacks 3' nuclease activity but has polymerase activity.

In another embodiment, the nucleic acid polymerase substantially lacks polymerase activity but has 3' nuclease activity. In this embodiment, the nucleic acid perms the function of a 3' nuclease according to the invention.

In yet another embodiment, the nuclei acid polymerase lacks 5' to 3' nuclease activity.

A variety of polymerases can be used in the methods of the invention. At least five families of DNA-dependent DNA polymerases are known, although most fall into families A, B and C. Most family A polymerases are single chain proteins that can contain multiple enzymatic functions including polymerase, 3' to 5' exonuclease activity and 5' to 3' exonuclease activity. Family B polymerases typically have a single catalytic domain with polymerase and 3' to 5' exonuclease activity, as well as accessory factors. Family C polymerases are typically multi-subunit proteins with polymerizing and 3' to 5' exonuclease activity.

In some embodiments, non-thermostable polymerases are useful. For example, the large fragment of *E. coli* DNA Polymerase I (Klenow) has 3' to 5' exonuclease activity and lacks 5' to 3' exonuclease activity. This enzyme or equivalent enzymes can be used in embodiments where the amplification reaction is not performed at high temperatures In some embodiments, the polymerase that provides the elongation activity may comprise a mutated exonuclease domain e.g., such as a hybrid polymerase, that lacks substantial 3' to 5' exonuclease activity. Such an enzyme has reduced exonuclease activity in comparison to a parent polymerase exonuclease domain.

In some embodiments, the invention provides thermostable nucleic acid polymerases substantially lacking 5' to 3' exonuclease activity. The polymerase include but are not limited to Pfu, exo– Pfu (a mutant form of Pfu that lacks 3' to 5' exonuclease activity), the Stoffel fragment of Taq, N-truncated Bst, N-truncated Bca, Genta, JdF3 exo–, Vent, Vent exo– (a mutant form of Vent that lacks 3' to 5' exonuclease activity), Deep Vent, Deep Vent exo– (a mutant form of Deep Vent that lacks 3' to 5' exonuclease activity), UlTma, and ThermoSequenase.

Nucleic acid polymerases useful according to the invention include both native polymerases as well as polymerase mutants, which lack polymerase activity or 3' nuclease activity. Nucleic acid polymerases useful according to the invention can possess different degrees of thermostability.

Additional nucleic acid polymerases with different degrees of thermostability useful according to the invention are listed below.

A. Bacteriophage DNA Polymerases (Useful for 37° C. Assays):

Bacteriophage DNA polymerases are devoid of 5' to 3' exonuclease activity, as this activity is encoded by a separate polypeptide. Examples of suitable DNA polymerases are T4, T7, and φ29 DNA polymerase. The enzymes available commercially are: T4 (available from many sources e.g., Epicentre) and T7 (available from many sources, e.g. Epicentre for unmodified and USB for 3' to 5' exo⁻T7 "Sequenase" DNA polymerase).

B. Archaeal DNA Polymerases:

There are 2 different classes of DNA polymerases which have been identified in archaea: 1. Family B/pol α type (homologs of Pfu from *Pyrococcus furiosus*) and 2. pol II type (homologs of *P. furiosus* DP1/DP2 2-subunit polymerase). DNA polymerases from both classes have been shown to naturally lack an associated 5' to 3' exonuclease activity and to possess 3' to 5' exonuclease (proofreading) activity. Suitable DNA polymerases (pol a or pol II) can be derived from archaea with optimal growth temperatures that are similar to the desired assay temperatures. Examples of suitable archaea include, but are not limited to:

1. Thermolabile (useful for 37° C. assays)—e.g., *Methanococcus voltae*

2. Thermostable (useful for non-PCR assays)—e.g., *Sulfolobus solfataricus, Sulfolobus acidocaldarium, Methanococcus jannaschi, Thermoplasma acidophilum*. It is estimated that suitable archaea exhibit maximal growth temperatures of ≦80-85° C. or optimal growth temperatures of ≦70-80° C.

3. Thermostable (useful for PCR assays)—e.g., *Pyrococcus* species (furiosus, species GB-D, species strain KOD1, woesii, abysii, horikoshii), *Thermococcus* species (litoralis, species 9° North-7, species JDF-3, gorgonarius), *Pyrodictium occultum*, and *Archaeoglobus fulgidus*. It is estimated that suitable archaea would exhibit maximal growth temperatures of ≧80-85° C. or optimal growth temperatures of ≧70-80° C. Appropriate PCR enzymes from the archaeal pol α DNA polymerase group are commercially available, including KOD (Toyobo), Pfx (Life Technologies, Inc.), Vent (New England BioLabs), Deep Vent (New England BioLabs), and Pwo (Boehringer-Mannheim).

Additional archaea related to those listed above are described in the following references: *Archaea: A Laboratory Manual* (Robb, F. T. and Place, A. R., eds.), Cold Spring Harbor Laboratory Press, Cold Spring Harbor, N.Y., 1995 and *Thermophilic Bacteria* (Kristjansson, J. K., ed.) CRC Press, Inc., Boca Raton, Fla., 1992.

C. Eubacterial DNA Polymerases:

There are 3 classes of eubacterial DNA polymerases, pol I, II, and III. Enzymes in the Pol I DNA polymerase family possess 5' to 3' exonuclease activity, and certain members also exhibit 3' to 5' exonuclease activity. Pol II DNA polymerases naturally lack 5' to 3' exonuclease activity, but do exhibit 3' to 5' exonuclease activity. Pol III DNA polymerases represent the major replicative DNA polymerase of the cell and are composed of multiple subunits. The pol III catalytic subunit lacks 5' to 3' exonuclease activity, but in some cases 3' to 5' exonuclease activity is located in the same polypeptide.

There are a variety of commercially available Pol I DNA polymerases, some of which have been modified to reduce or abolish 5' to 3' exonuclease activity. Methods used to eliminate 5' to 3' exonuclease activity of pol I DNA polymerases include:

mutagenesis (as described in Xu et al., 1997, *J. Mol. Biol.*, 268:284 and Kim et al., 1997, *Mol. Cells*, 7:468).

N-truncation by proteolytic digestion (as described in Klenow et al., 1971, *Eur. J. Biochem.*, 22: 371), or N-truncation by cloning and expressing as C-terminal fragments (as described in Lawyer et al., 1993, *PCR Methods Appl.*, 2:275).

As for archaeal sources, the assay-temperature requirements determine which eubacteria should be used as a source of a DNA polymerase useful according to the invention (e.g., mesophiles, thermophiles, hyperthermophiles).

1. Mesophilic/Thermolabile (Useful for 37° C. Assays)

i. DNA polymerases naturally substantially lacking 5' to 3' exonuclease activity: pol II or the pol III catalytic subunit from mesophilic eubacteria, such as *Escherichia coli, Streptococcus pneumoniae, Haemophilus influenza, Mycobacterium* species (*tuberculosis, leprae*)

ii. DNA polymerase mutants substantially lacking 5' to 3' exonuclease activity: Pol I DNA polymerases for N-truncation or mutagenesis can be isolated from the mesophilic eubacteria listed above (Ci). A commercially-available eubacterial DNA polymerase pol I fragment is the Klenow fragment (N-truncated *E. coli* pol I; Stratagene).

2. Thermostable (Useful for Non PCR Assays)

i. DNA polymerases naturally substantially lacking 5' to 3' exonuclease activity: Pol II or the pol III catalytic subunit from thermophilic eubacteria, such as *Bacillus* species (e.g., *stearothermophilus, caldotenax, caldovelox*)

ii. DNA polymerase mutants substantially lacking 5' to 3' exonuclease activity: Suitable pol I DNA polymerases for N-truncation or mutagenesis can be isolated from thermophilic eubacteria such as the *Bacillus* species listed above. Thermostable N-truncated fragments of *B. stearothermophilus* DNA polymerase pol I are commercially available and sold under the trade names Bst DNA polymerase I large fragment (Bio-Rad and Isotherm DNA polymerase (Epicentre)). A C-terminal fragment of *Bacillus caldotenax* pol I is available from Panvera (sold under the tradename Ladderman).

3. Thermostable (Useful for PCR Assays)

i. DNA polymerases naturally substantially lacking 5' to 3' exonuclease activity: Pol II or pol III catalytic subunit from *Thermus* species (*aquaticus, thermophilus, flavus, ruber, caldophilus, filiformis, brokianus*) or from *Thermotoga maritima*. The catalytic pol III subunits from *Thermus thermophilus* and *Thermus aquaticus* are described in Yi-Ping et al., 1999, *J. Mol. Evol.*, 48:756 and McHenry et al., 1997, *J. Mol. Biol.*, 272:178.

ii. DNA polymerase mutants substantially lacking 5' to 3' exonuclease activity: Suitable pol I DNA polymerases for N-truncation or mutagenesis can be isolated from a variety of thermophilic eubacteria, including *Thermus* species and *Thermotoga maritima* (see above). Thermostable fragments of *Thermus aquaticus* DNA polymerase pol I (Taq) are commercially available and sold under the trade names KlenTaq1 (Ab Peptides), Stoffel fragment (Perkin-Elmer), and *ThermoSequenase* (Amersham). In addition to C-terminal fragments, 5' to 3' exonuclease Taq mutants are also commercially available, such as TaqFS (Hoffman-LaRoche). In addition to 5'-3' exonuclease⁻ versions of Taq, an N-truncated version of *Thermotoga maritima* DNA polymerase I is also commercially available (tradename UlTma, Perkin-Elmer).

Additional eubacteria related to those listed above are described in *Thermophilic Bacteria* (Kristjansson, J. K., ed.) CRC Press, Inc., Boca Raton, Fla., 1992.

D. Eukaryotic 5' to 3' Exonuclease⁻ DNA polymerases (Useful for 37° C. Assays)

There are several DNA polymerases that have been identified in eukaryotes, including DNA pol α (replication/repair), δ (replication), ε (replication), β (repair) and γ (mitochondrial replication). Eukaryotic DNA polymerases are devoid of 5' to 3' exonuclease activity, as this activity is encoded by a separate polypeptide (e.g., mammalian FEN-1 or yeast RAD2). Suitable thermolabile DNA polymerases may be isolated from a variety of eukaryotes (including but not limited to yeast, mammalian cells, insect cells, *Drosophila*) and eukaryotic viruses (e.g., EBV, adenovirus).

Three 3' to 5' exonuclease motifs have been identified, and mutations in these regions have been shown to abolish 3' to 5' exonuclease activity in Klenow, φ29, T4, T7, and Vent DNA polymerases, yeast Pol α, Pol β, and Pol γ, and *Bacillus subtilis* Pol III (reviewed in Derbeyshire et al., 1995, Methods. Enzymol. 262:363).

Commercially-available enzymes that lack both 5' to 3' and 3' to 5' exonuclease activities include Sequenase (exo⁻ T7; USB), Pfu exo⁻ (Stratagene), exo⁻ Vent (New England BioLabs), exo⁺ DeepVent (New England BioLabs), exo⁻ Klenow fragment (Stratagene), Bst (Bio-Rad), Isotherm (Epicentre), Ladderman (Panvera), KlenTaqI (Ab Peptides), Stoffel fragment (Perkin-Elmer), ThermoSequenase (USB), and TaqFS (Hoffman-LaRoche).

Buffer and extension temperatures are selected to allow for optimal activity by the particular polymerase useful according to the invention. Buffers and extension temperatures useful for polymerases according to the invention are know in the art and can also be determined from the Vendor's specifications.

V. Nucleic Acids

A. Nucleic Acid Sequences Useful in the Invention

The invention provides for methods of detecting or measuring a target nucleic acid sequence; and also utilizes oligonucleotides probes for forming a cleavage structure according to the invention and optionally primers for amplifying a target nucleic acid sequence.

As used herein, the terms "nucleic acid", "polynucleotide" and "oligonucleotide" refer to primers, probes, and oligomer fragments to be detected, and shall be generic to polydeoxyribonucleotides (containing 2-deoxy-D-ribose), to polyribonucleotides (containing D-ribose), and to any other type of polynucleotide which is an N-glycoside of a purine or pyrimidine base, or modified purine or pyrimidine bases (including abasic sites). There is no intended distinction in length between the term "nucleic acid", "polynucleotide" and "oligonucleotide", and these terms will be used interchangeably. These terms refer only to the primary structure of the molecule. Thus, these terms include double- and single-stranded DNA, as well as double- and single-stranded RNA.

The complement of a nucleic acid sequence as used herein refers to an oligonucleotide which, when aligned with the nucleic acid sequence such that the 5' end of one sequence is paired with the 3' end of the other, is in "antiparallel association."

The oligonucleotide is not necessarily physically derived from any existing or natural sequence but may be generated in any manner, including chemical synthesis, DNA replication, reverse transcription or a combination thereof. The terms "oligonucleotide" or "nucleic acid" intend a polynucleotide of genomic DNA or RNA, cDNA, semisynthetic, or synthetic origin which, by virtue of its synthetic origin or manipulation: (1) is not associated with all or a portion of the polynucleotide with which it is associated in nature; and/or (2) is linked to a polynucleotide other than that to which it is linked in nature.

Oligonucleotides, according to the present invention, additionally comprise nucleic acid sequences which function as probes and can have secondary structure such as hairpins and stem-loops. Such oligonucleotide probes include, but are not limited to the molecular beacons, safteypins, scorpions, key probe and sunrise/amplifluor probes.

Because mononucleotides are reacted to make oligonucleotides in a manner such that the 5' phosphate of one mononucleotide pentose ring is attached to the 3' oxygen of its neighbor in one direction via a phosphodiester linkage, an end of oligonucleotide is referred to as the "5'end" if its 5' phosphate is not linked to the 3' oxygen of a mononucleotide pentose ring and as the "3'end" if its 3' oxygen is not linked to a 5' phosphate of a subsequent mononucleotide pentose ring. As used herein, a nucleic acid sequence, even if internal to a larger oligonucleotide, also may be said to have 5' and 3' ends.

When two different, non-overlapping oligonucleotides anneal to different regions of the same linear complementary nucleic acid sequence, and the 3' end of one oligonucleotide points toward the 5' end of the other, the former may be called the "upstream" oligonucleotide and the latter the "downstream" oligonucleotide.

Certain bases not commonly found in natural nucleic acids may be included in the nucleic acids of the present invention and include, for example, inosine and 7-deazaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength, and incidence of mismatched base pairs.

Stability of a nucleic acid duplex is measured by the melting temperature, or "$T_m$". The $T_m$ of a particular nucleic acid duplex under specified conditions is the temperature at which half of the base pairs have disassociated.

B. Primers and Probes Useful According to the Invention

The invention provides for oligonucleotide primers and probes useful for detecting or measuring a nucleic acid, for amplifying a target nucleic acid sequence, and for forming a cleavage structure according to the invention.

The term "primer" may refer to more than one primer and refers to an oligonucleotide, whether occurring naturally, as in a purified restriction digest, or produced synthetically, which is capable of acting as a point of initiation of synthesis along a complementary strand when placed under conditions in which synthesis of a primer extension product which is complementary to a nucleic acid strand is catalyzed. Such conditions include the presence of four different deoxyribonucleoside triphosphates and a polymerization-inducing agent such as DNA polymerase or reverse transcriptase, in a suitable buffer ("buffer" includes substituents which are cofactors, or which affect pH, ionic strength, etc.), and at a suitable temperature. The primer is preferably single-stranded for maximum efficiency in amplification.

Oligonucleotide primers useful according to the invention are single-stranded DNA or RNA molecules that are hybridizable to a template nucleic acid sequence and prime enzymatic synthesis of a second nucleic acid strand. The primer is complementary to a portion of a target molecule present in a pool of nucleic acid molecules. It is contemplated that oligonucleotide primers according to the invention are prepared by synthetic methods, either chemical or enzymatic. Alternatively, such a molecule or a fragment thereof is naturally-occurring, and is isolated from its natural source or purchased from a commercial supplier. Oligonucleotide primers and probes are 5 to 100 nucleotides in length, ideally from 8 to 30 nucleotides, although primers and probes of different length are of use. Primers for amplification are preferably about 8-30 nucleotides. Primers useful according to the invention are also designed to have a particular melting temperature (Tm)

by the method of melting temperature estimation. Commercial programs, including Oligo™, Primer Design and programs available on the internet, including Primer3 and Oligo Calculator can be used to calculate a Tm of a nucleic acid sequence useful according to the invention. Preferably, the Tm of an amplification primer useful according to the invention, as calculated for example by Oligo Calculator, is preferably between about 45 and 65° C. and more preferably between about 50 and 60° C. Preferably, the Tm of a probe useful according to the invention is 7° C. higher than the Tm of the corresponding amplification primers.

In one embodiment, a primer according to the invention is generated upon cleavage of the 3' flap of an oligonucleotide probe or a first oligonucleotide as defined herein.

Typically, selective hybridization occurs when two nucleic acid sequences are substantially complementary (at least about 65% complementary over a stretch of at least 8 to 25 nucleotides, preferably at least about 75%, more preferably at least about 90% complementary). See Kanehisa, M., 1984, Nucleic Acids Res. 12: 203, incorporated herein by reference. As a result, it is expected that a certain degree of mismatch at the priming site is tolerated. Such mismatch may be small, such as a mono-, di- or tri-nucleotide. Alternatively, a region of mismatch may encompass loops, which are defined as regions in which there exists a mismatch in an uninterrupted series of four or more nucleotides.

Numerous factors influence the efficiency and selectivity of hybridization of the primer to a second nucleic acid molecule. These factors, which include primer length, nucleotide sequence and/or composition, hybridization temperature, buffer composition and potential for steric hindrance in the region to which the primer is required to hybridize, will be considered when designing oligonucleotide primers according to the invention.

A positive correlation exists between primer length and both the efficiency and accuracy with which a primer will anneal to a target sequence. In particular, longer sequences have a higher melting temperature ($T_M$) than do shorter ones, and are less likely to be repeated within a given target sequence, thereby minimizing promiscuous hybridization. Primer sequences with a high G-C content or that comprise palindromic sequences tend to self-hybridize, as do their intended target sites, since unimolecular, rather than bimolecular, hybridization kinetics are generally favored in solution. However, it is also important to design a primer that contains sufficient numbers of G-C nucleotide pairings since each G-C pair is bound by three hydrogen bonds, rather than the two that are found when A and T bases pair to bind the target sequence, and therefore forms a tighter, stronger bond. Hybridization temperature varies inversely with primer annealing efficiency, as does the concentration of organic solvents, e.g. formamide, that might be included in a priming reaction or hybridization mixture, while increases in salt concentration facilitate binding. Under stringent annealing conditions, longer hybridization probes, or synthesis primers, hybridize more efficiently than do shorter ones, which are sufficient under more permissive conditions. Stringent hybridization conditions typically include salt concentrations of less than about 1M, more usually less than about 500 mM and preferably less than about 200 mM. Hybridization temperatures range from as low as 0° C. to greater than 22° C., greater than about 30° C., and (most often) in excess of about 37° C. Longer fragments may require higher hybridization temperatures for specific hybridization. As several factors affect the stringency of hybridization, the combination of parameters is more important than the absolute measure of a single factor.

Oligonucleotide primers can be designed with these considerations in mind and synthesized according to the following methods.

1. Oligonucleotide Primer Design Strategy

The design of a particular oligonucleotide primer for the purpose of sequencing or PCR involves selecting a sequence that is capable of recognizing the target sequence, but has a minimal predicted secondary structure. The oligonucleotide sequence binds only to a single site in the target nucleic acid sequence. Furthermore, the Tm of the oligonucleotide is optimized by analysis of the length and GC content of the oligonucleotide. Furthermore, when designing a PCR primer useful for the amplification of genomic DNA, the selected primer sequence does not demonstrate significant matches to sequences in the GenBank database (or other available databases).

The design of a primer is facilitated by the use of readily available computer programs, developed to assist in the evaluation of the several parameters described above and the optimization of primer sequences. Examples of such programs are "PrimerSelect" of the DNAStar™ software package (DNAStar, Inc.; Madison, Wis.), OLIGO 4.0 (National Biosciences, Inc.), PRIMER, Oligonucleotide Selection Program, PGEN and Amplify (described in Ausubel et al., 1995, Short Protocols in Molecular Biology, 3rd Edition, John Wiley & Sons).

2. Synthesis

The primers themselves are synthesized using techniques that are also well known in the art. Methods for preparing oligonucleotides of specific sequence are known in the art, and include, for example, cloning and restriction digest analysis of appropriate sequences and direct chemical synthesis. Once designed, oligonucleotides are prepared by a suitable chemical synthesis method, including, for example, the phosphotriester method described by Narang et al., 1979, Methods in Enzymology, 68:90, the phosphodiester method disclosed by Brown et al., 1979, Methods in Enzymology, 68:109, the diethylphosphoramidate method disclosed in Beaucage et al., 1981, Tetrahedron Letters, 22:1859, and the solid support method disclosed in U.S. Pat. No. 4,458,066, or by other chemical methods using either a commercial automated oligonucleotide synthesizer (which is commercially available) or VLSIPS™ technology.

C. Probes

The invention provides for probes useful for forming a labeled cleavage structure as defined herein. Methods of preparing a labeled cleavage structure according to the invention are provided in the section entitled "Cleavage Structure" herein.

As used herein, the term "probe" refers to a labeled oligonucleotide which forms a duplex structure with a sequence in the target nucleic acid, due to complementarity of at least one sequence in the probe with a sequence in the target region. Probe lengths useful in the invention are preferably 5-120, and more preferably 16-45 nucleotides in length. The probe, preferably, does not contain a sequence complementary to sequence(s) used in the primer extension (s), if such an extension is performed. Generally the 3' terminus of the probe will be "blocked" to prohibit incorporation of the probe into a primer extension product. "Blocking" can be achieved by using non-complementary bases or by adding a chemical moiety such as biotin or a phosphate group to the 3' hydroxyl of the last nucleotide, which may, depending upon the selected moiety, serve a dual purpose by also acting as a label for subsequent detection or capture of the nucleic acid attached to the label. Blocking can also be achieved by removing the 3'-OH or by using a nucleotide that lacks a 3'-OH such as dideoxynucleotide.

Additionally, according to the present invention, a probe can be an oligonucleotide with secondary structure such as a hairpin or a stem-loop, and includes, but is not limited to molecular beacons, safety pins, scorpions, key probes (described in U.S. application Ser. No. 11/351,129, filed Feb. 9, 2006, herein incorporated by reference in its entirety) and sunrise/amplifluor probes.

Molecular beacon probes comprise a hairpin, or stem-loop structure which possesses a pair of interactive signal generating labeled moieties (e.g., a fluorophore and a quencher) effectively positioned to quench the generation of a detectable signal. The loop comprises a region that is complementary to a target nucleic acid. The loop is flanked by 5' and 3' regions ("arms") that reversibly interact with one another by means of complementary nucleic acid sequences when the region of the probe that is complementary to a nucleic acid target sequence is not bound to the target nucleic acid. Alternatively, the loop is flanked by 5' and 3' regions ("arms") that reversibly interact with one another by means of attached members of an affinity pair to form a secondary structure when the region of the probe that is complementary to a nucleic acid target sequence is not bound to the target nucleic acid. As used herein, "arms" refers to regions of a probe that reversibly interact with one another by means of complementary nucleic acid sequences when the region of the probe that is complementary to a nucleic acid target sequence is not bound to the target nucleic acid or regions of a probe that reversibly interact with one another by means of attached members of an affinity pair to form a secondary structure when the region of the probe that is complementary to a nucleic acid target sequence is not bound to the target nucleic acid. When a molecular beacon probe is not hybridized to target, the arms hybridize with one another to form a stem hybrid, which is sometimes referred to as the "stem duplex". This is the closed conformation. When a molecular beacon probe hybridizes to its target the "arms" of the probe are separated. This is the open conformation. In the open conformation an arm may also hybridize to the target. Such probes may be free in solution, or they may be tethered to a solid surface. When the arms are hybridized (e.g., form a stem) the quencher is very close to the fluorophore and effectively quenches or suppresses its fluorescence, rendering the probe dark. Such probes are described in U.S. Pat. No. 5,925,517 and U.S. Pat. No. 6,037,130.

Key probes are a type of hairpin probe, wherein the probe comprises a first sequence that is at least partially complementary to a target sequence and a second sequence that is at least partially complementary to the first sequence. The probe further comprises a first moiety operatively coupled to the first sequence (e.g., a fluorophore) and a second moiety operatively coupled to the second sequence (e.g., a quencher). The first sequence and the second sequence are capable of hybridizing to each other when the probe is not hybridized to the target sequence, and hybridization of the probe to the target sequence causes either the first or second moiety to produce a detectable signal. Key probes are described in U.S. application Ser. No. 11/351,129, filed Feb. 9, 2006, herein incorporated by reference in its entirety.

D. Labeled Oligonucleotide Probes

Figure 3:
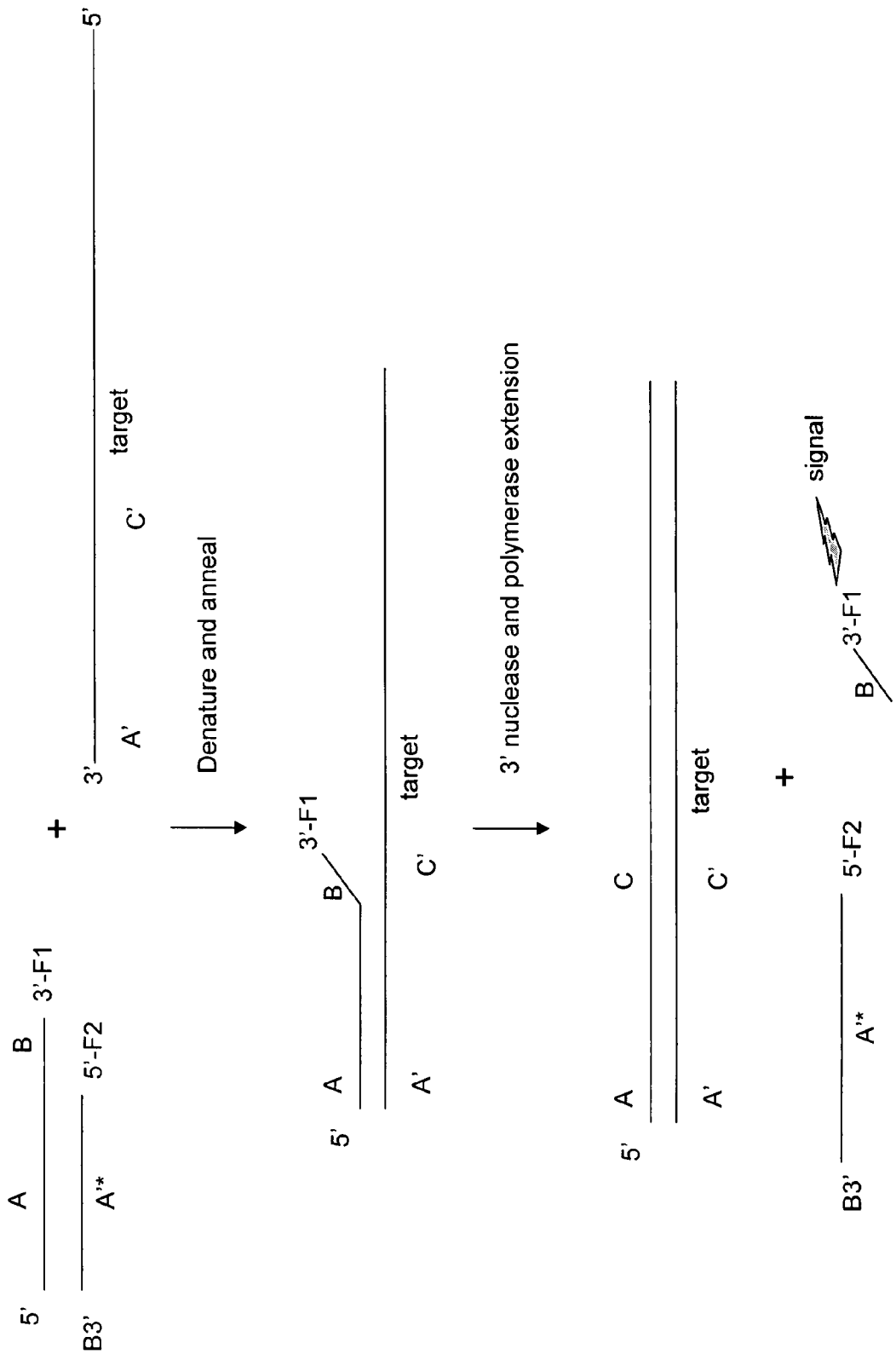
FIG. 3 illustrates one embodiment of the invention utilizing an oligonucleotide pair in which each oligonucleotide is coupled to a member of an interactive pair of labels (F1 and F2). Region A'* in the complementary oligo is not necessarily the same length or sequence as region A' in the template. Region A'* can be any portion of A' from 1-8 bases long or up to the full length of A'. It may also include sequence complimentary to region B.
Figure 4:
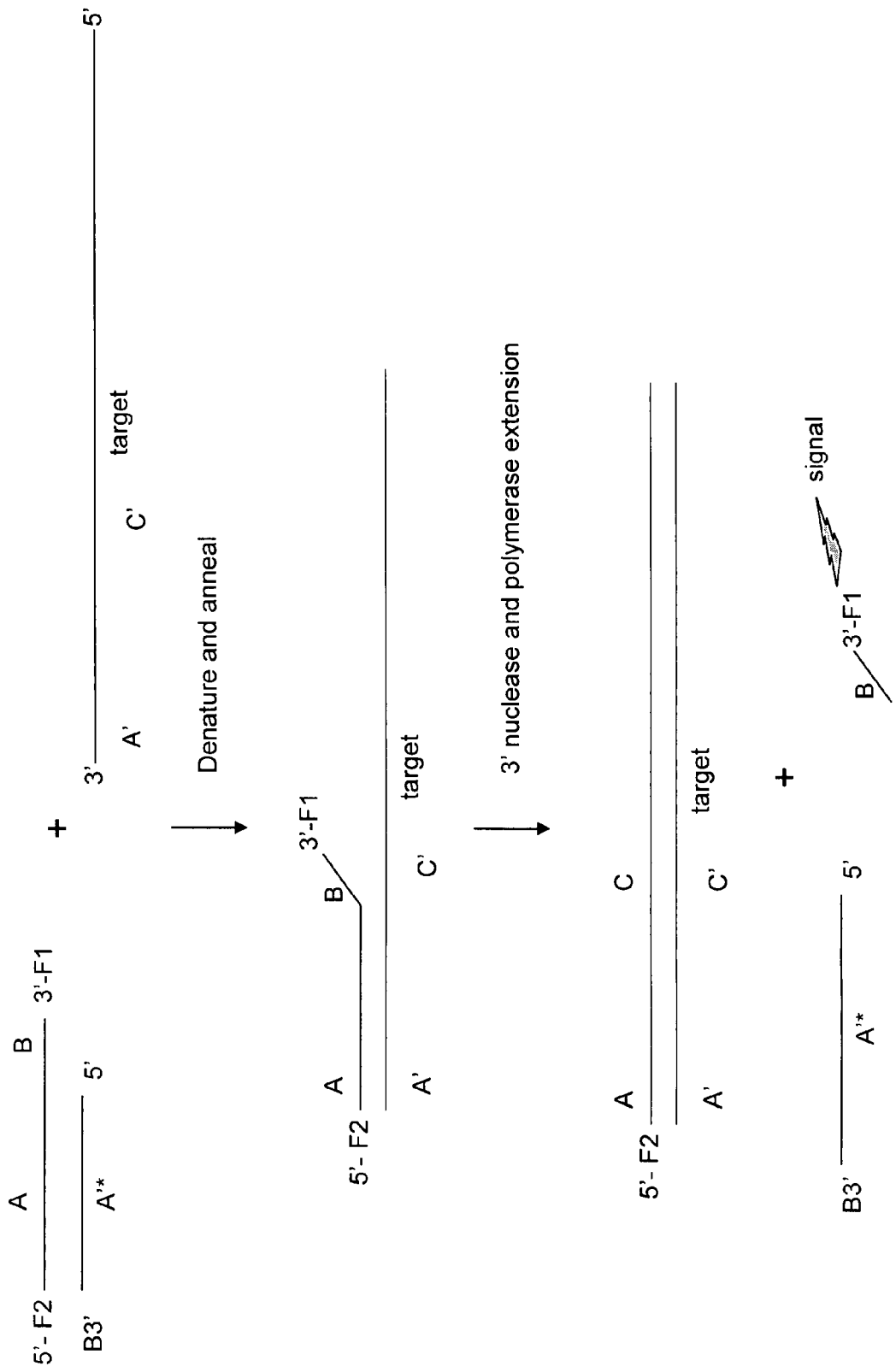
FIG. 4 illustrates one embodiment of the invention utilizing an oligonucleotide pair in which the first oligonucleotide is coupled to both members of an interactive pair of labels (F1 and F2). Region A'* in the complementary oligo is not necessarily the same length or sequence as region A' in the template. Region A'* can be any portion of A' from 1-8 or more bases long or up to the full length of A'. It may also include sequence complimentary to region B.

Also included in the invention is the use of a pair of labeled oligonucleotide probes (analogous to oligonucleotide probe pair AB/A'* shown in FIG. 3). It will be understood, however, based on the following description that the probe pair AB/A'* shown in FIG. 3 is non-limiting, and the specific configuration of a duplex of the first and second oligonucletoides may vary as described herein. The pair of oligonucleotide probes includes a first oligonucleotide probe comprising a 5' region that is complementary to a region of a target nucleic acid sequence and a 3' region that is not complementary to the target sequence. The 3' region can be 1, 2, 3, 4, 5, 6, 7, 8, 9, or 10 or more nucleotides in length, but is preferably in the range of 1 to 4 nucleotides in length, and is more preferably two or three nucleotides in length. A label, such as a first member of an interactive pair of labels is preferred to be operatively coupled to the 3' region of the first oligonucleotide. The label is preferably operatively coupled to the 3' terminal nucleotide of the first oligonucleotide. The pair of oligonucleotide probes also includes a second oligonucleotide probe that forms a duplex with said 5' region of said first oligonucleotide under non-denaturing conditions. The second oligonucleotide can be a quenched control (QC) or complementary oligonucleotide (CO) probes as described in the examples below. A second member of an interactive pair of labels can be operatively coupled to the second oligonucleotide. The interactive pair of labels can be an interactive pair such as those described herein, including a fluorophore/quencher pair. When the interactive pair is a fluorophore/quencher pair, the fluorophore and quencher can be operatively coupled to the first and second oligonucleotides, respectively, or can be operatively coupled to the second and first oligonucleotides, respectively. It will also be understood that either the first or second member of the interactive pair of labels can be operatively coupled to the target molecule to as to operatively interact with a member of the interactive pair operatively coupled to the first oligonucleotide.

The 5' region of the first oligonucleotide forms a duplex with said region of the second oligonucleotide under non-denaturing conditions, and it is preferred that at least one nucleotide in the 3' region of the first oligonucleotide is non-complementary to the second oligonucleotide. Preferably, at least one 3' terminal nucleotide of the first oligonucleotide is non-complementary to the second oligonucleotide.

As used herein, the phrase "at least a 3' nucleotide of the first oligonucleotide is non-complementary to the second oligonucleotide" refers to a condition in which at least one 3' terminal nucleotide does not hybridize to the second oligonucleotide. At least a 3' nucleotide of the first oligonucleotide being non-complementary preferably refers to a condition in which, when the first and second oligonucleotides are hybridized to form a duplex, at least one 3' terminal residue of the first oligonucleotide forms a 3' overhang or extension relative to the second oligonucleotide. For example, it is preferred that in a duplex between the first and second oligonucleotides that five 3' terminal nucleotides of the first oligonucleotide are non-complementary to the second oligonucleotide. FIG. 10A shows a non-limiting example of a configuration of the invention where five 3' terminal nucleotides of the first oligonucleotide are non-complementary to the second nucleotide.

In the schematic shown in FIG. 10A, the positions marked +1, +2, +3, +4, and +5 refer to the five 3' terminal nucleotides of the first oligonucleotide that are non-complementary to the second oligonucleotide. Similarly, the position marked −1 refers to the 3' most nucleotide of the first oligonucleotide that can be complementary to the second oligonucleotide. The position marked —X refers to additional nucleotides of the first oligonucleotide that can be complementary to the second oligonucleotide. —X can represent 7-100, 7-50, 9-15, or 0 nucleotides of the first oligonucleotide that are complementary to the second oligonucleotide. Those nucleotides represented, collectively, by —X and −1 that are complementary to the second oligonucleotide can be, but need not be contiguous (e.g., mismatched nucleotides can be included in the combination of —X and −1). Preferably —X and −1 collectively represent at least 8 nucleotides of the first oligonucleotide that are complementary to the second oligonucleotide (i.e., form a duplex with the second oligonucleotide). More preferably, the number of nucleotides of the first oligonucleotide collectively represented by —X and −1 that are complementary to, and form a duplex with the second oligonucleotide is such that, at a given reaction temperature, the stability of the hybrid formed between the first and second oligonucleotides is less than the stability of the hybrid formed between the first oligonucleotide and the target. That is, it is preferred that the number of nucleotides of the first oligonucleotide collectively represented by —X and −1 that are complementary to the second oligonucleotide is such that the Tm of a hybrid formed between the first and second oligonucleotides is less than the Tm of a hybrid formed between the first oligonucleotide and the target. Methods for designing probe/primer sequences with a specific Tm or for determining the Tm of a given oligonucleotide/oligonucleotide or oligonucleotide/target hybrid are known in the are and described hereinabove.

In addition, as shown above, the second oligonucleotide may include a region +A, where +A represents 0, 1, 2, 3, 4, 5, 6, 7, 8, 9, or 10 or more nucleotides of the 3' terminus of the second oligonucleotide that are non-complementary to and form a 3' overhang or extension relative to the 5' end of the first oligonucleotide. In addition, it is preferred that the 3' terminal nucleotide of the second oligonucleotide be a modified nucleotide that cannot be extended by a polymerase or other enzyme. Such modified nucleotides (e.g., a blocked nucleotide) are known in the art and are described herein.

While FIG. 10A shows five 3' nucleotides of the first oligonucleotide that are non-complementary to the second oligonucleotide, one to ten, preferably one to four 3' terminal nucleotides, and still more preferably one to five 5' terminal nucleotides of the first oligonucleotide can be non-complementary to the second oligonucleotide, although 6, 7, 8, 9, 10, 11, 12, 13, 14, 15, 16, 17, 18, 19, or 20 or more 3' terminal nucleotides of the first oligonucleotide can be non-complementary to the second oligonucleotide. In addition, at least one 3' terminal nucleotide of the second oligonucleotide can be non-complementary to the first oligonucleotide. More preferably at least four 3' terminal nucleotides, and still more preferably five 5' terminal nucleotides of the second oligonucleotide can be non-complementary to the first oligonucleotide, although 6, 7, 8, 9, 10, 11, 12, 13, 14, 15, 16, 17, 18, 19, or 20 or more 3' terminal nucleotides of the second oligonucleotide can be non-complementary to the first oligonucleotide (that is, in FIG. 10A, +A can represent 1-20 or more nucleotides that are non-complementary to the first oligonucleotide). Either or both of the first and second oligonucleotides can include modified nucleotides, such as LNA, that increase the binding Tm for the oligonucleotide pair and would, thus, permit a shorter region of complementarity between the first and second oligonucleotides.

It is preferred that the first oligonucleotide be labeled with a label, preferably a first member of an interactive pair of labels. It is preferred that the label is operatively coupled to the 3' terminal nucleotide of the first oligonucleotide. In one embodiment, both a first and second member of an interactive pair of labels are operatively coupled to the first oligonucleotide. One member of the pair of interactive labels is operatively coupled to the 3' terminal nucleotide of the first oligonucleotide, and the second member of the pair is operatively coupled to the first oligonucleotide at a position no more proximal to the 3' terminal nucleotide than position −1. The first member of the interactive pair of labels can be operatively coupled to the first oligonucleotide at the 3' terminal nucleotide, or based on the non-limiting example shown in FIG. 10A, at any of positions +1, +2, +3, +4, or +5. The second member of the pair of interactive labels can be operatively coupled to the first oligonucleotide at position −1, or at a position that is spaced 1-20 or more (e.g., 25-30) nucleotides 5' of position −1. The second member of the interactive pair of labels can be operatively coupled to the 5' terminal nucleotide of the first oligonucleotide. Alternatively, or in addition, a second member of an interactive pair of labels is operatively coupled to the second oligonucleotide. The second member of the interactive pair of labels can be operatively coupled to the 5' terminal nucleotide of the second oligonucleotide (i.e., at the nucleotide of the second oligonucleotide that is in opposition to the −1 position of the first oligonucleotide). Alternatively, the second member of the interactive pair of labels can be operatively coupled to the second oligonucleotide at a position 3' of the 5' terminus of the second oligonucleotide (e.g., 1-20, 2-25, 25-30) nucleotides 3' of the 5' terminus of the second oligonucleotide).

Figure 10B:
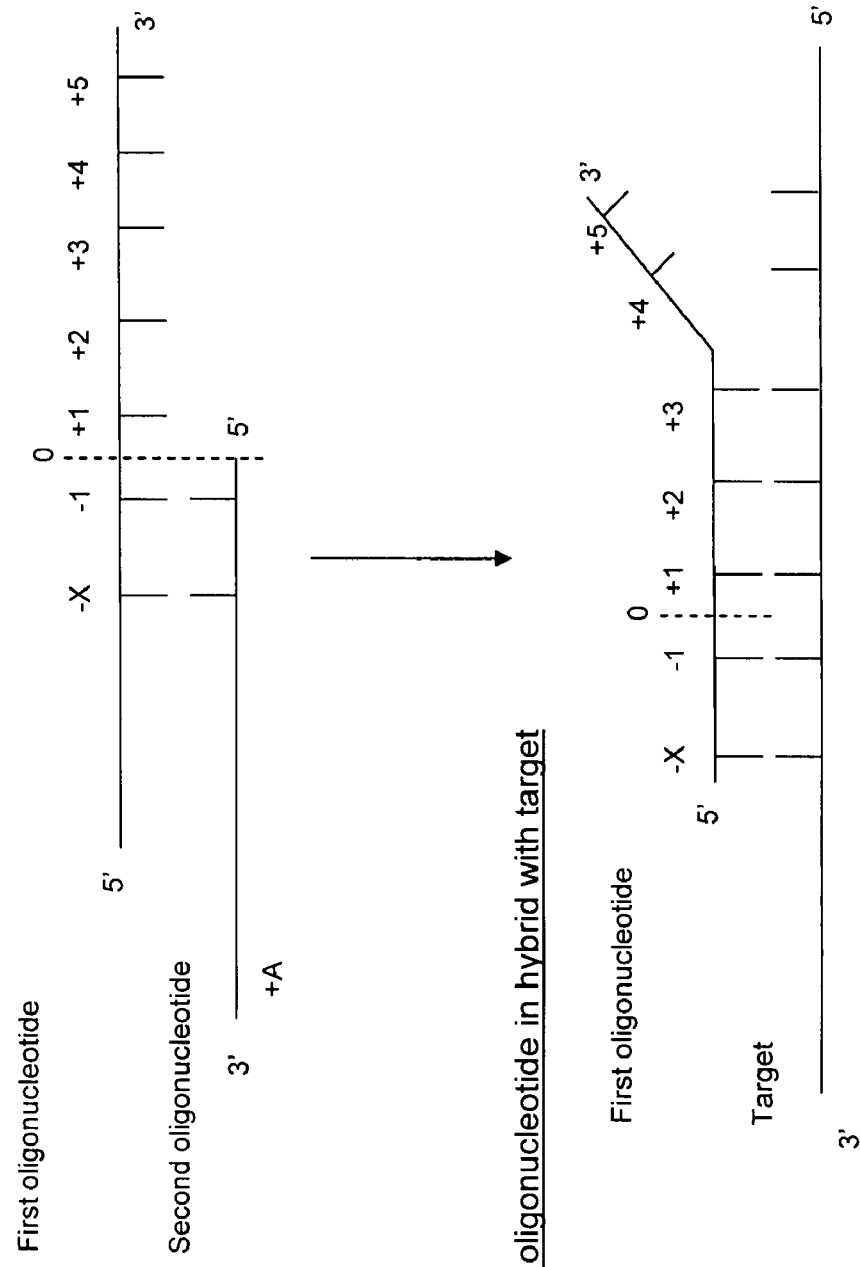
FIG. 10 shows an example of a configuration of a duplex formed between the first and second oligonucleotides described herein as well as the hybrid formed between the first oligonucleotide and the target nucleic acid.

Referring to the non-limiting example shown in FIG. 10A, the region represented collectively by +1, +2, +3, +4, and +5 is not necessarily the same as the 3' region of the first oligonucleotide that is non-complementary to a target. For example, where the 3' region of the first oligonucleotide is two nucleotides (i.e., a two nucleotide 3' flap), when hybridized to the target, the 3' region of the first oligonucleotide would consist of nucleotide positions +4 and +5. A schematic representation of a first oligonucleotide having five 3' terminal nucleotides that are non-complementary to the second oligonucleotide, and having a two nucleotide 3' flap when hybridized to a target nucleic acid is shown in FIG. 10B. Thus, if the first oligonucleotide has four 3' terminal nucleotides that are non-complementary to the second oligonucleotide in a duplex between the first and second oligonucleotides (i.e., nucleotide positions +1, +2, +3, and +4 of the first oligonucleotide are non-complementary to the second oligonucleotide), then in a hybrid with the target forming a two nucleotide 3' flap, nucleotides +3 and +4 of the first oligonucleotide form the 3' flap, while nucleotides +1 and +2 can be complementary to the target. Likewise, if the first oligonucleotide has six 3' terminal nucleotides that are non-complementary to the second oligonucleotide in a duplex between the first and second oligonucleotides (i.e., nucleotide positions +1, +2, +3, +4, +5, and +6) of the first oligonucleotide are non-complementary to the second oligonucleotide), then in a hybrid with the target forming a two nucleotide 3' flap, nucleotides +5 and +6 of the first oligonucleotide form the 3' flap, while nucleotides +1, +2, +3, and +4 can be complementary to the target.

Thus, in the non-limiting hypothetical example shown in FIG. 10B, a first member of an interactive pair or labels must be operatively coupled to either position +4 or +5 because positions +1, +2 and +3 would be complementary to the target sequence.

The use of complementary oligonucleotides (i.e., the second oligonucleotide in a labeled oligonucleotide pair) comprising quencher moieties are useful to decrease background signal generation in reactions described herein (e.g., real-time QPCR). In addition, however, without being bound to any one hypothesis, it is believed that a further advantage of using a the second oligonucleotide, whether labeled or unlabeled (e.g., whether operatively coupled to a quencher moiety or not) is that the second oligonucleotide may be able to reduce the formation of dimers of the first oligonucleotide or other unwanted priming events that may result in unwanted or premature cleavage of the 3' region of the first oligonucleotide. By forming a hybrid with the first oligonucleotide, the second oligonucleotide is able to form a duplex with the first oligonucleotide and make it less available for unwanted priming events.

E. Labels

The oligonucleotide probe is labeled, as described herein, by incorporating moieties detectable by spectroscopic, photochemical, biochemical, immunochemical, enzymatic or chemical means.

The method of linking or conjugating the label to the oligonucleotide probe depends, of course, on the type of label(s) used and the position of the label on the probe. Preferably a probe is labeled at the 3' end although probes labeled at the 5' end or labeled throughout the length of the probe are also useful in particular embodiments of the invention.

A variety of labels that would be appropriate for use in the invention, as well as methods for their inclusion in the probe, are known in the art and include, but are not limited to, enzymes (e.g., alkaline phosphatase and horseradish peroxidase) and enzyme substrates, radioactive atoms, fluorescent dyes, chromophores, chemiluminescent labels, electrochemiluminescent labels, such as Origen™ (Igen), that may interact with each other to enhance, alter, or diminish a signal. Of course, if a labeled molecule is used in a PCR based assay carried out using a thermal cycler instrument, the label must be able to survive the temperature cycling required in this automated process.

Among radioactive atoms, $^{33}P$ or, $^{32}P$ is preferred. Methods for introducing $^{33}P$ or, $^{32}P$ into nucleic acids are known in the art, and include, for example, 5' labeling with a kinase, or random insertion by nick translation. "Specific binding partner" refers to a protein capable of binding a ligand molecule with high specificity, as for example in the case of an antigen and a monoclonal antibody specific therefor. Other specific binding partners include biotin and avidin or streptavidin, IgG and protein A, and the numerous receptor-ligand couples known in the art. The above description is not meant to categorize the various labels into distinct classes, as the same label may serve in several different modes. For example, $^{125}I$ may serve as a radioactive label or as an electron-dense reagent. HRP may serve as an enzyme or as antigen for a monoclonal antibody. Further, one may combine various labels for desired effect. For example, one might label a probe with biotin, and detect the presence of the probe with avidin labeled with $^{125}I$, or with an anti-biotin monoclonal antibody labeled with HRP. Other permutations and possibilities will be readily apparent to those of ordinary skill in the art and are considered as equivalents within the scope of the instant invention.

Fluorophores for use as labels in constructing labeled probes of the invention include rhodamine and derivatives (such as Texas Red), fluorescein and derivatives (such as 5-bromomethyl fluorescein), Lucifer Yellow, IAEDANS, 7-Me$_2$N-coumarin-4-acetate, 7-OH-4-CH$_3$-coumarin-3-acetate, 7-NH$_2$-4-CH$_3$-coumarin-3-acetate (AMCA), monobromobimane, pyrene trisulfonates, such as Cascade Blue, and monobromorimethyl-ammoniobimane. In general, fluorophores with wide Stokes shifts are preferred, to allow using fluorimeters with filters rather than a monochromometer and to increase the efficiency of detection.

Probes labeled with fluorophores can readily be used in the cleavage structure according to the invention. If the label is on the 3'-end of the probe, the 3' nuclease generated labeled fragment is separated from the intact, hybridized probe by procedures well known in the art. The fluorescence of the released label is then compared to the label remaining bound to the target.

In one embodiment, the probe is labeled with a pair of interactive labels. As used herein "pair of interactive labels" as well as the phrase "first and second moieties" refer to a pair of molecules which operatively interact. As used herein, the term "operatively interacts" means that a pair of labels interacts physically, optically, or otherwise in such a manner as to permit detection of their proximity by means of a detectable signal. Examples of a "pair of interactive labels" include, but are not limited to, labels suitable for use in fluorescence resonance energy transfer (FRET) (Stryer, L. Ann. Rev. Biochem. 47, 819-846, 1978), scintillation proximity assays (SPA) (Hart and Greenwald, Molecular Immunology 16:265-267, 1979; U.S. Pat. No. 4,658,649), luminescence resonance energy transfer (LRET) (Mathis, G. Clin. Chem. 41, 1391-1397, 1995), direct quenching (Tyagi et al., Nature Biotechnology 16, 49-53, 1998), chemiluminescence energy transfer (CRET) (Campbell, A. K., and Patel, A. Biochem. J. 216, 185-194, 1983), bioluminescence resonance energy transfer (BRET) (Xu, Y., Piston D. W., Johnson, Proc. Natl. Acad. Sc., 96, 151-156, 1999), or excimer formation (Lakowicz, J. R. Principles of Fluorescence Spectroscopy, Kluwer Academic/Plenum Press, New York, 1999).

A pair of interactive labels useful for the invention can comprise a pair of FRET-compatible dyes, or a quencher-dye pair. In one embodiment, the pair comprises a fluorophore-quencher pair.

Oligonucleotide probes of the present invention permit detection of a target nucleic acid. They can be labeled with a fluorophore and quencher in such a manner that the fluorescence emitted by the fluorophore in intact probes (e.g., non-cleaved and/or non-denatured) is substantially quenched, whereas the fluorescence in cleaved or target hybridized oligonucleotide probes are not quenched, resulting in an increase in overall fluorescence upon probe cleavage or target hybridization. Furthermore, the generation of a fluorescent signal during real-time detection of the amplification products allows accurate quantitation of the initial number of target sequences in a sample.

In one embodiment, a fluorophore of an interactive pair is operatively coupled to the 3' end of a probe molecule, preferably a fluorophore is linked to the 3' portion of a probe molecule that is not complementary to the target sequence (e.g., forming the 3' flap). The fluorophore or other detectable moiety can be operatively coupled to the 3' terminal nucleotide of a probe molecule, and can be coupled, using methods known to those of skill in the art, to either the 3' terminal base, or free 3' OH group. It is preferred that a member of an interactive pair is operatively coupled to the 3' OH group of the 3' terminal nucleotide in a probe molecule. It is also possible to include a second member of an interactive pair of label moieties (e.g., a quencher) in the probe molecule. A quencher moiety can be operatively coupled to the 5' end of the probe molecule, or can be linked to the probe molecule at a position closer to the 3' flap. For example, a quencher moiety can be operatively coupled to the oligonucleotide so as to be interactively operative (e.g., in the range of 2 to 20 or more bases 5' of the 3' region, up to and including being operatively coupled to the 5' terminal nucleotide of an oligonucleotide).

A wide variety of fluorophores can be used, including but not limited to: 5-FAM (also called 5-carboxyfluorescein; also called Spiro(isobenzofuran-1(3H), 9'-(9H)xanthene)-5-carboxylic acid, 3',6'-dihydroxy-3-oxo-6-carboxyfluorescein); 5-Hexachloro-Fluorescein([4,7,2',4',5',7'-hexachloro-(3',6'-dipivaloyl-fluoresceinyl)-6-carboxylic acid]); 6-Hexachloro-Fluorescein ([4,7,2',4',5',7'-hexachloro-(3',6'-dipivaloylfluoresceinyl)-5-carboxylic acid]); 5-Tetrachloro-Fluorescein ([4,7,2',7'-tetra-chloro-(3',6'-dipivaloylfluoresceinyl)-5-carboxylic acid]); 6-Tetrachloro-Fluorescein([4,7,2',7'-tetrachloro-(3',6'-dipivaloylfluoresceinyl)-6-carboxylic acid]); 5-TAMRA (5-carboxytetramethylrhodamine; Xanthylium, 9-(2,4-dicarboxyphenyl)-3,6-bis(dimethyl-amino); 6-TAMRA (6-carboxytetramethylrhodamine; Xanthylium, 9-(2,5-dicarboxyphenyl)-3,6-bis(dimethylamino); EDANS (5-((2-aminoethyl)amino)naphthalene-1-sulfonic acid); 1,5-IAEDANS (5-((((2-iodoacetyl)amino)ethyl)amino)naphthalene-1-sulfonic acid); DABCYL (4-((4-(dimethylamino) phenyl) azo)benzoic acid) Cy5 (Indodicarbocyanine-5) Cy3 (Indo-dicarbocyanine-3); and BODIPY FL (2,6-dibromo-4, 4-difluoro-5,7-dimethyl-4-bora-3a, 4a-diaza-s-indacene-3-proprionic acid), Quasar-670 (Bioresearch Technologies), CalOrange (Bioresearch Technologies), Rox, as well as suitable derivatives thereof.

As used herein, the term "quencher" refers to a chromophoric molecule or part of a compound, which is capable of reducing the emission from a fluorescent donor when attached to or in proximity to the donor. Quenching may occur by any of several mechanisms including fluorescence resonance energy transfer, photoinduced electron transfer, paramagnetic enhancement of intersystem crossing, Dexter exchange coupling, and excitation coupling such as the formation of dark complexes. Fluorescence is "quenched" when the fluorescence emitted by the fluorophore is reduced as compared with the fluorescence in the absence of the quencher by at least 10%, for example, 15%, 20%, 30%, 40%, 50%, 60%, 70%, 80%, 90%, 95%, 98%, 99%, 99.9% or more The quencher can be any material that can quench at least one fluorescence emission from an excited fluorophore being used in the assay. There is a great deal of practical guidance available in the literature for selecting appropriate reporter-quencher pairs for particular probes, as exemplified by the following references: Clegg (1993, Proc. Natl. Acad. Sci., 90:2994-2998); Wu et al. (1994, Anal. Biochem., 218:1-13); Pesce et al., editors, Fluorescence Spectroscopy (1971, Marcel Dekker, New York); White et al., Fluorescence Analysis: A Practical Approach (1970, Marcel Dekker, New York); and the like. The literature also includes references providing exhaustive lists of fluorescent and chromogenic molecules and their relevant optical properties for choosing reporter-quencher pairs, e.g., Berlman, Handbook of Fluorescence Spectra of Aromatic Molecules, 2nd Edition (1971, Academic Press, New York); Griffiths, Colour and Constitution of Organic Molecules (1976, Academic Press, New York); Bishop, editor, Indicators (1972, Pergamon Press, Oxford); Haugland, Handbook of Fluorescent Probes and Research Chemicals (1992 Molecular Probes, Eugene) Pringsheim, Fluorescence and Phosphorescence (1949, Interscience Publishers, New York), all of which incorporated hereby by reference. Further, there is extensive guidance in the literature for derivatizing reporter and quencher molecules for covalent attachment via common reactive groups that can be added to an oligonucleotide, as exemplified by the following references, see, for example, Haugland (cited above); Ullman et al., U.S. Pat. No. 3,996,345; Khanna et al., U.S. Pat. No. 4,351,760, all of which are hereby incorporated by reference.

A number of commercially available quenchers are known in the art, and include but are not limited to DABCYL, BHQ-1, BHQ-2, and BHQ-3. The BHQ ("Black Hole Quenchers") quenchers are a new class of dark quenchers that prevent fluorescence until a hybridization event occurs. In addition, these new quenchers have no native fluorescence, virtually eliminating background problems seen with other quenchers. BHQ quenchers can be used to quench almost all reporter dyes and are commercially available, for example, from Biosearch Technologies, Inc (Novato, Calif.).

In one preferred embodiment, the probe is labeled with a pair of interactive labels. It is not necessary to separate the 3' nuclease generated fragment and the probe that remains bound to the target after cleavage in the presence of the 3' nuclease if the probe is synthesized with a fluorophore, usually at the 3'-end, and a quencher which is close enough to the fluorophore so that the labels interact. Such a dual labeled probe will not fluoresce when intact because the light emitted from the dye is quenched by the quencher. Thus, any fluorescence emitted by an intact probe is considered to be background fluorescence. When a labeled probe is cleaved by a 3' nuclease, dye and quencher are separated and a detectable signal will be generated. The amount of fluorescence is proportional to the amount of nucleic acid target sequence present in a sample.

In some embodiments, the pair of interactive labels are on two separate oligonucleotides (e.g., a first oligonucleotide and a second oligonucleotide). The labels interact when the two oligonucleotides hybridize and do not interact, and therefore produce a detectable signal, when the oligonucleotides are cleaved and/or denatured. Where the interactive pair of labels are a fluorophore/quencher pair, the fluorophore may be operatively coupled to either the first or second oligonucleotide probe, and the quencher can be operatively coupled to the other oligonucleotide probe.

In some situations, one can use two interactive labels on a single oligonucleotide with due consideration given for maintaining an appropriate spacing of the labels on the oligonucleotides to permit the separation of the labels during oligonucleotide hydrolysis.

In another embodiment of the invention, detection of the hydrolyzed, labeled probe can be accomplished using, for example, fluorescence polarization, and a technique to differentiate between large and small molecules based on molecular tumbling. Large molecules (i.e., intact labeled probe) tumble in solution much more slowly than small molecules. Upon linkage of a fluorescent moiety to the molecule of interest (e.g., the 5' end of a labeled probe), this fluorescent moiety can be measured (and differentiated) based on molecular tumbling, thus differentiating between intact and digested probe.

Although probe sequence can be selected to achieve important benefits, one can also realize important advantages by selection of probe labels(s). The labels may be attached to the oligonucleotide directly or indirectly by a variety of techniques. Depending on the precise type of label used, the label can be located at the 5' or 3' end of the probe, located internally in the probe, or attached to spacer arms of various sizes and compositions to facilitate signal interactions. Using commercially available phosphoramidite reagents, one can produce oligomers containing functional groups (e.g., thiols or primary amines) at either the 5- or the 3-terminus via an appropriately protected phosphoramidite, and can label them using protocols described in, for example, PCR Protocols: A Guide to Methods and Applications, Innis et al., eds. Academic Press, Ind., 1990.

Methods for introducing oligonucleotide functionalizing reagents to introduce one or more sulfhydryl, amino or hydroxyl moieties into the oligonucleotide probe sequence, typically at the 5' terminus, are described in U.S. Pat. No. 4,914,210. A 5' phosphate group can be introduced as a radioisotope by using polynucleotide kinase and gamma-$^{32}$P-ATP or gamma-$^{33}$P-ATP to provide a reporter group. Biotin can be added to the 5' end by reacting an aminothymidine residue, or a 6-amino hexyl residue, introduced during synthesis, with an N-hydroxysuccinimide ester of biotin. Labels at the 3' terminus may employ polynucleotide terminal transferase to add the desired moiety, such as for example, cordycepin $^{35}$S-dATP, and biotinylated dUTP.

Oligonucleotide derivatives are also available labels. For example, etheno-dA and etheno-A are known fluorescent adenine nucleotides that can be incorporated into a nucleic acid probe. Similarly, etheno-dC or 2-amino purine deoxyriboside is another analog that could be used in probe synthesis. The probes containing such nucleotide derivatives may be hydrolyzed to release much more strongly fluorescent mononucleotides by flap-specific nuclease activity.

Methods of labeling a probe according to the invention and suitable labels are described below in the section entitled "Cleavage Structure".

D. Production of a Nucleic Acid

The invention provides nucleic acids to be detected and or measured, for amplification of a target nucleic acid sequence and for formation of a cleavage structure.

The present invention utilizes nucleic acids comprising RNA, cDNA, genomic DNA, synthetic forms, and mixed polymers. The invention includes both sense and antisense strands of a nucleic acid. According to the invention, the nucleic acid may be chemically or biochemically modified or may contain non-natural or derivatized nucleotide bases. Such modifications include, for example, labels, methylation, substitution of one or more of the naturally occurring nucleotides with an analog, internucleotide modifications such as uncharged linkages (e.g. methyl phosphonates, phosphorodithioates, etc.), pendent moieties (e.g., polypeptides), intercalators, (e.g. acridine, psoralen, etc.) chelators, alkylators, and modified linkages (e.g. alpha anomeric nucleic acids, etc.) Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

1. Nucleic Acids Comprising DNA a. Cloning

Nucleic acids comprising DNA can be isolated from cDNA or genomic libraries by cloning methods well known to those skilled in the art (Ausubel et al., supra). Briefly, isolation of a DNA clone comprising a particular nucleic acid sequence involves screening a recombinant DNA or cDNA library and identifying the clone containing the desired sequence. Cloning will involve the following steps. The clones of a particular library are spread onto plates, transferred to an appropriate substrate for screening, denatured, and probed for the presence of a particular nucleic acid. A description of hybridization conditions, and methods for producing labeled probes is included below.

The desired clone is preferably identified by hybridization to a nucleic acid probe or by expression of a protein that can be detected by an antibody. Alternatively, the desired clone is identified by polymerase chain amplification of a sequence defined by a particular set of primers according to the methods described below.

The selection of an appropriate library involves identifying tissues or cell lines that are an abundant source of the desired sequence. Furthermore, if a nucleic acid of interest contains regulatory sequence or intronic sequence a genomic library is screened (Ausubel et al., supra).

b. Genomic DNA

Nucleic acid sequences of the invention are amplified from genomic DNA. Genomic DNA is isolated from tissues or cells according to the following method.

To facilitate detection of a variant form of a gene from a particular tissue, the tissue is isolated free from surrounding normal tissues. To isolate genomic DNA from mammalian tissue, the tissue is minced and frozen in liquid nitrogen. Frozen tissue is ground into a fine powder with a prechilled mortar and pestle, and suspended in digestion buffer (100 mM NaCl, 10 mM Tris-HCl, pH 8.0, 25 mM EDTA, pH 8.0, 0.5% (w/v) SDS, 0.1 mg/ml proteinase K) at 1.2 ml digestion buffer per 100 mg of tissue. To isolate genomic DNA from mammalian tissue culture cells, cells are pelleted by centrifugation for 5 min at 500×g, resuspended in 1-10 ml ice-cold PBS, repelleted for 5 min at 500×g and resuspended in 1 volume of digestion buffer.

Samples in digestion buffer are incubated (with shaking) for 12-18 hours at 50° C., and then extracted with an equal volume of phenol/chloroform/isoamyl alcohol. If the phases are not resolved following a centrifugation step (10 min at 1700×g), another volume of digestion buffer (without proteinase K) is added and the centrifugation step is repeated. If a thick white material is evident at the interface of the two phases, the organic extraction step is repeated. Following extraction the upper, aqueous layer is transferred to a new tube to which will be added ½ volume of 7.5M ammonium acetate and 2 volumes of 100% ethanol. The nucleic acid is pelleted by centrifugation for 2 min at 1700×g, washed with 70% ethanol, air dried and resuspended in TE buffer (10 mM Tris-HCl, pH 8.0, 1 mM EDTA, pH 8.0) at 1 mg/ml. Residual RNA is removed by incubating the sample for 1 hour at 37° C. in the presence of 0.1% SDS and 1 µg/ml DNase-free RNase, and repeating the extraction and ethanol precipitation steps. The yield of genomic DNA, according to this method is expected to be approximately 2 mg DNA/1 g cells or tissue (Ausubel et al., supra). Genomic DNA isolated according to this method can be used for PCR analysis, according to the invention.

c. Restriction Digest (of cDNA or Genomic DNA)

Following the identification of a desired cDNA or genomic clone containing a particular target nucleic acid sequence, nucleic acids of the invention may be isolated from these clones by digestion with restriction enzymes.

The technique of restriction enzyme digestion is well known to those skilled in the art (Ausubel et al., supra). Reagents useful for restriction enzyme digestion are readily available from commercial vendors including Stratagene, as well as other sources.

d. PCR

Nucleic acids of the invention may be amplified from genomic DNA or other natural sources by the polymerase chain reaction (PCR). PCR methods are well-known to those skilled in the art.

PCR provides a method for rapidly amplifying a particular DNA sequence by using multiple cycles of DNA replication catalyzed by a thermostable, DNA-dependent DNA polymerase to amplify the target sequence of interest. PCR requires the presence of a target nucleic acid sequence to be amplified, two single stranded oligonucleotide primers flanking the sequence to be amplified, a DNA polymerase, deoxyribonucleoside triphosphates, a buffer and salts.

PCR, is performed as described in Mullis and Faloona, 1987, Methods Enzymol., 155: 335, herein incorporated by reference.

The polymerase chain reaction (PCR) technique, is disclosed in U.S. Pat. Nos. 4,683,202, 4,683,195 and 4,800,159. In its simplest form, PCR is an in vitro method for the enzymatic synthesis of specific DNA sequences, using two oligonucleotide primers that hybridize to opposite strands and flank the region of interest in the target DNA. A repetitive series of reaction steps involving template denaturation, primer annealing and the extension of the annealed primers by DNA polymerase results in the exponential accumulation of a specific fragment whose termini are defined by the 5' ends of the primers. PCR is reported to be capable of producing a selective enrichment of a specific DNA sequence by a factor of 109. The PCR method is also described in Saiki et al., 1985, *Science* 230:1350.

PCR is performed using template DNA (at least 1 fg; more usefully, 1-1000 ng) and at least 25 pmol of oligonucleotide primers. A typical reaction mixture includes: 2 µl of DNA, 25 pmol of oligonucleotide primer, 2.5 µl of a suitable buffer, 0.4 µl of 1.25 µM dNTP, 2.5 units of Taq DNA polymerase (Stratagene) and deionized water to a total volume of 25 µl. Mineral oil is overlaid and the PCR is performed using a programmable thermal cycler.

The length and temperature of each step of a PCR cycle, as well as the number of cycles, are adjusted according to the stringency requirements in effect. Annealing temperature and timing are determined both by the efficiency with which a primer is expected to anneal to a template and the degree of mismatch that is to be tolerated. The ability to optimize the stringency of primer annealing conditions is well within the knowledge of one of moderate skill in the art. An annealing temperature of between 30° C. and 72° C. is used. Initial denaturation of the template molecules normally occurs at between 92° C. and 99° C. for 4 minutes, followed by 20-40 cycles consisting of denaturation (94-99° C. for 15 seconds to 1 minute), annealing (temperature determined as discussed above; 1-2 minutes), and extension (72° C. for 1 minute). The final extension step is generally carried out for 4 minutes at 72° C., and may be followed by an indefinite (0-24 hour) step at 4° C.

Detection methods generally employed in standard PCR techniques use a labeled probe with the amplified DNA in a hybridization assay. Preferably, the probe is labeled, e.g., with $^{32}P$, biotin, horseradish peroxidase (HRP), etc., to allow for detection of hybridization.

Other means of detection include the use of fragment length polymorphism (PCR FLP), hybridization to allele-specific oligonucleotide (ASO) probes (Saiki et al., 1986, *Nature* 324:163), or direct sequencing via the dideoxy method (using amplified DNA rather than cloned DNA). The standard PCR technique operates (essentially) by replicating a DNA sequence positioned between two primers, providing as the major product of the reaction a DNA sequence of discrete length terminating with the primer at the 5' end of each strand. Thus, insertions and deletions between the primers result in product sequences of different lengths, which can be detected by sizing the product in PCR-FLP. In an example of ASO hybridization, the amplified DNA is fixed to a nylon filter (by, for example, UV irradiation) in a series of "dot blots", then allowed to hybridize with an oligonucleotide probe labeled with HRP under stringent conditions. After washing, tetramethylbenzidine (TMB) and hydrogen peroxide are added: HRP oxidizes the hydrogen peroxide, which in turn oxidizes the TMB to a blue precipitate, indicating a hybridized probe.

A PCR assay for detecting or measuring a nucleic assay according to the invention is described in the section entitled "Methods of Use".

2. Nucleic Acids Comprising RNA

The present invention also provides a nucleic acid comprising RNA.

Nucleic acids comprising RNA can be purified according to methods well known in the art (Ausubel et al., supra). Total RNA can be isolated from cells and tissues according to methods well known in the art (Ausubel et al., supra) and described below.

RNA is purified from mammalian tissue according to the following method. Following removal of the tissue of interest, pieces of tissue of ≦2 g are cut and quick frozen in liquid nitrogen, to prevent degradation of RNA. Upon the addition of a suitable volume of guanidinium solution (for example 20 ml guanidinium solution per 2 g of tissue), tissue samples are ground in a tissuemizer with two or three 10-second bursts. To prepare tissue guanidinium solution (1 L) 590.8 g guanidinium isothiocyanate is dissolved in approximately 400 ml DEPC-treated $H_2O$. 25 ml of 2 M Tris-HCl, pH 7.5 (0.05 M final) and 20 ml $Na_2EDTA$ (0.01 M final) is added, the solution is stirred overnight, the volume is adjusted to 950 ml, and 50 ml 2-ME is added.

Homogenized tissue samples are subjected to centrifugation for 10 min at 12,000×g at 12° C. The resulting supernatant is incubated for 2 min at 65° C. in the presence of 0.1 volume of 20% Sarkosyl, layered over 9 ml of a 5.7M CsCl solution (0.1 g CsCl/ml), and separated by centrifugation overnight at 113,000×g at 22° C. After careful removal of the supernatant, the tube is inverted and drained. The bottom of the tube (containing the RNA pellet) is placed in a 50 ml plastic tube and incubated overnight (or longer) at 4° C. in the presence of 3 ml tissue resuspension buffer (5 mM EDTA, 0.5% (v/v) Sarkosyl, 5% (v/v) 2-ME) to allow complete resuspension of the RNA pellet. The resulting RNA solution is extracted sequentially with 25:24:1 phenol/chloroform/isoamyl alcohol, followed by 24:1 chloroform/isoamyl alcohol, precipitated by the addition of 3 M sodium acetate, pH 5.2, and 2.5 volumes of 100% ethanol, and resuspended in DEPC water (Chirgwin et al., 1979, *Biochemistry*, 18: 5294).

Alternatively, RNA is isolated from mammalian tissue according to the following single step protocol. The tissue of interest is prepared by homogenization in a glass teflon homogenizer in 1 ml denaturing solution (4M guanidinium thiosulfate, 25 mM sodium citrate, pH 7.0, 0.1M 2-ME, 0.5% (w/v) N-laurylsarkosine) per 100 mg tissue. Following transfer of the homogenate to a 5-ml polypropylene tube, 0.1 ml of 2 M sodium acetate, pH 4, 1 ml water-saturated phenol, and 0.2 ml of 49:1 chloroform/isoamyl alcohol are added sequentially. The sample is mixed after the addition of each component, and incubated for 15 min at 0-4° C. after all components have been added. The sample is separated by centrifugation for 20 min at 10,000×g, 4° C., precipitated by the addition of 1 ml of 100% isopropanol, incubated for 30 minutes at −20° C. and pelleted by centrifugation for 10 minutes at 10,000×g, 4° C. The resulting RNA pellet is dissolved in 0.3 ml denaturing solution, transferred to a microfuge tube, precipitated by the addition of 0.3 ml of 100% isopropanol for 30 minutes at −20° C., and centrifuged for 10 minutes at 10,000×g at 4° C. The RNA pellet is washed in 70% ethanol, dried, and resuspended in 100-200 µl DEPC-treated water or DEPC-treated 0.5% SDS (Chomczynski and Sacchi, 1987, *Anal. Biochem.*, 162: 156).

Nucleic acids comprising RNA can be produced according to the method of in vitro transcription.

The technique of in vitro transcription is well known to those of skill in the art. Briefly, the gene of interest is inserted into a vector containing an SP6, T3 or T7 promoter. The vector is linearized with an appropriate restriction enzyme that digests the vector at a single site located downstream of the coding sequence. Following a phenol/chloroform extraction, the DNA is ethanol precipitated, washed in 70% ethanol, dried and resuspended in sterile water. The in vitro transcription reaction is performed by incubating the linearized DNA with transcription buffer (200 mM Tris-HCl, pH 8.0, 40 mM MgCl$_2$, 10 mM spermidine, 250 NaCl [T7 or T3] or 200 mM Tris-HCl, pH 7.5, 30 mM MgCl$_2$, 10 mM spermidine [SP6]), dithiothreitol, RNase inhibitors, each of the four ribonucleoside triphosphates, and either SP6, T7 or T3 RNA polymerase for 30 min at 37° C. To prepare a radiolabeled polynucleotide comprising RNA, unlabeled UTP will be omitted and $^{35}$S—UTP will be included in the reaction mixture. The DNA template is then removed by incubation with DNaseI. Following ethanol precipitation, an aliquot of the radiolabeled RNA is counted in a scintillation counter to determine the cpm/µl (Ausubel et al., supra).

Alternatively, nucleic acids comprising RNA are prepared by chemical synthesis techniques such as solid phase phosphoramidite (described above).

3. Nucleic Acids Comprising Oligonucleotides

A nucleic acid comprising oligonucleotides can be made by using oligonucleotide synthesizing machines which are commercially available (described above).

EXAMPLES

Example 1

Optimal 3' Flap Length

The following experiments were conducted to determine the optimal 3' flap length for generating a detectable signal. One of eight different targets were added to each reaction mixture (See FIG. 2A). Each target was designed to have from 0-7 nucleotides that are non-complementary to the 3' region of the probe, so as to form a 3' flap in the probe. One of skill in the art would appreciate that these experiments could have been performed by adding a single target and varying the complementarity of the nucleotides at the 3' end of the probe to arrive at the same result.

The probes were labeled with an interactive pair of labels: BHQ2 at the 5' end and FAM at the 3' end. FAM was either directly coupled to the 3' OH or to the 3' terminal base. The cleavage reactions were performed in a 25 ul reaction volume containing the following:

200 nM of one of Targets 1-8 (See FIG. 2)
  200 nM of Probe 1A having (Fam on 3' OH; BHQ2 on 5' end) OR
  200 nM of Probe 1A having (Fam on the 3' base; BHQ2 on 5' end)
  1× Probe buffer (15 mM of Tris-HCL (pH8), 50 mM KCL, 5.5 mM MgCl$_2$, 8% glycerol, 1% DMSO) (+dNTP) OR 1× Cloned Pfu buffer (Stratagene; Catalog #: 600153)
  2.5 U of Pfu (pol–/exo+)
  0.5 ul of stock diluted (1:500) Rox The reactions mixtures were subjected to the following temperature cycling conditions in an Mx3005P real-time PCR instrument (Stratagene): 1 cycle of 95 C 2 minutes; 50 cycles of 95 C 10 sec, 60 C 30 sec. Data were expressed as dRn (change in FAM fluorescence, normalized to the reference dye) with respect to cycle number. The results indicated that 3' flaps of 1-4 nucleotides (nts) were efficiently cleaved when the dye was attached at the 3' OH and not cleaved when attached to the 3' terminal base.

Additional experiments were performed in which a single target sequence was used with several probe sequences having varying lengths of 3' mismatch. A CCR2 3'FAM 7 labeled probe was used having 0-5 bases at the 3' end forming a non-complementary flap. The probes included Fam on the 3' OH of the terminal base. The probes were used in combination with a synthetic quenched target, a quencher complementary oligonucleotide (QC 3' flap 1) and Pfu exo+ pol– enzyme. Sequences for the probes, target, and QC used in this experiment are shown in FIG. 2B. The cleavage reactions were performed in a 25 ul reaction volume containing the following:

1× Cloned Pfu buffer (Stratagene; Catalog #: 600153)
  200 ng CCR2 artificial, quenched Target 4Q
  3 U Pfu exo+/pol– enzyme
  200 nM CCR2 3' Fam 7-0, 7-1, 7-2, 7-3, 7-4, or 7-5
  200 nM CCR2QC 3' flap 1

The reactions mixtures were subjected to the following temperature cycling conditions in an Mx3005P real-time PCR instrument (Stratagene): 1 cycle of 95 C 2 minutes; 50 cycles of 95 C 10 sec, 60 C 30 sec. The results (not shown) demonstrate that a 3 base 3' flap was cleaved most efficiently in this system. Thus, when taken together with the results of the prior experiment, 3' flap cleavage appears to occur most efficiently with a 1-4 base 3' flap, and preferably a 2 or 3 base 3' flap.

Example 2

Oligonucleotide Pair Reaction

A target nucleic acid sequence can be detected and/or measured by the following method illustrated in FIG. 5. FIG. 5 illustrates an embodiment of the invention utilizing a labeled oligonucleotide pair comprising an oligonucleotide probe (AB) having a 3' end which is non-complementary to the target and forms a 3' flap (B) and oligonucleotide A'*. The oligonucleotide probe (AB) has a first member of an interactive pair of labels at or near its 3' end (F1), and oligonucleotide A'* has a second member of an interactive pair of labels at or near its 5' end (F2). The interactive pair of labels interact when the oligonucleotide probe (AB) is hybridized to oligonucleotide A'* during at least one non-denaturing step of the reaction (e.g., 60° C.).

The reaction would also include a 3' nuclease and polymerase. In some embodiments, the 3' nuclease and polymerase activities are provided by separate proteins. In another embodiment the 3' nuclease and polymerase activities are provided by a single protein (e.g., Pfu DNA polymerase (pol+/exo+).

Region A is at least partially complementary to regions A' and A'*. The sequences of A' and A'* may or may not be different from each other, but each is capable of hybridizing to region A. In a one embodiment, sequence A hybridizes with the target (A'C') preferentially over sequence A'*. Similarly, sequence AB would hybridize with sequence A' preferentially over sequence A'*. In the embodiment depicted in FIG. 5, region B is non-complementary to sequence C'. This non-complementarity creates a 3' flap upon annealing of the oligonucleotide probe to the target.

Region B' can be any suitable length, and would often be in the range of 0-500 nucleotides and more often 1-10 nucleotides. Regions B, C, and C' may also be of any suitable length. Often the regions would be in the range of 1-500 nucleotides and more often 1-10 nucleotides. Sequences A, A', and A'* may be of any suitable length, often 1 to 1000 nucleotides in length, and more often 5 to 50 nucleotides in length.

The pair of interactive moieties (F1 and F2) produce a signal upon denaturation or degradation of the oligonucleotides to which they are operatively coupled. F1 and F2 may be attached at any position on their respective molecules.

Moiety F1 is preferably attached to AB in the region that will be removed by the 3' nuclease. In some embodiments, oligonucleotide A'* is blocked.

Upon annealing of the oligonucleotide probe (AB) to the target the 3' nuclease cleaves all or part of the 3' flap (B), sufficient to allow the polymerase to extend the uncleaved portion of the (AB) oligonucleotide to generate a nucleic acid strand that is complementary to the target. Cleavage and extension can be performed in under thermocycling reaction conditions (e.g., PCR) during the annealing/extension phase of a cycle (e.g., 60 C for 30 s). Cleavage of the 3' flap will also remove F1 from AB, thus reducing the number of labeled oligonucleotide probes (F1-labeled AB molecules) from the pool and increasing the number of unpaired A'* molecules. The unpaired A'* molecules are capable of generating a signal, since the AC portion of the strand synthesized by the polymerase contains no F1 moiety. Alternatively, the cleaved F-1 molecule generates the signal.

In an embodiment in which the F1 moiety is coupled to a region of the oligonucleotide probe (AB) that would not be removed by a 3' nuclease activity (e.g., 5' portion of AB), molecule A'* would be designed so that it would not bind to region AC under at least one of the non-denaturing conditions used in the assay due to the removal of one or more of the residues in region B by the 3' nuclease. Thereby, even if F1 were incorporated into the extended AB (now AC) strand, molecule A'* would be incapable of annealing to AC under such conditions, thus creating more unpaired A'* molecules and thus leading to an increase in signal.

The reaction may be performed under nucleic acid amplification reaction conditions in a thermocycling device and the generated signal can be measured in real-time. For example, the oligonucleotides of the invention, 3' nuclease (2.5 U of Pfu (pol−/exo+) and polymerase (2.5 U of Pfu (pol+/exo−), can be added to a reaction mixture containing a suitable buffer (15 mM of Tris-HCL (pH8), 50 mM KCL, 5.5 mM $MgCl_2$, 8% glycerol, 1% DMSO) (+dNTP) OR 1× Cloned Pfu buffer (Stratagene; Catalog #: 600153). The reaction mixtures are then subjected to the following temperature cycling conditions in an Mx3005P real-time PCR instrument (Stratagene): 1 cycle of 95 C 2 minutes; 50 cycles of (95 C 10 sec, 60 C 30 sec). Fluorescence could then be measured at the completion of each 60 C temperature incubation step.

In another embodiment, a 5' nuclease activity can be included in the reaction, such as a 5' exonuclease or endonuclease activity. Assays utilizing 5' nucleases in detection reactions are known in the art and described in U.S. Pat. Nos. 6,528,254; 6,548,250, 5,210,015, which are each herein incorporated by reference in their entirety. This 5' nuclease activity would degrade molecule A'* if A'* happened to be bound to region AC (in this embodiment, A'* would still be capable of binding to region A even if C and B' are not complementary). If a "reverse primer" is included in the reaction, capable of binding to the 3' terminal portion of AC and being extended by the polymerase, then thermocycling would lead to a polymerase chain reaction (PCR). In that case the extended reverse primer could aid in the cleavage of A'* when A'* is bound to AC (See U.S. Pat. Nos. 6,528,254; 6,548,250 and U.S. Patent Application Ser. No. 60/794,628, filed Apr. 24, 2006, each of which is herein incorporated by reference in their entirety). In this embodiment, after cleavage of A'* the F2 moiety (as a result of the 5' nuclease cleavage) and the F1 moiety (as a result of the 3' nuclease cleavage) would be free in the solution and would no longer interact, thus generating a signal indicative of the presence/amount of target.

Example 3

Comparison of Buffer Compositions

The following experiments were conducted to determine the optimal buffer conditions for generating a detectable signal. One of eight different targets (each 35 bases in length) were added to each reaction mixture (See FIG. 2A). Each target was designed to have from 0-7 nucleotides that are non-complementary to the 3' region of the probe (the probe is 30 bases long), so as to form a 3' flap in the probe. One of skill in the art would appreciate that these experiments could have been performed by adding a single target and varying the complementarity of the nucleotides at the 3' end of the probe to arrive at the same result.

The probes were labeled with an interactive pair of labels: BHQ2 at the 5' end and FAM at the 3' end. FAM was either directly coupled to the 3' OH or to the 3' terminal base. The cleavage reactions were performed in a 25 ul reaction volume containing the following:

200 nM of one of Targets 1-8 (See FIG. 2A)

200 nM of Probe 1A having (Fam on 3' OH; BHQ2 on 5' end; referred to as CCR2 Probe 1A) or 200 nM of Probe 1A having (Fam on the 3' base; BHQ2 on 5' end; referred to as CCR2__1A__3'FAM_base probe)

1× Probe buffer (15 mM of Tris-HCL (pH8), 50 mM KCL, 5.5 mM $MgCl_2$, 8% glycerol, 1% DMSO; also referred to as the Full Velocity Master Mix (minus polymerase) available from Stratagene, Calif,; (+dNTP) OR 1× Cloned Pfu buffer (Stratagene; Catalog #: 600153)

2.5 U of Pfu (pol−/exo+)

0.5 ul of stock diluted (1:500) Rox

The reactions mixtures were subjected to the following temperature cycling conditions in an Mx3005P real-time PCR instrument (Stratagene): 1 cycle of 95° C. 2 minutes; 50 cycles of 95° C. 10 sec, 60° C. 30 sec. Data were expressed as dRn (change in FAM fluorescence, normalized to the reference dye) with respect to cycle number. The results demonstrate that the exo$^+$/pol$^-$ enzyme cleaves the CCR21A probe most efficiently in the full velocity master mix buffer where there is a 2 nucleotide 3' flap on the probe. The results also demonstrated that a 1, 3, and 4 nucleotide flaps can also be cleaved in the FVMM buffer. The results demonstrate that the exo$^+$/pol$^-$ enzyme cleaves the CCR2 1A probe most efficiently in the cloned Pfu buffer where there is a 1 or 3 nucleotide 3' flap. The results also show that a 2 or 4 nucleotide flap can also be cleaved. The results also demonstrate that it is preferred to have the Fam attached to the 3' OH group rather than the 3' base, although having Fam on the 3' base provides some information regarding cleavage of the 3' flap that can be used to determine the presence of the target in a sample.

Example 4

Optimal 3' Flap Sequences

The following experiments were conducted to show how efficiently a 2-base 3' mismatch (labeled with Fam on the 3' hydroxyl group) is cleaved by the 3' nuclease activity of a Pfu pol$^-$ polymerase. One of four different targets (each 38 based in length) were added to each reaction mixture (See FIG. 5). Targets that are named TargNQ, when N is a number, have quencher moiety in the target molecule 5 nucleotides away from the two mismatching bases in the target. The targets that are named TargN, where N is a number have no quencher. Each target was designed to have 2 nucleotides that are non-complementary to the 3' region of the probe (each probe is 30 bases long), so as to form a 3' flap in the probe. Sixteen different oligonucleotide probe molecules were tested.

The probes were labeled with FAM at the 3' end. FAM was directly coupled to the 3' OH. The cleavage reactions were performed in a 25 ul reaction volume containing the following:
  200 nM of one of CCR2 Target oligonucleotide
  200 nM of CCR2 3' Fam oligonucleotide probe
  200 nM CCR2QC3' flap 1 (FIG. 11)
  1× Cloned Pfu buffer (Stratagene; Catalog #: 600153)
  3U of Pfu (pol−/exo+)

The reactions mixtures were subjected to the following temperature cycling conditions in an Mx3005P real-time PCR instrument (Stratagene): 1 cycle of 95° C. 2 minutes; 50 cycles of 95° C. 10 sec, 60° C. 30 sec. Data were expressed as either Rn (change in FAM fluorescence, normalized to the reference dye) with respect to cycle number, or raw fluorescence. The 5'-GA-3' mismatched flap was cleaved most efficiently, with only a small effect coming from the 2 nucleotides in the target that oppose the 2-nucleotide 3' flap. The presence of a quencher in the target did not have a major impact on the signal generated. This indicates that the 3'-FAM-labeled oligonucleotide probes are somewhat self-quenched, and the FAM signal increases upon the cleavage of the 3' terminal nucleotides away from the oligonucleotide. These results demonstrate that it may not be necessary to include a quenching moiety in the target, or in a complementary oligonucleotide (e.g., oligonucleotide A'* shown in FIG. 3).

FIG. 6 shows the effect of various 3' flap sequences on signal strength. Two different quenched target sequences were used. In addition, a quenching complementary oligonucleotide (QC 3' flap 1; 5'-(BHQ2)-GGTTGAGCAGG-TAAATGTCAGTCATCTGTA-(C3)-3') (SEQ ID NO:42) was included in the reaction. The quenching oligonucleotide binds to the FAM labeled oligonucleotide such that a 5-base, 3' flap is created at both 3' ends of the duplex. This QC oligo acts to further quench the signal generated by the uncleaved FAM oligonucleotide. These data also demonstrate that the 5'-GA-3' sequence is the most efficiently cleaved 3' flap.

Example 5

Optimal Extension Length in 3' FAM probe/CO or QC Duplex

The following experiments were performed to determine the effects of varying 3' flap lengths (i.e., the number of 3' nucleotides of a 3'FAM oligonucleotide probe that are not hybridized to the 5' end of a QC or CO complementary oligonucleotide (the CO is the same as the QC, but without the quencher) on signal generation under PCR conditions using an active DNA polymerase. Probe CCR2 3'FAM8 was used (see, FIG. 5 and FIG. 11).

The cleavage reactions were performed in a 25 ul reaction volume containing the following:
  1× Herculase II Buffer (Stratagene)
  0.0625 μl Herculase II enzyme
  100 nM CCR2 3'FAM8 oligonucleotide
  300 nM CCR2 R 199 (5'-TCATTTGCAGCAGAGT-GAGC-3') (SEQ ID NO:57)
  50 nM CCR2 QC3' flap 1 or 50 nM each CCR2 CO (FIG. 11)
  $10^3$ copies CCR2 PCR template The reactions mixtures were subjected to the following temperature cycling conditions in an Mx3005P real-time PCR instrument (Stratagene): 1 cycle of 95° C. 2 minutes; 50 cycles of 95° C. 10 sec, 60° C. 30 sec. The results are shown in FIG. 7. Data are expressed as Rn (change in FAM fluorescence, normalized to the reference dye) with respect to cycle number.

FIG. 7 shows the results when an active polymerase is used in a PCR reaction. Herculase II is Pfu DNA polymerase which has normal 3' exonuclease activity. The plots marked with X-s represent fluorescent signal when no target is present, just two PCR primers (one of which is labeled on its 3' OH with FAM and creates a 2-base mismatch with the target; and the other primer (CCR2 R 199) is unlabeled and perfectly matched to the complementary strand of the target). The reaction labeled "No QC or CO" does not contain complementary oligonucleotides ("QC=quenched complement and CO=complementary oligo). As shown in FIG. 12, there is no background signal in the absence of target (NTC). However there is strong signal in the presence of target. No quenching of the 3'-FAM labeled primer was needed. The plot labeled "QC 3' flap 1 (5b)" represents a reaction where the quenched complement of the 3' FAM labeled primer is also included in the reaction. This complement creates a duplex with the primer where both ends of the duplex have 5-base protruding 3' ends. The 5' end of "QC 3' flap 1" has a quencher attached to it (a variation of the oligo labeled as A'* in FIG. 3). FIG. 7 shows that the fluorescent baseline for this system (i.e., inclusion of QC 3' flap 1) is lower than the other systems. The quencher complement is quenching the FAM somewhat, as it should. However there is a little delay in Ct (cycle number at which the target is amplified above a threshold (e.g., background) when the quencher complement is added to the reaction. The effects of other complementary oligonucleotides, which had no quencher attached to them, were also tested. When they were included in the PCR reaction, the plots were labeled "CO Nb3'flap", where N represents the number of bases that the 5' end of CO is recessed from the 3' end of the FAM-labeled oligo/primer. In other words, a 3' extension or flap is formed by the 3'FAM oligonucleotide when the CO oligonucleotide duplexes with the 3'FAM-labeled oligonucleotide. FIG. 7 demonstrates that when the FAM-labeled 3' extension is only 3 bases long, the FAM-labeled 3' extension is cleaved in the presence or absence of target (olive colored plots with either dots or X's). However when the 3' extension is 4-bases long, there is a big difference in cleavage efficiency in the presence or absence of target (orange plots). When the 3' extension was 5-bases long, no 3' nuclease activity was observed unless the target was also present. This suggests that the 3' nuclease is efficient at cleaving 2-base long flaps, less efficient at cleaving 3' base flaps, much less efficient at cleaving 4-base flaps, and poor at cleaving 5-base flaps. Thus, it is preferred that when the 3'FAM oligonucleotide is used in a reaction in combination with a complementary control oligonucleotide, the 3'FAM oligonucleotide, when hybridized to the complementary control oligonucleotide, have a 4 or 5 base 3' flap.

It is preferred to include a CO or QC oligonucleotide in the reactions described herein because, at times, false positive signals can be observed in the absence of the target nucleic acid. For example, it has been observed that a delayed fluorescence signal can be detected in the absence of target unless a QC is included in the reaction (data not shown). The inclusion of a QC lowers that baseline fluorescence, and also creates a delay in the Ct value. The QC and CO oligonucleotides may function to reduce the formation of primer dimers and other unwanted priming events that can lead to unwanted cleavage of the 3'FAM flap. By hybridizing the 3'FAM oligonucleotide to a control complementary oligonucleotide, unless bound to the proper target, the QC and CO may function to occupy the 3'FAM labeled oligonucleotide and make it less available for unwanted priming events.

Example 6

FAM7 Standard Curve

The following experiments were performed to demonstrate the efficiency of 3' flap cleavage at low template (target) concentrations under PCR conditions using an active DNA polymerase. Probe CCR2 3'FAM7 was used (see, FIG. 5).

The cleavage reactions were performed in a 25 ul reaction volume containing the following:
1× Herculase II Buffer (Stratagene)
0.0625 μl Herculase II enzyme
200 nM CCR2 3'FAM7 oligonucleotide (FIG. 5)
400 nM CCR2 R 199 (5'-TCATTTGCAGCAGAGT-GAGC-3') (SEQ ID NO:57)
25 nM CCR2 QC3' flap 1 (FIG. 11)
$10^5$ to 10 copies CCR2 PCR template (serial dilutions)

The reactions mixtures were subjected to the following temperature cycling conditions in an Mx3005P real-time PCR instrument (Stratagene): 1 cycle of 95° C. 2 minutes; 50 cycles of 95° C. 10 sec, 60° C. 30 sec. The results are shown in FIGS. 8 and 9. Data are expressed as dRn (change in FAM fluorescence, normalized to the reference dye) with respect to cycle number.

The data in FIG. 8 shows the standard curve using the CCR2 3'FAM7 labeled primer that has a 5'-AG-3' flap when bound to target. The plot marked "NTC" indicates the absence of the target sequence in the amplification reaction.

The standard curve was performed using serial dilutions of PCR template from $10^5$ copies to 10 copies. The optimal concentrations of 3'Fam7 labeled primer, Rev 199 primer, and Quencher complement were used in Herculase II buffer. The optimal amount of Herculase enzyme (0.0625 ul~1.25 U) was used as determined in a previous titration reaction. Three replicates were run for each template concentration and the data was treated collectively to yield the plots shown in FIG. 8.

FIG. 9 shows the plot of the Ct values vs the template amount for the standard curve shown in FIG. 8. A best fit line was plotted across all points to yield an Rsq (0.998) and Efficiency calculation (94.3%).

These data demonstrate that the optimized CCR2 3' nulcease assay works very efficiently to amplify the target even at very low template concentrations (the amplification plot for 10 copies of the target shows strong signal and similar final fluorescence plateau as higher template amounts indicating efficient amplification without a the formation of primer dimers). The high efficiency shows that the labeled primer can function well as a primer even though 3' nuclease activity is required prior to extension to cleave the 3' flap. These data demonstrate that this assay is an efficient, sensitive, robust means of detecting a specific target using QPCR.

All patents, patent applications, and published references cited herein are hereby incorporated by reference in their entirety. While this invention has been particularly shown and described with references to preferred embodiments thereof, it will be understood by those skilled in the art that various changes in form and details may be made therein without departing from the scope of the invention encompassed by the appended claims.

---

What is claimed is:

1. A composition comprising:
a labeled oligonucleotide pair, comprising:
a first oligonucleotide and a second oligonucleotide, wherein said first oligonucleotide comprises a 5' region and a 3' region, wherein the 5' region is complementary to a region of a target nucleic acid and the 3' region is non-complementary to the target nucleic acid, and wherein a label is operatively coupled to said 3' region; and wherein said second oligonucleotide is not the target nucleic acid, and wherein said second oligonucleotide is at least partially complementary to said first oligonucleotide, and forms a duplex with said 5' region of said first oligonucleotide under non-denaturing conditions provided said first oligonucleotide is not hybridized to the target nucleic acid ; and said composition further comprising a 3'-5' nuclease.

2. The composition of claim 1, wherein said label is a first member of an interactive pair of labels.

3. The composition of claim 2, wherein a second member of said interactive pair of labels is operatively coupled to said oligonucleotide pair.

4. The composition of claim 3, wherein said second member of said interactive pair of labels is operatively coupled to said second oligonucleotide.

5. The composition of claim 1, wherein at least a 3' terminal nucleotide of said first oligonucleotide is non-complementary to said second oligonucleotide.

6. The composition of claim 5, wherein one to five 3' terminal nucleotides of said first oligonucleotide are non-complementary to said second oligonucleotide.

7. The composition of claim 5, wherein one to ten 3' terminal nucleotides of said first oligonucleotide are non-complementary to said second oligonucleotide.

8. The composition of claim 1, wherein at least a 3' terminal nucleotide of said second oligonucleotide is non-complementary to said first oligonucleotide.

9. The composition of claim 8, wherein one to five 3' terminal nucleotide of said second oligonucleotide is non-complementary to said first oligonucleotide.

10. The composition of claim 8, wherein one to ten 3' terminal nucleotides of said second oligonucleotide is non-complementary to said first oligonucleotide.

11. The composition of claim 1, further comprising an oligonucleotide primer.

12. The composition of claim 1, further comprising a nucleic acid polymerase.

13. A method for detecting a target nucleic acid in a sample, the method comprising:
a. contacting a sample comprising the target nucleic acid with:
a first oligonucleotide comprising a 5' region and a 3' region, wherein the 5' region is complementary to a region of the target nucleic acid and the 3' region is non-complementary to the target nucleic acid,
a second oligonucleotide that forms a duplex with said 5' region of said first oligonucleotide under non-denaturing conditions; and
a 3'-5' nuclease, under conditions that permit the formation of a cleavage structure comprising said target and said first oligonucleotide, wherein said 3' region of said first oligonucleotide forms a 3' flap;
b. cleaving said 3' flap of said first oligonucleotide with said 3'-5' nuclease; and
c. detecting and/or measuring the cleavage of said 3' flap, wherein detecting and/or measuring the cleavage of said 3' flap is indicative of the presence and/or amount of the target nucleic acid.

14. The method of claim 13, wherein a label is operatively coupled to the 3' region of said first oligonucleotide.

15. The method of claim 14, wherein said label is a first member of an interactive pair of labels.

16. The method of claim 15, wherein a second member of an interactive pair of labels is operatively coupled to said second oligonucleotide.

17. The method of claim 13, wherein one to five 3' terminal nucleotides of said first oligonucleotide are non-complementary to said second oligonucleotide.

18. The method of claim 13, wherein one to ten 3' terminal nucleotides of said first oligonucleotide are non-complementary to said second oligonucleotide.

19. The method of claim 13, wherein at least a 3' terminal nucleotide of said second oligonucleotide is non-complementary to the first oligonucleotide.

20. The method of claim 19 wherein one to five 3' terminal nucleotides of said second oligonucleotide are non-complementary to said first oligonucleotide.

21. The method of claim 19, wherein one to ten 3' terminal nucleotides of said second oligonucleotide are non-complementary to said first oligonucleotide.

22. The method of claim 15, wherein said first oligonucleotide further comprises a second member of an interactive pair of labels operatively coupled to said first oligonucleotide 5' to said 3' region.

23. A method for detecting a target nucleic acid in a sample, the method comprising:
- a. forming a reaction mixture by contacting a sample comprising the target nucleic acid with:
  - a first oligonucleotide comprising a 5' region and a 3' region, wherein the 5' region is complementary to the target nucleic acid and the 3' region is non-complementary to the target nucleic acid,
  - a second oligonucleotide that forms a duplex with said 5' region of said first oligonucleotide under non-denaturing conditions;
  - a 3'-5' nuclease; and
  - a polymerase;
- b. subjecting said reaction mixture to conditions which permit:
  - annealing of said first oligonucleotide to said target nucleic acid, wherein the 3' region of said first oligonucleotide forms a 3' flap;
  - cleaving said flap from said first oligonucleotide with said 3'-5' nuclease, and
  - extending said cleaved first oligonucleotide with said polymerase, thereby generating a nucleic acid strand complementary to said target nucleic acid; and
- c. detecting and/or measuring the cleavage of said 3' flap, whereby said target nucleic acid is detected.

24. The method of claim 23, wherein a label is operatively coupled to said 3'region of said first oligonucleotide.

25. The method of claim 24, wherein said label is a first member of an interactive pair of labels.

26. The method of claim 25, wherein said step of detecting and/or measuring the cleavage of said flap comprises detecting and/or measuring a signal produced from said first member of said interactive pair of labels.

27. The method of claim 25, wherein said first oligonucleotide further comprises a second member of an interactive pair of labels operatively coupled to said first oligonucleotide 5' to said 3' region.

28. The method of claim 25, wherein a second member of an interactive pair of labels is operatively coupled to said second oligonucleotide.

29. The method of claim 23, wherein one to five 3' terminal nucleotides of said first oligonucleotide are non-complementary to said second oligonucleotide.

30. The method of claim 23, wherein one to ten 3' terminal nucleotides of said first oligonucleotide are non-complementary to said second oligonucleotide.

31. The method of claim 23, wherein at least a 3' terminal nucleotide of said second oligonucleotide is non-complementary to the first oligonucleotide.

32. The method of claim 31, wherein one to five 3' terminal nucleotides of said second oligonucleotide are non-complementary to said first oligonucleotide.

33. The method of claim 31, wherein one to ten 3' terminal nucleotides of said second oligonucleotide are non-complementary to said first oligonucleotide.

34. A method for detecting a target nucleic acid in a sample, the method comprising:
- a. forming a reaction mixture by contacting the target nucleic acid with a forward primer, a reverse primer and a polymerase;
- b. subjecting said reaction mixture to conditions that permit the amplification of said target nucleic acid;
- c. forming a second reaction mixture by contacting said amplified target nucleic acid with:
  - a first oligonucleotide comprising a 5' region and a 3' region, wherein the 5' region is complementary to the target nucleic acid and the 3' region is non-complementary to the target nucleic acid;
  - a second oligonucleotide that forms a duplex with said 5' region of said first oligonucleotide under non-denaturing conditions; and
  - a 3'-5' nuclease;
  - and subjecting said reaction mixture to conditions which permit:
    - annealing of said first oligonucleotide to said target nucleic acid, wherein the 3' region of said first oligonucleotide forms a flap; and
    - cleaving said flap from said first oligonucleotide with said 3'-5' nuclease; and
- d. detecting and/or measuring the cleavage of said flap, whereby said target nucleic acid is detected.

35. The method of claim 34, wherein a label is operatively coupled to said 3' region of said first oligonucleotide.

36. The method of claim 35, wherein said label is a first member of an interactive pair of labels.

37. The method of claim 36, wherein said step of detecting and/or measuring the cleavage of said flap comprises detecting and/or measuring a signal produced from said first member of said interactive pair of labels.

38. The method of claim 36, wherein said first oligonucleotide further comprises a second member of an interactive pair of labels operatively coupled to said first oligonucleotide 5' to said 3' region.

39. The method of claim 36, wherein said second oligonucleotide is operatively coupled to a second member of an interactive pair of labels, wherein said first and said second members of said interactive pair of labels interact when said first oligonucleotide and said second oligonucleotide hybridize, and do not interact when said first oligonucleotide and said second oligonucleotide dissociate.

40. The method of claim 34, wherein one to five 3' terminal nucleotides of said first oligonucleotide are non-complementary to said second oligonucleotide.

41. The method of claim 34, wherein one to ten 3' terminal nucleotides of said first oligonucleotide are non-complementary to said second oligonucleotide.

42. The method of claim 34, wherein at least a 3' terminal nucleotide of said second oligonucleotide is non-complementary to the first oligonucleotide.

43. The method of claim 42, wherein one to five 3' terminal nucleotides of said second oligonucleotide are non-complementary to said first oligonucleotide.

44. The method of claim 42, wherein one to ten 3' terminal nucleotides of said second oligonucleotide are non-complementary to said first oligonucleotide.

45. A method for detecting a target nucleic acid in a sample, the method comprising:
- a. forming a reaction mixture by contacting a sample comprising the target nucleic acid with:
  - a first oligonucleotide comprising a 5' region and a 3' region, wherein the 5' region is complementary to the target nucleic acid and the 3' region is non-complementary to the target nucleic acid,
  - a second oligonucleotide that forms a duplex with said 5' region of said first oligonucleotide under non-denaturing conditions, and
  - a 3'-5' nuclease;
- b. subjecting said reaction mixture to conditions which permit:
  - annealing of said first oligonucleotide to said target nucleic acid, wherein said 3' region of said first oligonucleotide forms a 3' flap when annealed to said target nucleic acid, and cleaving said 3' flap of said first oligonucleotide with said 3'-5' nuclease; and c. detecting and/or measuring the cleavage of said 3' flap thereby detecting the target nucleic acid.

46. The method of claim 45, wherein a label is operatively coupled to the 3' region of said first oligonucleotide.

47. The method of claim 46, wherein said label is a first member of an interactive pair of labels.

48. The method of claim 47, wherein a second member of an interactive pair of labels is operatively coupled to said second oligonucleotide, wherein said first and said second members of said interactive pair of labels interact when said first oligonucleotide and said second oligonucleotide hybridize, and do not interact when said first oligonucleotide and said second oligonucleotide dissociate.

49. The method of claim 47, wherein said step of detecting and/or measuring the cleavage of said 3' flap comprises detecting and/or measuring a signal produced from said first member of said interactive pair of labels.

50. The method of claim 47, wherein said first oligonucleotide further comprises a second member of an interactive pair of labels operatively coupled to said first oligonucleotide 5' to said 3' region.

51. The method of claim 45, wherein one to five 3' terminal nucleotides of said first oligonucleotide are non-complementary to said second oligonucleotide.

52. The method of claim 45, wherein one to ten 3' terminal nucleotides of said first oligonucleotide are non-complementary to said second oligonucleotide.

53. The method of claim 45, wherein at least a 3' terminal nucleotide of said second oligonucleotide is non-complementary to the first oligonucleotide.

54. The method of claim 53 wherein one to five 3' terminal nucleotides of said second oligonucleotide are non-complementary to said first oligonucleotide.

55. The method of claim 53, wherein one to ten 3' terminal nucleotides of said second oligonucleotide are non-complementary to said first oligonucleotide.

56. The method of claim 23, or 34, wherein said nuclease and said polymerase are the same polypeptide.

57. The method of claim 23 or 34, wherein said nuclease and the polymerase are different polypeptides.

58. The method of any one of claims 13, 23, 34, or 45, wherein said nuclease is *Pyrococcus furiosus* (Pfu) DNA polymerase, *Thermococcus litoralis* DNA polymerase, *Thermococcus barossii* DNA polymerase, *Thermococcus gorganarius* DNA polymerase or *E. coli* DNA polymerase I.

59. The method of anyone of claims 13, 23, 34, or 45, wherein the 3' region is one nucleotide.

60. The method of anyone of claims 13, 23, 34, or 45, wherein the 3' region is two nucleotides.

61. The method of anyone of claims 13, 23, 34, or 45, wherein the 3' region is three nucleotides.

62. The method of anyone of claims 13, 23, 34, or 45, wherein the 3' region is four nucleotides.

63. The method of any one of claims 23 or 34, wherein the polymerase is selected from the group consisting of: *Pyrococcus furiosus* (Pfu) DNA polymerase, *Thermococcus litoralis* DNA polymerase, *Thermococcus barossii* DNA polymerase, *Thermococcus gorganarius* DNA polymerase and *E. coli* DNA polymerase I.

64. The method of claims 13, 23, 34, or 45, wherein the 3'-5' nuclease is thermostable.

65. The method of claims 23 or 34, wherein the 3'-5' nuclease and polymerase are thermostable.

66. The method of any one of claims 13, 23, 34, or 45, wherein said 3'-5' nuclease is *Pyrococcus furiosus* (Pfu) polymerase.

67. The method of anyone of claims 13, 23, 34, or 45, wherein the target nucleic acid is detected by detecting a change in fluorescence intensity.

68. The method of anyone of claims 16, 22, 27, 28, 38, 39, 48, or 50, wherein the interactive pair of labels comprises a quencher and a fluorophore.

69. The composition of claim 1, wherein Tm of a hybrid formed between the first oligonucleotide and the second oligonucleotide is less than the Tm of a hybrid formed between the first oligonucleotide and the target nucleic acid.

* * * * *